US010533204B2

(12) United States Patent
Hamana et al.

(10) Patent No.: US 10,533,204 B2
(45) Date of Patent: Jan. 14, 2020

(54) METHOD FOR AMPLIFYING A T CELL RECEPTOR (TCR) CDNA

(71) Applicants: NATIONAL UNIVERSITY CORPORATION UNIVERSITY OF TOYAMA, Toyama-shi, Toyama (JP); SC WORLD, INC., Toyama-shi, Toyama (JP)

(72) Inventors: Hiroshi Hamana, Toyama (JP); Hiroyuki Kishi, Toyama (JP); Atsushi Muraguchi, Toyama (JP); Kiyomi Shitaoka, Toyama (JP)

(73) Assignees: National University Corporation University of Toyama, Toyama-shi (JP); SC World, Inc., Toyama-shi (JP)

( * ) Notice: Subject to any disclaimer, the term of this patent is extended or adjusted under 35 U.S.C. 154(b) by 133 days.

(21) Appl. No.: 15/314,862

(22) PCT Filed: May 29, 2015

(86) PCT No.: PCT/JP2015/065577
§ 371 (c)(1),
(2) Date: Nov. 29, 2016

(87) PCT Pub. No.: WO2015/182749
PCT Pub. Date: Dec. 3, 2015

(65) Prior Publication Data
US 2017/0183700 A1 Jun. 29, 2017

(30) Foreign Application Priority Data
May 30, 2014 (JP) ................. 2014-113308

(51) Int. Cl.
C12P 19/34 (2006.01)
C07K 14/725 (2006.01)
C12Q 1/6886 (2018.01)
A61K 48/00 (2006.01)

(52) U.S. Cl.
CPC .......... C12P 19/34 (2013.01); C07K 14/7051 (2013.01); C12Q 1/6886 (2013.01); A61K 48/00 (2013.01); C12Q 2600/158 (2013.01)

(58) Field of Classification Search
None
See application file for complete search history.

(56) References Cited

U.S. PATENT DOCUMENTS

2006/0134704 A1    6/2006   Muraguchi et al.
2013/0302801 A1*  11/2013   Asbury ................ C12Q 1/6883
                                                          435/6.11
2015/0203886 A1    7/2015   Kishi et al.

FOREIGN PATENT DOCUMENTS

| EP | 1 921 144 A2 | 5/2008 |
| JP | 2004-187676 A | 7/2004 |
| JP | 4069133 B2 | 4/2008 |
| JP | 2012-164442 A | 8/2012 |
| WO | WO 2012/027503 A2 | 3/2012 |
| WO | WO 2013/009967 A2 | 1/2013 |
| WO | WO 2013/188872 A1 | 12/2013 |
| WO | WO 2014/0175333 A1 | 1/2014 |

OTHER PUBLICATIONS

Rychlik et al., A computer program for choosing optimal oligonucleotides for filter hybridization, sequencing and in vitro amplification of DNA, Nucleic Acids Research 17(21), 8543-8555 (1989). (Year: 1989).*
Extended European Search Report issued in counterpart European Patent Application No. 15798675.3 dated Nov. 28, 2017 (Ten (10) pages).
Bolotin et al., "Next generation sequencing for TCR repertoire profiling: Platform-specific features and correction algorithms", European Journal of Immunology, vol. 42, No. 11, Sep. 24, 2012, pp. 3073-3083, XP055235351.
Freeman et al, "Profiling the T-cell receptor beta-chain repertoire by massively parallel sequencing", Genome Research, Cold Spring Harbor Laboratory Press, US, vol. 19, No. 10, Oct. 1, 2009, pp. 1817-1824, XP002636496.
International Search Report (PCT/ISA/210) issued in PCT Application No. PCT/JP2015/065577 dated Jul. 28, 2015, with English translation (four (4) pages).

(Continued)

Primary Examiner — Kenneth R Horlick
(74) Attorney, Agent, or Firm — Crowell & Moring LLP

(57) ABSTRACT

As a method for highly efficiently amplifying a TCR cDNA in a short period of time, there is provided a method for amplifying a T cell receptor (TCR) cDNA, which comprises the following step (1) and step (2):

(1) the step of performing PCR by using at least one kind of the L primer mentioned below, the C primer 1 or UTR primer 1 mentioned below, and cDNA obtained from a single cell as the template to obtain an amplification product 1;
    an L primer of 30- to 60-nucleotide length comprising an adapter part of 15- to 25-nucleotide length, and a leader region-annealing part of 15- to 25-nucleotide length, which is ligated downstream from the adapter part, and can anneal to a part of a leader region containing a translation initiation codon, or an upstream part thereof,
    a C primer 1 of 15- to 25-nucleotide length, which can anneal to a part of a constant region, or a UTR primer 1 of 15- to 25-nucleotide length, which can anneal to a part of a 3' untranslated region;
(2) the step of performing PCR by using the adaptor primer mentioned below, the C primer 2 or UTR primer 2 mentioned below, and the amplification product 1 as the template to obtain an amplification product 2;
    an adapter primer of 15- to 25-nucleotide length, which can anneal to the adapter part of the amplification product 1,
    a C primer 2 of 15- to 25-nucleotide length, which can anneal to a part of the constant region existing upstream from the region to which the C primer 1 anneals, or a UTR primer 2 of 15- to 25-nucleotide length, which can anneal to a part of the 3' untranslated region existing upstream from the region to which the UTR primer 1 anneals.

9 Claims, 15 Drawing Sheets
Specification includes a Sequence Listing.

(56) References Cited

OTHER PUBLICATIONS

Japanese-language Written Opinion (PCT/ISA/237) issued in PCT Application No. PCT/JP2015/065577 dated Jul. 28, 2015 (four (4) pages).
Kobayashi et al., "A New Cloning and Expression System Yields and Validates TCRs from Blood Lymphocytes of Patients with Cancer within 10 Days", Nature Medicine, vol. 19, No. 11, Nov. 2013, pp. 1542-1548.
Moysey et al., "Amplification and One-Step Expression Cloning of Human T Cell Receptor Genes", Analytical Biochemistry, vol. 326, 2004, pp. 284-286.
Heinrichs et al., "Universal Cloning and Direct Sequencing of Rearranged Antibody V Genes Using C Region Primers, Biotin-Captured cDNA and One-Side PCR", Journal of Immunological Methods, vol. 178, 1995, pp. 241-251.
Birkholz et al., "A Fast and Robust Method to Clone and Functionally Validate T-Cell Receptors", Journal of Immunological Methods, vol. 346, 2009, pp. 45-54.
Coloma et al., "Primer Design for the Cloning of Immunoglobulin Heavy-Chain Leader-Variable Regions from Mouse Hybridoma Cells Using the PCR", BioTechniques, vol. 11, No. 2, 1991, pp. 152-154, and 156.
Muraguchi, "TCR Cloning to TCR o Mochiita Saibo Chiryo, HBV cccDNA no Seigyo to Haijo o Mezasu Shinki Men'eki Iryoyaku no Kaihatsu", Heisei 25 Nendo Sokatsu Buntan Kenkyu Hokokusho, Mar. 2014, pp. 34-36.
International Preliminary Report on Patentability (PCT/IB/338 & PCT/IPEA/409) issued in PCT Application No. PCT/JP2015/065577 dated Dec. 1, 2016, with English translation (19 pages).
Unverified translation of document B2 (JP 2004-187676 A) previously filed on Nov. 29, 2016 (19 pages).
Unverified translation of document B3 (WO 2014/017533 A1) previously filed on Nov. 29, 2016 (29 pages).
Unverified translation of document B1 (JP 4069133 B2) previously filed on Nov. 29, 2016 (19 pages).

* cited by examiner

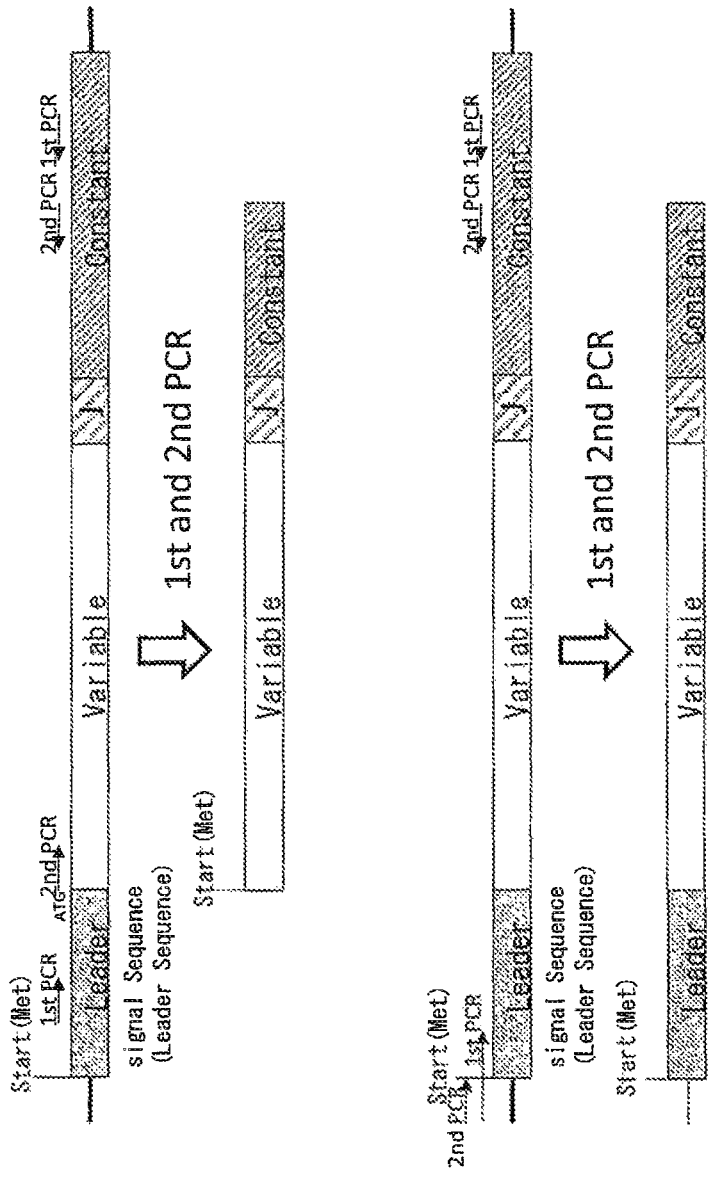
[Fig. 3]

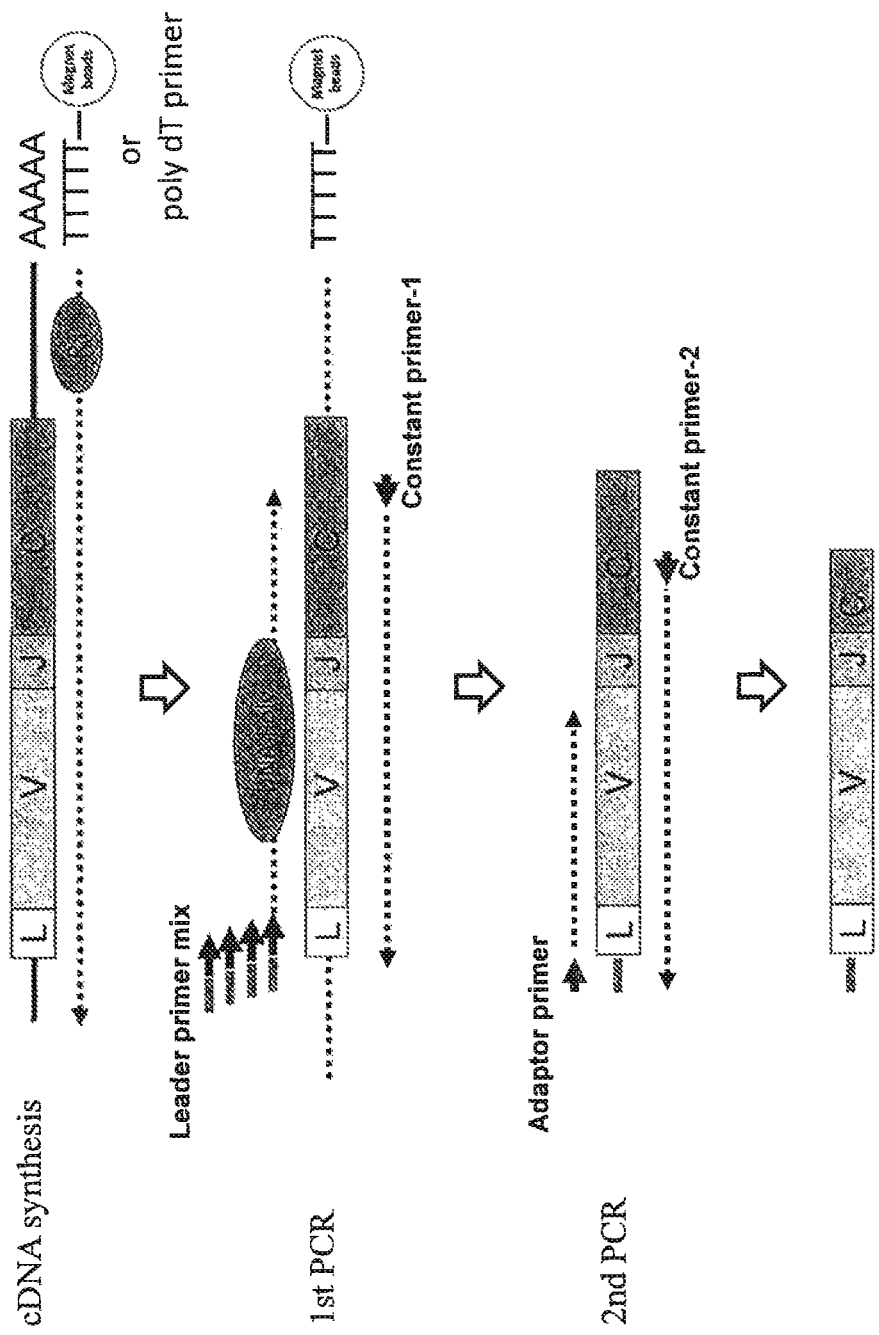

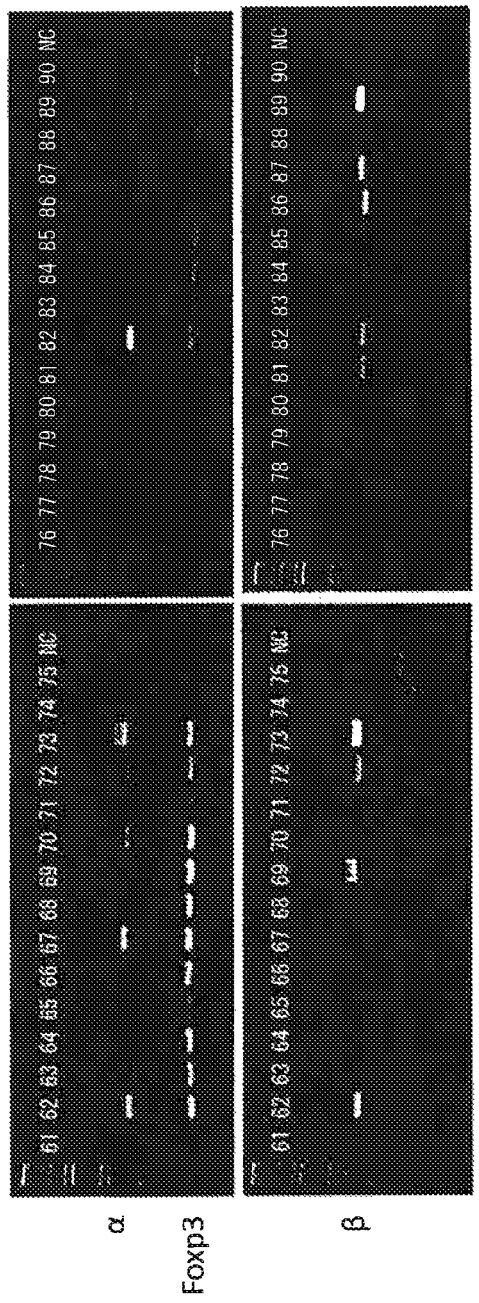
[Fig. 5]

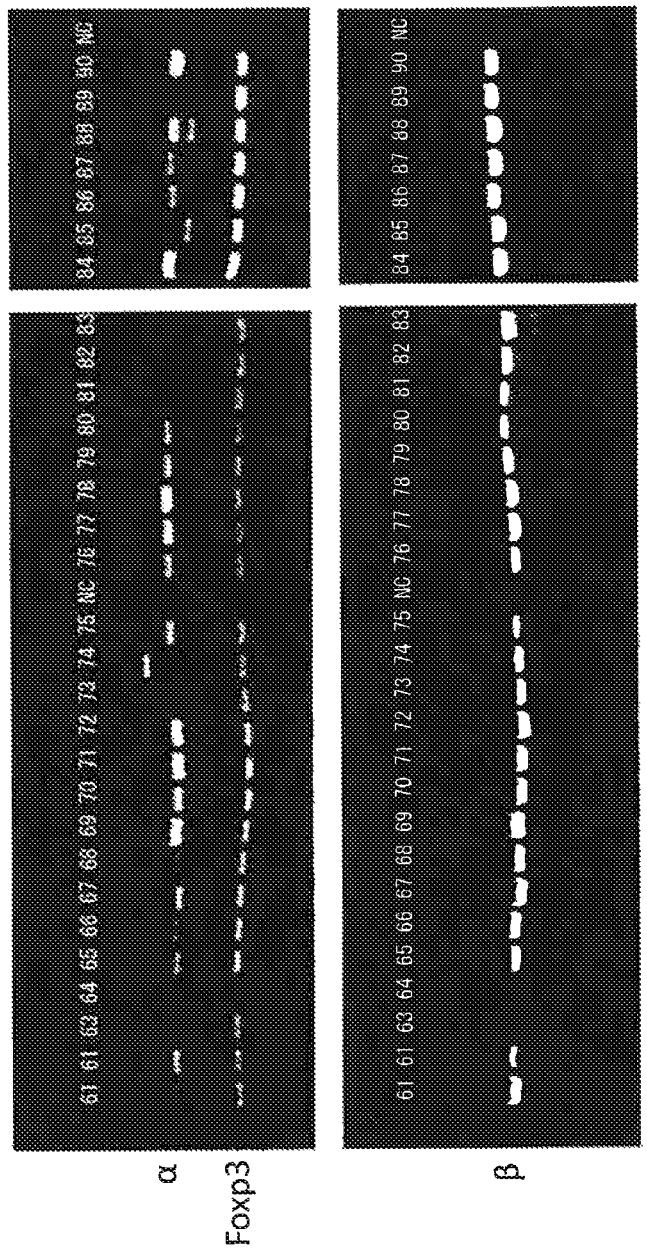
[Fig. 6]

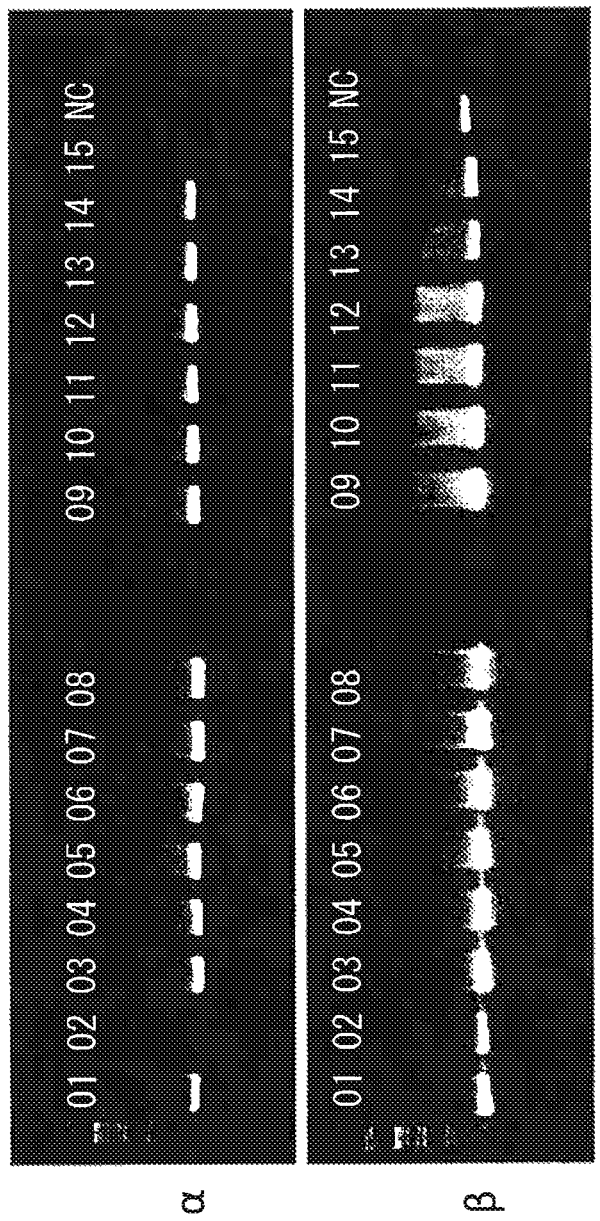
[Fig. 7]

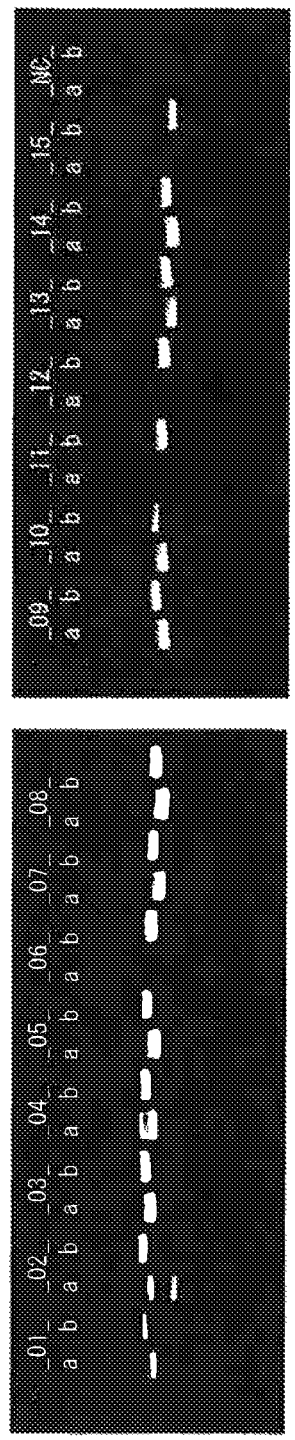
[Fig. 8]

[Fig. 9]
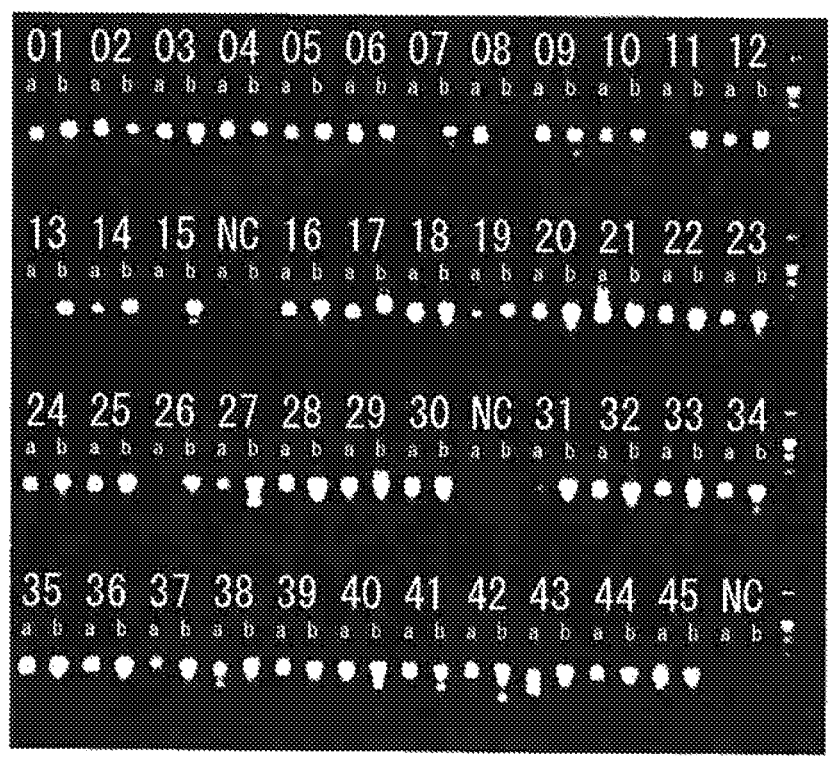

[Fig. 11]
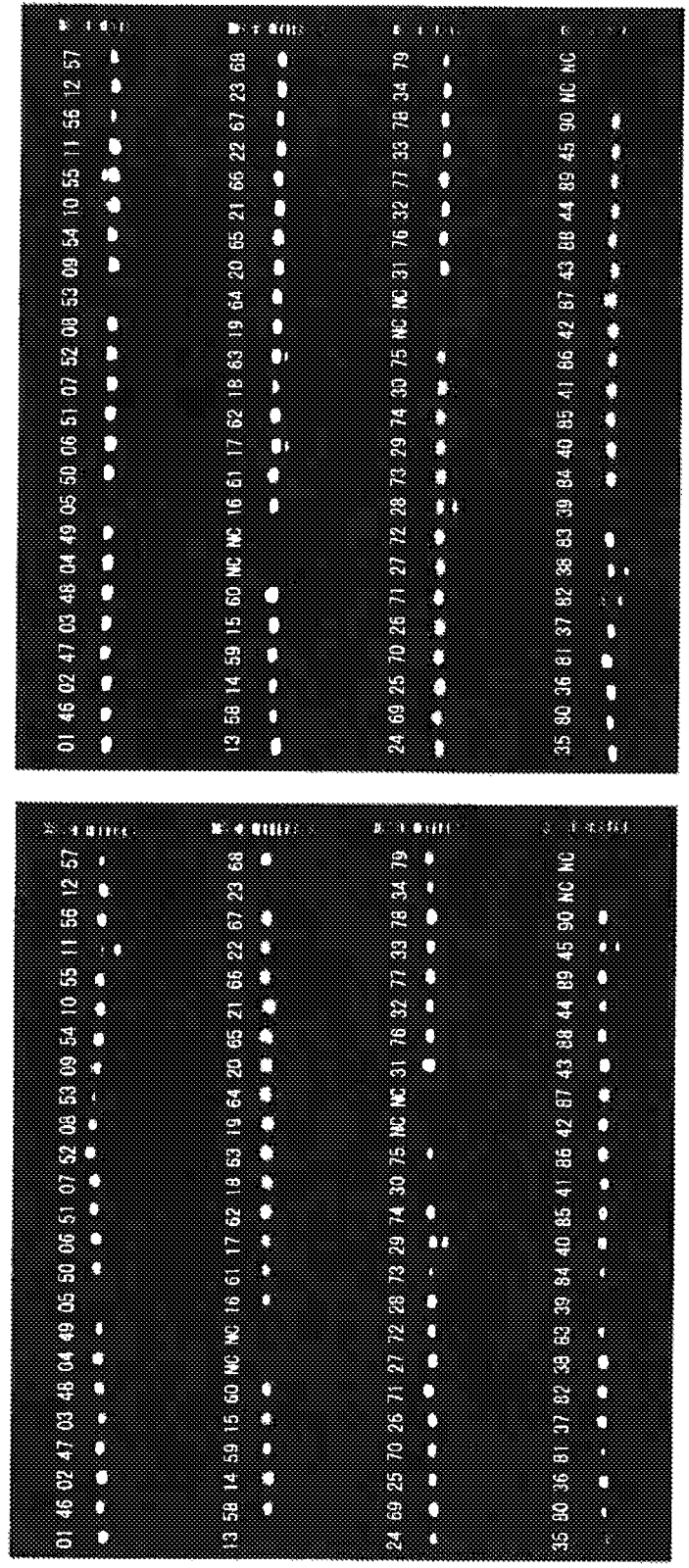

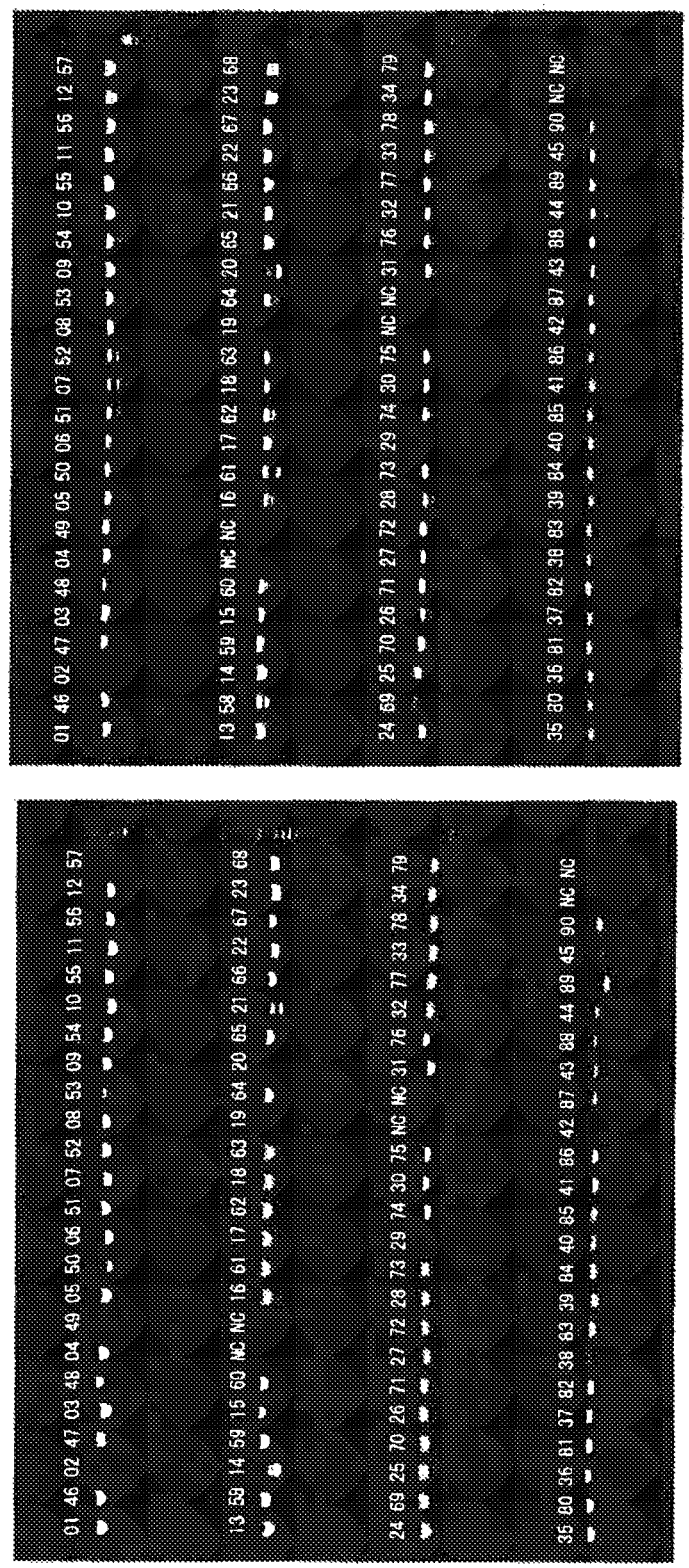
[Fig. 12]

[Fig. 13]

| No. | Primer Name | Primer Sequence (5'-> 3') | SEQ ID NO. |
|---|---|---|---|
| 1 | mAL-1 | TGGAGGAGAACCCTGGACCTatgctgcagatgtgggggtttg | 283 |
| 2 | mAL-2 | TGGAGGAGAACCCTGGACCTatgaagcaggtggcaaaagtg | 284 |
| 3 | mAL-3-1 | TGGAGGAGAACCCTGGACCTatgaagacRgtgactggacc | 285 |
| 4 | mAL-3-4 | TGGAGGAGAACCCTGGACCTatgaaaacagtgRctggacc | 286 |
| 5 | mAL-4-2 | TGGAGGAGAACCCTGGACCTatggagaggagcccggggaac | 287 |
| 6 | mAL-4-3 | TGGAGGAGAACCCTGGACCTatgSagaggaacctggagc | 288 |
| 7 | mAL-5-1 | TGGAGGAGAACCCTGGACCTatgaagacagctattcatgc | 289 |
| 8 | mAL-5D-4 | TGGAGGAGAACCCTGGACCTatgaaaacatatgctcctac | 290 |
| 9 | mAL-6-1 | TGGAGGAGAACCCTGGACCTatgaactattctccagctttagtg | 291 |
| 10 | mAL-6-2 | TGGAGGAGAACCCTGGACCTatgaacacttctccagctttag | 292 |
| 11 | mAL-6-3 | TGGAGGAGAACCCTGGACCTatgaacaattccccagctttag | 293 |
| 12 | mAL-6-4 | TGGAGGAGAACCCTGGACCTatgaatacttctccagttttag | 294 |
| 13 | mAL-6-5 | TGGAGGAGAACCCTGGACCTatgaacctttgtcctgaactg | 295 |
| 14 | mAL-6-6 | TGGAGGAGAACCCTGGACCTatggactYttctccaggcttc | 296 |
| 15 | mAL-7-1 | TGGAGGAGAACCCTGGACCTatgaagtccttgtgtgtttcac | 297 |
| 16 | mAL-7-2 | TGGAGGAGAACCCTGGACCTatgaaatcctttagtatttccctag | 298 |
| 17 | mAL-7-3 | TGGAGGAGAACCCTGGACCTatgaaatccttgagtgtttc | 299 |
| 18 | mAL-7D-4 | TGGAGGAGAACCCTGGACCTatgaaatccttgagtgttttac | 300 |
| 19 | mAL-7-6 | TGGAGGAGAACCCTGGACCTatgcattccttacatgtttcac | 301 |
| 20 | mAL-8-1 | TGGAGGAGAACCCTGGACCTatgcacagcctcctggggttg | 302 |
| 21 | mAL-8-2 | TGGAGGAGAACCCTGGACCTatgaacagattcctgggaa | 303 |
| 22 | mAL-9-1 | TGGAGGAGAACCCTGGACCTatgctcctggtYctcatctcg | 304 |
| 23 | mAL-9-2 | TGGAGGAGAACCCTGGACCTatgctcctgYtgctcctcc | 305 |
| 24 | mAL-9D-4 | TGGAGGAGAACCCTGGACCTatgctcctggcactcctcc | 306 |
| 25 | mAL-10 | TGGAGGAGAACCCTGGACCTatgaagacatccttcacactg | 307 |
| 26 | mAL-11*01 | TGGAGGAGAACCCTGGACCTatgaaaaagtgccttagtgcctg | 308 |
| 27 | mAL-11*02 | TGGAGGAGAACCCTGGACCTatgaaaaagYgcctgagtgcc | 309 |
| 28 | mAL-12-1 | TGGAGGAGAACCCTGGACCTatgcgtcctgtcacctgctc | 310 |
| 29 | mAL-12D-1*01 | TGGAGGAGAACCCTGGACCTatgaacatgcgtcctgWcac | 311 |
| 30 | mAL-12D-1*02 | TGGAGGAGAACCCTGGACCTatgcgtcctgWcacctcctc | 312 |
| 31 | mAL-12-2 | TGGAGGAGAACCCTGGACCTatgaacatgcatcctgtcacctg | 313 |
| 32 | mAL-12-3 | TGGAGGAGAACCCTGGACCTatgcgtcctgRcacctgctca | 314 |
| 33 | mAL-13-1 | TGGAGGAGAACCCTGGACCTatgaacaggctgctgtgctc | 315 |
| 34 | mAL-13D-1 | TGGAGGAGAACCCTGGACCTatgaagaggctgctgagctc | 316 |
| 35 | mAL-13-2 | TGGAGGAGAACCCTGGACCTatgaagaggctgatgtg | 317 |
| 36 | mAL-14-1 | TGGAGGAGAACCCTGGACCTatggacaWgatcctgacagca | 318 |
| 37 | mAL-14D-1 | TGGAGGAGAACCCTGGACCTatggacaagattctgacagcatc | 319 |
| 38 | mAL-14D-2 | TGGAGGAGAACCCTGGACCTatggacaagaacctgacagca | 320 |
| 39 | mAL-15-1 | TGGAGGAGAACCCTGGACCTatgcctcctcacagcctg | 321 |
| 40 | mAL-15-2 | TGGAGGAGAACCCTGGACCTatgcctcctcagagcctgctc | 322 |
| 41 | mAL-16 | TGGAGGAGAACCCTGGACCTatgctgattctaagcctg | 323 |
| 42 | mAL-16*01 | TGGAGGAGAACCCTGGACCTatgaagaggctgctgtgc | 324 |
| 43 | mAL-16D | TGGAGGAGAACCCTGGACCTatgctcctggcactcctc | 325 |
| 44 | mAL-17 | TGGAGGAGAACCCTGGACCTatgttccYagtgaccattctg | 326 |
| 45 | mAL-19 | TGGAGGAGAACCCTGGACCTatgactggcttcctgaaggcc | 327 |
| 46 | mAL-21 | TGGAGGAGAACCCTGGACCTatggcatgtgtgagtggaattgc | 328 |

| No. | Primer Name | Primer Sequence (5' -> 3') | SEQ ID NO. |
|---|---|---|---|
| 1 | mBL-1 | AAGGATCCGAATTCCTGCAGGatgtggcagttttgcattctgtg | 329 |
| 2 | mBL-2 | AAGGATCCGAATTCCTGCAGGatggcctccattttcctcagttgc | 330 |
| 3 | mBL-3 | AAGGATCCGAATTCCTGCAGGatggatatctggcttctaggttgg | 331 |
| 4 | mBL-4 | AAGGATCCGAATTCCTGCAGGatggcctgtaggctcctaag | 332 |
| 5 | mBL-5 | AAGGATCCGAATTCCTGCAGGatgagctgcaggcttctc | 333 |
| 6 | mBL-12-1 | AAGGATCCGAATTCCTGCAGGatgtctaacactgtcctcgctg | 334 |
| 7 | mBL-12-2 | AAGGATCCGAATTCCTGCAGGatgtctaacactgccttccctg | 335 |
| 8 | mBL-13-1 | AAGGATCCGAATTCCTGCAGGatggcctccaggctctttc | 336 |
| 9 | mBL-13-2 | AAGGATCCGAATTCCTGCAGGatggcctccaggctcttctcg | 337 |
| 10 | mBL-13-3 | AAGGATCCGAATTCCTGCAGGatggcctccagactcttcttg | 338 |
| 11 | mBL-14 | AAGGATCCGAATTCCTGCAGGatggcacccaggcttcttg | 339 |
| 12 | mBL-15 | AAGGATCCGAATTCCTGCAGGatggcatccagacccctctg | 340 |
| 13 | mBL-16 | AAGGATCCGAATTCCTGCAGGatggcccccaggctccttttctg | 341 |
| 14 | mBL-17 | AAGGATCCGAATTCCTGCAGGatggatcctagacttctttgctgtg | 342 |
| 15 | mBL-19 | AAGGATCCGAATTCCTGCAGGatgaacaagtgggttttctgc | 343 |
| 16 | mBL-20 | AAGGATCCGAATTCCTGCAGGatgttactgcttctattacttctgg | 344 |
| 17 | mBL-23 | AAGGATCCGAATTCCTGCAGGatggatgcaacggctcatttg | 345 |
| 18 | mBL-24 | AAGGATCCGAATTCCTGCAGGatggKtgcaaggactgctctg | 346 |
| 19 | mBL-26 | AAGGATCCGAATTCCTGCAGGatggctacaaggctcctctgt | 347 |
| 20 | mBL-29 | AAGGATCCGAATTCCTGCAGGatgaagagttagcctcatctctgc | 348 |
| 21 | mBL-30 | AAGGATCCGAATTCCTGCAGGatgtggacattcctgctacttc | 349 |
| 22 | mBL-31 | AAGGATCCGAATTCCTGCAGGatgctgtactctctccttgc | 350 |

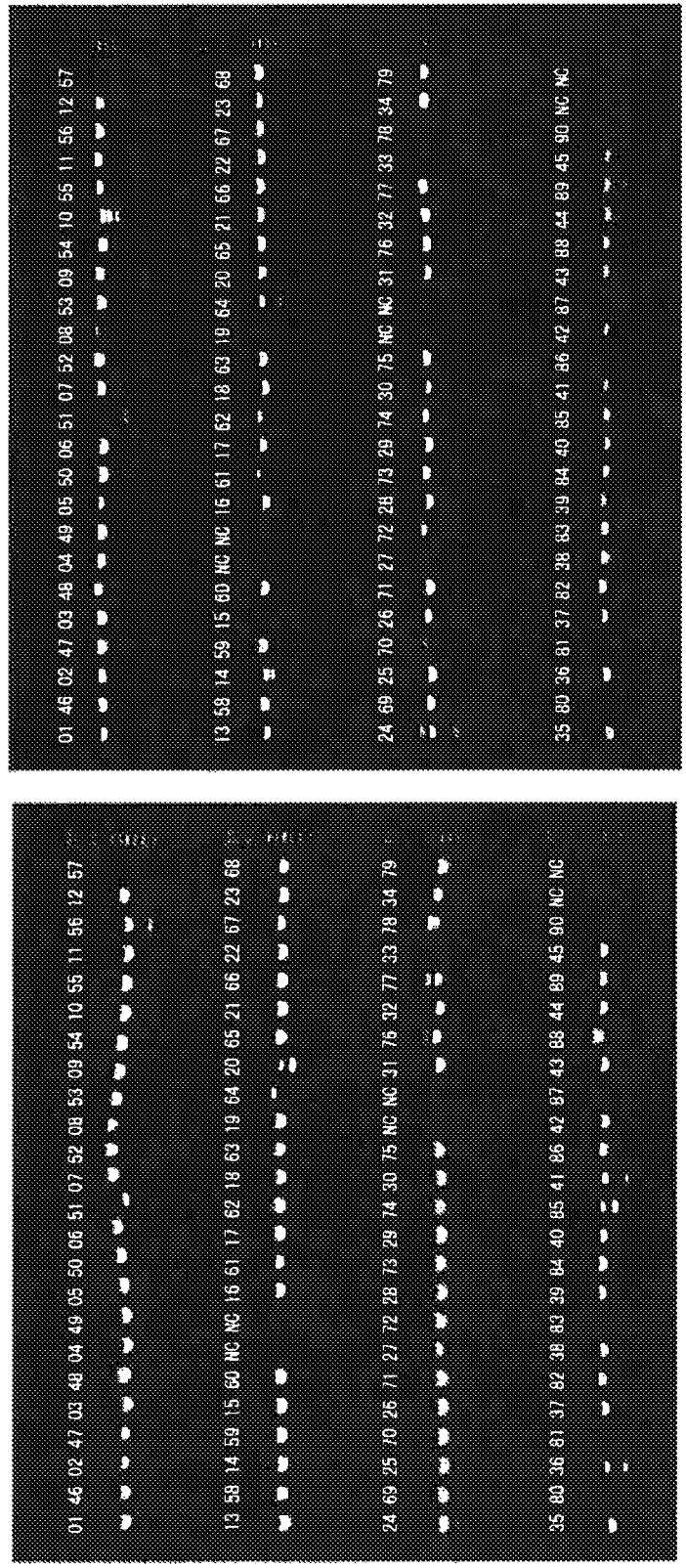
[Fig. 14]

SEQUENCE LISTING

```
<160> NUMBER OF SEQ ID NOS: 355

<210> SEQ ID NO 1
<211> LENGTH: 40
<212> TYPE: DNA
<213> ORGANISM: Artificial Sequence
<220> FEATURE:
<223> OTHER INFORMATION: PCR primer

<400> SEQUENCE: 1
tggaggagaa ccctggacct atgtggggag ctttccttct                           40

<210> SEQ ID NO 2
<211> LENGTH: 40
<212> TYPE: DNA
<213> ORGANISM: Artificial Sequence
<220> FEATURE:
<223> OTHER INFORMATION: PCR primer

<400> SEQUENCE: 2
tggaggagaa ccctggacct atggctttgc agagcactct                           40

<210> SEQ ID NO 3
<211> LENGTH: 40
<212> TYPE: DNA
<213> ORGANISM: Artificial Sequence
```

```
<220> FEATURE:
<223> OTHER INFORMATION: PCR primer

<400> SEQUENCE: 3
tggaggagaa ccctggacct atggcctctg cacccatctc                              40

<210> SEQ ID NO 4
<211> LENGTH: 40
<212> TYPE: DNA
<213> ORGANISM: Artificial Sequence
<220> FEATURE:
<223> OTHER INFORMATION: PCR primer

<400> SEQUENCE: 4
tggaggagaa ccctggacct atgaggcaag tggcgagagt                              40

<210> SEQ ID NO 5
<211> LENGTH: 40
<212> TYPE: DNA
<213> ORGANISM: Artificial Sequence
<220> FEATURE:
<223> OTHER INFORMATION: PCR primer

<400> SEQUENCE: 5
tggaggagaa ccctggacct atgaagacat ttgctggatt                              40

<210> SEQ ID NO 6
<211> LENGTH: 40
<212> TYPE: DNA
<213> ORGANISM: Artificial Sequence
<220> FEATURE:
<223> OTHER INFORMATION: PCR primer

<400> SEQUENCE: 6
tggaggagaa ccctggacct atggagtcat tcctgggagg                              40

<210> SEQ ID NO 7
<211> LENGTH: 40
<212> TYPE: DNA
<213> ORGANISM: Artificial Sequence
<220> FEATURE:
<223> OTHER INFORMATION: PCR primer

<400> SEQUENCE: 7
tggaggagaa ccctggacct atggagaaga tgcggagacc                              40

<210> SEQ ID NO 8
<211> LENGTH: 40
<212> TYPE: DNA
<213> ORGANISM: Artificial Sequence
<220> FEATURE:
<223> OTHER INFORMATION: PCR primer

<400> SEQUENCE: 8
tggaggagaa ccctggacct atgctcctgt tgctcatacc                              40

<210> SEQ ID NO 9
<211> LENGTH: 40
<212> TYPE: DNA
<213> ORGANISM: Artificial Sequence
<220> FEATURE:
<223> OTHER INFORMATION: PCR primer

<400> SEQUENCE: 9
tggaggagaa ccctggacct atgctcctgc tgctcgtccc                              40
```

```
<210> SEQ ID NO 10
<211> LENGTH: 40
<212> TYPE: DNA
<213> ORGANISM: Artificial Sequence
<220> FEATURE:
<223> OTHER INFORMATION: PCR primer

<400> SEQUENCE: 10
tggaggagaa ccctggacct atgctcctgg agcttatccc                              40

<210> SEQ ID NO 11
<211> LENGTH: 40
<212> TYPE: DNA
<213> ORGANISM: Artificial Sequence
<220> FEATURE:
<223> OTHER INFORMATION: PCR primer

<400> SEQUENCE: 11
tggaggagaa ccctggacct atgaattctt ctccaggacc                              40

<210> SEQ ID NO 12
<211> LENGTH: 40
<212> TYPE: DNA
<213> ORGANISM: Artificial Sequence
<220> FEATURE:
<223> OTHER INFORMATION: PCR primer

<400> SEQUENCE: 12
tggaggagaa ccctggacct atgaactatt ctccaggctt                              40

<210> SEQ ID NO 13
<211> LENGTH: 40
<212> TYPE: DNA
<213> ORGANISM: Artificial Sequence
<220> FEATURE:
<223> OTHER INFORMATION: PCR primer

<400> SEQUENCE: 13
tggaggagaa ccctggacct atgaaaaagc atctgacgac                              40

<210> SEQ ID NO 14
<211> LENGTH: 40
<212> TYPE: DNA
<213> ORGANISM: Artificial Sequence
<220> FEATURE:
<223> OTHER INFORMATION: PCR primer

<400> SEQUENCE: 14
tggaggagaa ccctggacct atgatatcct tgagagtttt                              40

<210> SEQ ID NO 15
<211> LENGTH: 40
<212> TYPE: DNA
<213> ORGANISM: Artificial Sequence
<220> FEATURE:
<223> OTHER INFORMATION: PCR primer

<400> SEQUENCE: 15
tggaggagaa ccctggacct atgatgaaat ccttgagagt                              40

<210> SEQ ID NO 16
<211> LENGTH: 40
<212> TYPE: DNA
<213> ORGANISM: Artificial Sequence
<220> FEATURE:
<223> OTHER INFORMATION: PCR primer
```

<400> SEQUENCE: 16
tggaggagaa ccctggacct atgacatcca ttcgagctgt                                40

<210> SEQ ID NO 17
<211> LENGTH: 40
<212> TYPE: DNA
<213> ORGANISM: Artificial Sequence
<220> FEATURE:
<223> OTHER INFORMATION: PCR primer

<400> SEQUENCE: 17
tggaggagaa ccctggacct atggcaggca ttcgagcttt                                40

<210> SEQ ID NO 18
<211> LENGTH: 40
<212> TYPE: DNA
<213> ORGANISM: Artificial Sequence
<220> FEATURE:
<223> OTHER INFORMATION: PCR primer

<400> SEQUENCE: 18
tggaggagaa ccctggacct atgtcacttt ctagcctgct                                40

<210> SEQ ID NO 19
<211> LENGTH: 40
<212> TYPE: DNA
<213> ORGANISM: Artificial Sequence
<220> FEATURE:
<223> OTHER INFORMATION: PCR primer

<400> SEQUENCE: 19
tggaggagaa ccctggacct atgaagccca ccctcatctc                                40

<210> SEQ ID NO 20
<211> LENGTH: 40
<212> TYPE: DNA
<213> ORGANISM: Artificial Sequence
<220> FEATURE:
<223> OTHER INFORMATION: PCR primer

<400> SEQUENCE: 20
tggaggagaa ccctggacct atggaaactc tcctgggagt                                40

<210> SEQ ID NO 21
<211> LENGTH: 40
<212> TYPE: DNA
<213> ORGANISM: Artificial Sequence
<220> FEATURE:
<223> OTHER INFORMATION: PCR primer

<400> SEQUENCE: 21
tggaggagaa ccctggacct atgctgtctg cttcctgctc                                40

<210> SEQ ID NO 22
<211> LENGTH: 40
<212> TYPE: DNA
<213> ORGANISM: Artificial Sequence
<220> FEATURE:
<223> OTHER INFORMATION: PCR primer

<400> SEQUENCE: 22
tggaggagaa ccctggacct atgctgactg ccagcctgtt                                40

<210> SEQ ID NO 23
<211> LENGTH: 40

<212> TYPE: DNA
<213> ORGANISM: Artificial Sequence
<220> FEATURE:
<223> OTHER INFORMATION: PCR primer

<400> SEQUENCE: 23
tggaggagaa ccctggacct atggagaaaa tgttggagtg                             40

<210> SEQ ID NO 24
<211> LENGTH: 40
<212> TYPE: DNA
<213> ORGANISM: Artificial Sequence
<220> FEATURE:
<223> OTHER INFORMATION: PCR primer

<400> SEQUENCE: 24
tggaggagaa ccctggacct atggagaccc tcttgggcct                             40

<210> SEQ ID NO 25
<211> LENGTH: 40
<212> TYPE: DNA
<213> ORGANISM: Artificial Sequence
<220> FEATURE:
<223> OTHER INFORMATION: PCR primer

<400> SEQUENCE: 25
tggaggagaa ccctggacct atgaagagga tattgggagc                             40

<210> SEQ ID NO 26
<211> LENGTH: 40
<212> TYPE: DNA
<213> ORGANISM: Artificial Sequence
<220> FEATURE:
<223> OTHER INFORMATION: PCR primer

<400> SEQUENCE: 26
tggaggagaa ccctggacct atggacaaga tcttaggagc                             40

<210> SEQ ID NO 27
<211> LENGTH: 40
<212> TYPE: DNA
<213> ORGANISM: Artificial Sequence
<220> FEATURE:
<223> OTHER INFORMATION: PCR primer

<400> SEQUENCE: 27
tggaggagaa ccctggacct atggagaaga atcctttggc                             40

<210> SEQ ID NO 28
<211> LENGTH: 40
<212> TYPE: DNA
<213> ORGANISM: Artificial Sequence
<220> FEATURE:
<223> OTHER INFORMATION: PCR primer

<400> SEQUENCE: 28
tggaggagaa ccctggacct atgctactca tcacatcaat                             40

<210> SEQ ID NO 29
<211> LENGTH: 40
<212> TYPE: DNA
<213> ORGANISM: Artificial Sequence
<220> FEATURE:
<223> OTHER INFORMATION: PCR primer

<400> SEQUENCE: 29
tggaggagaa ccctggacct atgaggctgg tggcaagagt                          40

<210> SEQ ID NO 30
<211> LENGTH: 40
<212> TYPE: DNA
<213> ORGANISM: Artificial Sequence
<220> FEATURE:
<223> OTHER INFORMATION: PCR primer

<400> SEQUENCE: 30
tggaggagaa ccctggacct atgaagttgg tgacaagcat                          40

<210> SEQ ID NO 31
<211> LENGTH: 40
<212> TYPE: DNA
<213> ORGANISM: Artificial Sequence
<220> FEATURE:
<223> OTHER INFORMATION: PCR primer

<400> SEQUENCE: 31
tggaggagaa ccctggacct atggtcctga aattctccgt                          40

<210> SEQ ID NO 32
<211> LENGTH: 40
<212> TYPE: DNA
<213> ORGANISM: Artificial Sequence
<220> FEATURE:
<223> OTHER INFORMATION: PCR primer

<400> SEQUENCE: 32
tggaggagaa ccctggacct atggccatgc tcctgggggc                          40

<210> SEQ ID NO 33
<211> LENGTH: 40
<212> TYPE: DNA
<213> ORGANISM: Artificial Sequence
<220> FEATURE:
<223> OTHER INFORMATION: PCR primer

<400> SEQUENCE: 33
tggaggagaa ccctggacct atggagactc tcctgaaagt                          40

<210> SEQ ID NO 34
<211> LENGTH: 40
<212> TYPE: DNA
<213> ORGANISM: Artificial Sequence
<220> FEATURE:
<223> OTHER INFORMATION: PCR primer

<400> SEQUENCE: 34
tggaggagaa ccctggacct atggagactg ttctgcaagt                          40

<210> SEQ ID NO 35
<211> LENGTH: 40
<212> TYPE: DNA
<213> ORGANISM: Artificial Sequence
<220> FEATURE:
<223> OTHER INFORMATION: PCR primer

<400> SEQUENCE: 35
tggaggagaa ccctggacct atgctccttg aacatttatt                          40

<210> SEQ ID NO 36
<211> LENGTH: 40
<212> TYPE: DNA
<213> ORGANISM: Artificial Sequence

```
<220> FEATURE:
<223> OTHER INFORMATION: PCR primer

<400> SEQUENCE: 36
tggaggagaa ccctggacct atgatgaagt gtccacaggc                    40

<210> SEQ ID NO 37
<211> LENGTH: 40
<212> TYPE: DNA
<213> ORGANISM: Artificial Sequence
<220> FEATURE:
<223> OTHER INFORMATION: PCR primer

<400> SEQUENCE: 37
tggaggagaa ccctggacct atgacacgag ttagcttgct                    40

<210> SEQ ID NO 38
<211> LENGTH: 40
<212> TYPE: DNA
<213> ORGANISM: Artificial Sequence
<220> FEATURE:
<223> OTHER INFORMATION: PCR primer

<400> SEQUENCE: 38
tggaggagaa ccctggacct atggcatgcc ctggcttcct                    40

<210> SEQ ID NO 39
<211> LENGTH: 40
<212> TYPE: DNA
<213> ORGANISM: Artificial Sequence
<220> FEATURE:
<223> OTHER INFORMATION: PCR primer

<400> SEQUENCE: 39
tggaggagaa ccctggacct atgaagaagc tactagcaat                    40

<210> SEQ ID NO 40
<211> LENGTH: 40
<212> TYPE: DNA
<213> ORGANISM: Artificial Sequence
<220> FEATURE:
<223> OTHER INFORMATION: PCR primer

<400> SEQUENCE: 40
tggaggagaa ccctggacct atgaactcct ctctggactt                    40

<210> SEQ ID NO 41
<211> LENGTH: 40
<212> TYPE: DNA
<213> ORGANISM: Artificial Sequence
<220> FEATURE:
<223> OTHER INFORMATION: PCR primer

<400> SEQUENCE: 41
tggaggagaa ccctggacct atggtgaaga tccggcaatt                    40

<210> SEQ ID NO 42
<211> LENGTH: 41
<212> TYPE: DNA
<213> ORGANISM: Artificial Sequence
<220> FEATURE:
<223> OTHER INFORMATION: PCR primer

<400> SEQUENCE: 42
aaggatccga attcctgcag gatggatacc tggctcgtat g                  41
```

<210> SEQ ID NO 43
<211> LENGTH: 41
<212> TYPE: DNA
<213> ORGANISM: Artificial Sequence
<220> FEATURE:
<223> OTHER INFORMATION: PCR primer

<400> SEQUENCE: 43
aaggatccga attcctgcag gatgggctgc aggctcctct g                          41

<210> SEQ ID NO 44
<211> LENGTH: 41
<212> TYPE: DNA
<213> ORGANISM: Artificial Sequence
<220> FEATURE:
<223> OTHER INFORMATION: PCR primer

<400> SEQUENCE: 44
aaggatccga attcctgcag gatgggctgc aggctgctct g                          41

<210> SEQ ID NO 45
<211> LENGTH: 41
<212> TYPE: DNA
<213> ORGANISM: Artificial Sequence
<220> FEATURE:
<223> OTHER INFORMATION: PCR primer

<400> SEQUENCE: 45
aaggatccga attcctgcag gatgggctcc aggctgctct g                          41

<210> SEQ ID NO 46
<211> LENGTH: 41
<212> TYPE: DNA
<213> ORGANISM: Artificial Sequence
<220> FEATURE:
<223> OTHER INFORMATION: PCR primer

<400> SEQUENCE: 46
aaggatccga attcctgcag gatgggccct gggctcctct g                          41

<210> SEQ ID NO 47
<211> LENGTH: 41
<212> TYPE: DNA
<213> ORGANISM: Artificial Sequence
<220> FEATURE:
<223> OTHER INFORMATION: PCR primer

<400> SEQUENCE: 47
aaggatccga attcctgcag gatgggcccc gggctcctct g                          41

<210> SEQ ID NO 48
<211> LENGTH: 41
<212> TYPE: DNA
<213> ORGANISM: Artificial Sequence
<220> FEATURE:
<223> OTHER INFORMATION: PCR primer

<400> SEQUENCE: 48
aaggatccga attcctgcag gatgggaccc aggctcctct t                          41

<210> SEQ ID NO 49
<211> LENGTH: 41
<212> TYPE: DNA
<213> ORGANISM: Artificial Sequence
<220> FEATURE:
<223> OTHER INFORMATION: PCR primer

<400> SEQUENCE: 49
aaggatccga attcctgcag gatgagcatc gggctcctgt g                          41

<210> SEQ ID NO 50
<211> LENGTH: 41
<212> TYPE: DNA
<213> ORGANISM: Artificial Sequence
<220> FEATURE:
<223> OTHER INFORMATION: PCR primer

<400> SEQUENCE: 50
aaggatccga attcctgcag gatgagcctc gggctcctgt g                          41

<210> SEQ ID NO 51
<211> LENGTH: 41
<212> TYPE: DNA
<213> ORGANISM: Artificial Sequence
<220> FEATURE:
<223> OTHER INFORMATION: PCR primer

<400> SEQUENCE: 51
aaggatccga attcctgcag gatgagaatc aggctcctgt g                          41

<210> SEQ ID NO 52
<211> LENGTH: 41
<212> TYPE: DNA
<213> ORGANISM: Artificial Sequence
<220> FEATURE:
<223> OTHER INFORMATION: PCR primer

<400> SEQUENCE: 52
aaggatccga attcctgcag gatgagcatc ggcctcctgt g                          41

<210> SEQ ID NO 53
<211> LENGTH: 41
<212> TYPE: DNA
<213> ORGANISM: Artificial Sequence
<220> FEATURE:
<223> OTHER INFORMATION: PCR primer

<400> SEQUENCE: 53
aaggatccga attcctgcag gatgagcatc agcctcctgt g                          41

<210> SEQ ID NO 54
<211> LENGTH: 41
<212> TYPE: DNA
<213> ORGANISM: Artificial Sequence
<220> FEATURE:
<223> OTHER INFORMATION: PCR primer

<400> SEQUENCE: 54
aaggatccga attcctgcag gatgggcacc aggctcctct t                          41

<210> SEQ ID NO 55
<211> LENGTH: 41
<212> TYPE: DNA
<213> ORGANISM: Artificial Sequence
<220> FEATURE:
<223> OTHER INFORMATION: PCR primer

<400> SEQUENCE: 55
aaggatccga attcctgcag gatgggcacc aggctcctct g                          41

<210> SEQ ID NO 56

```
<211> LENGTH: 41
<212> TYPE: DNA
<213> ORGANISM: Artificial Sequence
<220> FEATURE:
<223> OTHER INFORMATION: PCR primer

<400> SEQUENCE: 56
aaggatccga attcctgcag gatgggcacc agtctcctat g          41

<210> SEQ ID NO 57
<211> LENGTH: 41
<212> TYPE: DNA
<213> ORGANISM: Artificial Sequence
<220> FEATURE:
<223> OTHER INFORMATION: PCR primer

<400> SEQUENCE: 57
aaggatccga attcctgcag gatgggtacc agtctcctat g          41

<210> SEQ ID NO 58
<211> LENGTH: 41
<212> TYPE: DNA
<213> ORGANISM: Artificial Sequence
<220> FEATURE:
<223> OTHER INFORMATION: PCR primer

<400> SEQUENCE: 58
aaggatccga attcctgcag gatgggcacc agcctcctct g          41

<210> SEQ ID NO 59
<211> LENGTH: 41
<212> TYPE: DNA
<213> ORGANISM: Artificial Sequence
<220> FEATURE:
<223> OTHER INFORMATION: PCR primer

<400> SEQUENCE: 59
aaggatccga attcctgcag gatgggcttc aggctcctct g          41

<210> SEQ ID NO 60
<211> LENGTH: 41
<212> TYPE: DNA
<213> ORGANISM: Artificial Sequence
<220> FEATURE:
<223> OTHER INFORMATION: PCR primer

<400> SEQUENCE: 60
aaggatccga attcctgcag gatgggcacg aggctcttct t          41

<210> SEQ ID NO 61
<211> LENGTH: 41
<212> TYPE: DNA
<213> ORGANISM: Artificial Sequence
<220> FEATURE:
<223> OTHER INFORMATION: PCR primer

<400> SEQUENCE: 61
aaggatccga attcctgcag gatgggcacc aggctcttct t          41

<210> SEQ ID NO 62
<211> LENGTH: 41
<212> TYPE: DNA
<213> ORGANISM: Artificial Sequence
<220> FEATURE:
<223> OTHER INFORMATION: PCR primer

<400> SEQUENCE: 62
```
aaggatccga attcctgcag gatgggcaca aggttgttct t    41

<210> SEQ ID NO 63
<211> LENGTH: 41
<212> TYPE: DNA
<213> ORGANISM: Artificial Sequence
<220> FEATURE:
<223> OTHER INFORMATION: PCR primer

<400> SEQUENCE: 63
aaggatccga attcctgcag gatgagcacc aggcttctct g    41

<210> SEQ ID NO 64
<211> LENGTH: 41
<212> TYPE: DNA
<213> ORGANISM: Artificial Sequence
<220> FEATURE:
<223> OTHER INFORMATION: PCR primer

<400> SEQUENCE: 64
aaggatccga attcctgcag gatgggtacc aggctcctct g    41

<210> SEQ ID NO 65
<211> LENGTH: 41
<212> TYPE: DNA
<213> ORGANISM: Artificial Sequence
<220> FEATURE:
<223> OTHER INFORMATION: PCR primer

<400> SEQUENCE: 65
aaggatccga attcctgcag gatggactcc tggaccttct g    41

<210> SEQ ID NO 66
<211> LENGTH: 41
<212> TYPE: DNA
<213> ORGANISM: Artificial Sequence
<220> FEATURE:
<223> OTHER INFORMATION: PCR primer

<400> SEQUENCE: 66
aaggatccga attcctgcag gatgggctcc tggaccctct g    41

<210> SEQ ID NO 67
<211> LENGTH: 41
<212> TYPE: DNA
<213> ORGANISM: Artificial Sequence
<220> FEATURE:
<223> OTHER INFORMATION: PCR primer

<400> SEQUENCE: 67
aaggatccga attcctgcag gatggccacc aggctcctct g    41

<210> SEQ ID NO 68
<211> LENGTH: 41
<212> TYPE: DNA
<213> ORGANISM: Artificial Sequence
<220> FEATURE:
<223> OTHER INFORMATION: PCR primer

<400> SEQUENCE: 68
aaggatccga attcctgcag gatgcttagt cctgacctgc c    41

<210> SEQ ID NO 69
<211> LENGTH: 41
<212> TYPE: DNA

```
<213> ORGANISM: Artificial Sequence
<220> FEATURE:
<223> OTHER INFORMATION: PCR primer

<400> SEQUENCE: 69
aaggatccga attcctgcag gatggtttcc aggcttctca g          41

<210> SEQ ID NO 70
<211> LENGTH: 41
<212> TYPE: DNA
<213> ORGANISM: Artificial Sequence
<220> FEATURE:
<223> OTHER INFORMATION: PCR primer

<400> SEQUENCE: 70
aaggatccga attcctgcag gatgggtcct gggcttctcc a          41

<210> SEQ ID NO 71
<211> LENGTH: 41
<212> TYPE: DNA
<213> ORGANISM: Artificial Sequence
<220> FEATURE:
<223> OTHER INFORMATION: PCR primer

<400> SEQUENCE: 71
aaggatccga attcctgcag gatgagccca atattcacct g          41

<210> SEQ ID NO 72
<211> LENGTH: 41
<212> TYPE: DNA
<213> ORGANISM: Artificial Sequence
<220> FEATURE:
<223> OTHER INFORMATION: PCR primer

<400> SEQUENCE: 72
aaggatccga attcctgcag gatggacacc agagtactct g          41

<210> SEQ ID NO 73
<211> LENGTH: 41
<212> TYPE: DNA
<213> ORGANISM: Artificial Sequence
<220> FEATURE:
<223> OTHER INFORMATION: PCR primer

<400> SEQUENCE: 73
aaggatccga attcctgcag gatgagcaac caggtgctct g          41

<210> SEQ ID NO 74
<211> LENGTH: 41
<212> TYPE: DNA
<213> ORGANISM: Artificial Sequence
<220> FEATURE:
<223> OTHER INFORMATION: PCR primer

<400> SEQUENCE: 74
aaggatccga attcctgcag gatgctgctg cttctgctgc t          41

<210> SEQ ID NO 75
<211> LENGTH: 41
<212> TYPE: DNA
<213> ORGANISM: Artificial Sequence
<220> FEATURE:
<223> OTHER INFORMATION: PCR primer

<400> SEQUENCE: 75
aaggatccga attcctgcag gatggcctcc ctgctcttct t          41
```

```
<210> SEQ ID NO 76
<211> LENGTH: 41
<212> TYPE: DNA
<213> ORGANISM: Artificial Sequence
<220> FEATURE:
<223> OTHER INFORMATION: PCR primer

<400> SEQUENCE: 76
aaggatccga attcctgcag gatgactatc aggctcctct g          41

<210> SEQ ID NO 77
<211> LENGTH: 41
<212> TYPE: DNA
<213> ORGANISM: Artificial Sequence
<220> FEATURE:
<223> OTHER INFORMATION: PCR primer

<400> SEQUENCE: 77
aaggatccga attcctgcag gatgggcccc cagctccttg g          41

<210> SEQ ID NO 78
<211> LENGTH: 41
<212> TYPE: DNA
<213> ORGANISM: Artificial Sequence
<220> FEATURE:
<223> OTHER INFORMATION: PCR primer

<400> SEQUENCE: 78
aaggatccga attcctgcag gatgggaatc aggctcctgt g          41

<210> SEQ ID NO 79
<211> LENGTH: 41
<212> TYPE: DNA
<213> ORGANISM: Artificial Sequence
<220> FEATURE:
<223> OTHER INFORMATION: PCR primer

<400> SEQUENCE: 79
aaggatccga attcctgcag gatgctgagt cttctgctcc t          41

<210> SEQ ID NO 80
<211> LENGTH: 41
<212> TYPE: DNA
<213> ORGANISM: Artificial Sequence
<220> FEATURE:
<223> OTHER INFORMATION: PCR primer

<400> SEQUENCE: 80
aaggatccga attcctgcag gatgctctgc tctctccttg c          41

<210> SEQ ID NO 81
<211> LENGTH: 20
<212> TYPE: DNA
<213> ORGANISM: Artificial Sequence
<220> FEATURE:
<223> OTHER INFORMATION: Adapter

<400> SEQUENCE: 81
tggaggagaa ccctggacct          20

<210> SEQ ID NO 82
<211> LENGTH: 21
<212> TYPE: DNA
<213> ORGANISM: Artificial Sequence
<220> FEATURE:
```

<223> OTHER INFORMATION: Adapter

<400> SEQUENCE: 82
aaggatccga attcctgcag g                                            21

<210> SEQ ID NO 83
<211> LENGTH: 24
<212> TYPE: DNA
<213> ORGANISM: Artificial Sequence
<220> FEATURE:
<223> OTHER INFORMATION: PCR primer

<400> SEQUENCE: 83
aggttcgtat ctgtttcaaa gctt                                         24

<210> SEQ ID NO 84
<211> LENGTH: 22
<212> TYPE: DNA
<213> ORGANISM: Artificial Sequence
<220> FEATURE:
<223> OTHER INFORMATION: PCR primer

<400> SEQUENCE: 84
ggtaaagcca cagtctgctc ta                                           22

<210> SEQ ID NO 85
<211> LENGTH: 21
<212> TYPE: DNA
<213> ORGANISM: Artificial Sequence
<220> FEATURE:
<223> OTHER INFORMATION: PCR primer

<400> SEQUENCE: 85
tgtgacacat ttgtttgaga a                                            21

<210> SEQ ID NO 86
<211> LENGTH: 18
<212> TYPE: DNA
<213> ORGANISM: Artificial Sequence
<220> FEATURE:
<223> OTHER INFORMATION: PCR primer

<400> SEQUENCE: 86
ctgtgcacct ccttccca                                                18

<210> SEQ ID NO 87
<211> LENGTH: 103
<212> TYPE: DNA
<213> ORGANISM: Artificial Sequence
<220> FEATURE:
<223> OTHER INFORMATION: PCR primer

<400> SEQUENCE: 87
cagactacag tggctcagga accggggatg cagtgccagg ctcatggtat cctgcagcag      60 atgtgggag ctttccttct ctatgtttcc atgaagatgg gag                       103

<210> SEQ ID NO 88
<211> LENGTH: 103
<212> TYPE: DNA
<213> ORGANISM: Artificial Sequence
<220> FEATURE:
<223> OTHER INFORMATION: PCR primer

<400> SEQUENCE: 88
cgactttgct gccatttatt tctaagaatc tctccttaat ggcaattctt ttgtgaccac      60

```
atgtgggag ttttccttct ttatgtttcc atgaagatgg gag        103
```

<210> SEQ ID NO 89
<211> LENGTH: 124
<212> TYPE: DNA
<213> ORGANISM: Artificial Sequence
<220> FEATURE:
<223> OTHER INFORMATION: PCR primer

<400> SEQUENCE: 89

```
aaaaatgcaa aacaggtagt cttaaataag cattctggtg agaccaactg cattttggcc     60
atggctttgc agagcactct gggggcggtg tggctagggc ttctcctcaa ctctctctgg    120
aagg                                                                 124
```

<210> SEQ ID NO 90
<211> LENGTH: 106
<212> TYPE: DNA
<213> ORGANISM: Artificial Sequence
<220> FEATURE:
<223> OTHER INFORMATION: PCR primer

<400> SEQUENCE: 90

```
agcagaggtg ggctggaaag gacccccca atcccgcccg ccgtgagctt agctggagcc     60
atggcctctg cacccatctc gatgcttgcg atgctcttca cattga                   106
```

<210> SEQ ID NO 91
<211> LENGTH: 100
<212> TYPE: DNA
<213> ORGANISM: Artificial Sequence
<220> FEATURE:
<223> OTHER INFORMATION: PCR primer

<400> SEQUENCE: 91

```
cattgcagct cagacacagc aaaagagcct agaacctggg tcctagtttg cacctagaat     60
atgaggcaag tggcgagagt gatcgtgttc ctgaccctga                          100
```

<210> SEQ ID NO 92
<211> LENGTH: 112
<212> TYPE: DNA
<213> ORGANISM: Artificial Sequence
<220> FEATURE:
<223> OTHER INFORMATION: PCR primer

<400> SEQUENCE: 92

```
agagatactt gataatatag ctctcttggc tggagattgc aggtcccagt ggggagaaca     60
atgaagacat tgctggatt ttcgttcctg tttttgtggc tgcagctgga ct             112
```

<210> SEQ ID NO 93
<211> LENGTH: 112
<212> TYPE: DNA
<213> ORGANISM: Artificial Sequence
<220> FEATURE:
<223> OTHER INFORMATION: PCR primer

<400> SEQUENCE: 93

```
agaatggctt tttggctgag aaggctgggt ctacatttca ggccacattt ggggagacga     60
atggagtcat tcctgggagg tgttttgctg attttgtggc ttcaagtgga ct             112
```

<210> SEQ ID NO 94
<211> LENGTH: 112
<212> TYPE: DNA

```
<213> ORGANISM: Artificial Sequence
<220> FEATURE:
<223> OTHER INFORMATION: PCR primer

<400> SEQUENCE: 94
aagctttgtt tggctacata attttatgca gcatttttgg tatcaagaca aagtatcagg      60
atggagaaga tgcggagacc tgtcctaatt atattttgtc tatgtcttgg ct             112

<210> SEQ ID NO 95
<211> LENGTH: 106
<212> TYPE: DNA
<213> ORGANISM: Artificial Sequence
<220> FEATURE:
<223> OTHER INFORMATION: PCR primer

<400> SEQUENCE: 95
tcctactggc cccgaggaga atttccaaag agacgcctgc agtgtttcca cagctcagcc      60
atgctcctgt tgctcatacc agtgctgggg atgattttg ccctga                     106

<210> SEQ ID NO 96
<211> LENGTH: 106
<212> TYPE: DNA
<213> ORGANISM: Artificial Sequence
<220> FEATURE:
<223> OTHER INFORMATION: PCR primer

<400> SEQUENCE: 96 caggaccct ggcttctgtc ctccctgctc agggtcctgc agcgttgcct ctgctcagcc       60
atgctcctgc tgctcgtccc agtgctcgag gtgatttta ctctgg                     106

<210> SEQ ID NO 97
<211> LENGTH: 106
<212> TYPE: DNA
<213> ORGANISM: Artificial Sequence
<220> FEATURE:
<223> OTHER INFORMATION: PCR primer

<400> SEQUENCE: 97
tccttcctgt tctctggaga tcttgcagaa aagagcctgc agtgtttccc ttgttcagcc      60
atgctcctgg agcttatccc actgctgggg atacattttg tcctga                    106

<210> SEQ ID NO 98
<211> LENGTH: 106
<212> TYPE: DNA
<213> ORGANISM: Artificial Sequence
<220> FEATURE:
<223> OTHER INFORMATION: PCR primer

<400> SEQUENCE: 98 cagggcccctt ggcttctgtc cgctctgctc agggccctcc agcgtggcca ctgctcagcc     60
atgctcctgc tgctcgtccc agtgctcgag gtgattttta ccctgg                    106

<210> SEQ ID NO 99
<211> LENGTH: 110
<212> TYPE: DNA
<213> ORGANISM: Artificial Sequence
<220> FEATURE:
<223> OTHER INFORMATION: PCR primer

<400> SEQUENCE: 99
tccttcctgt tctctggaga tcttgcagaa aagagcctgc agtgtttcca ttgctcagcc      60
atgctcctgg tgctcatccc actgctgggg atacattttg tcctgagtga                110
```

<210> SEQ ID NO 100
<211> LENGTH: 106
<212> TYPE: DNA
<213> ORGANISM: Artificial Sequence
<220> FEATURE:
<223> OTHER INFORMATION: PCR primer

<400> SEQUENCE: 100
cagcgccctt ggcttctgtc cgcccagctc aaggtcctgc agcattgcca ctgctcagcc    60
atgctcctgc tgctcgtccc agcgttccag gtgattttta ccctgg                  106

<210> SEQ ID NO 101
<211> LENGTH: 106
<212> TYPE: DNA
<213> ORGANISM: Artificial Sequence
<220> FEATURE:
<223> OTHER INFORMATION: PCR primer

<400> SEQUENCE: 101
attccttccc actcaggaga tcttctagaa tagagctctc agcttcctca ctgcctagcc    60
atgctcttag tggtcattct gctgcttgga atgttcttca cactga                  106

<210> SEQ ID NO 102
<211> LENGTH: 106
<212> TYPE: DNA
<213> ORGANISM: Artificial Sequence
<220> FEATURE:
<223> OTHER INFORMATION: PCR primer

<400> SEQUENCE: 102
tgaccttaac ttttcctcac actaagaaga caagacccaa gggcaccaga gggtctaaaa    60
atgaattctt ctccaggacc agcgattgca ctattcttaa tgtttg                  106

<210> SEQ ID NO 103
<211> LENGTH: 106
<212> TYPE: DNA
<213> ORGANISM: Artificial Sequence
<220> FEATURE:
<223> OTHER INFORMATION: PCR primer

<400> SEQUENCE: 103
gtttcactgt gatttcttca tgttaaggat caagaccatt atttgggtaa cacactaaag    60
atgaactatt ctccaggctt agtatctctg atactcttac tgcttg                  106

<210> SEQ ID NO 104
<211> LENGTH: 112
<212> TYPE: DNA
<213> ORGANISM: Artificial Sequence
<220> FEATURE:
<223> OTHER INFORMATION: PCR primer

<400> SEQUENCE: 104
aaaagagaag atgttgaata cacaagtcaa cttctgggag cagatctctg cagaataaaa    60
atgaaaaagc atctgacgac cttcttggtg attttgtggc tttatttta ta            112

<210> SEQ ID NO 105
<211> LENGTH: 112
<212> TYPE: DNA
<213> ORGANISM: Artificial Sequence
<220> FEATURE:
<223> OTHER INFORMATION: PCR primer

<400> SEQUENCE: 105
gatagtgttt gagggctccc agacccagc cagagacctc actgagtcta agtgataaaa    60
acggagaagc ccttgggagt ttcattcttg atttcctcct ggcagctgtg ct          112

<210> SEQ ID NO 106
<211> LENGTH: 109
<212> TYPE: DNA
<213> ORGANISM: Artificial Sequence
<220> FEATURE:
<223> OTHER INFORMATION: PCR primer

<400> SEQUENCE: 106
tgttcatttc ttttggatt gaaaatttta atcctcagtg aaccagggca gaaaagaatg    60
atgatatcct tgagagtttt actggtgatc ctgtggcttc agttaagct               109

<210> SEQ ID NO 107
<211> LENGTH: 109
<212> TYPE: DNA
<213> ORGANISM: Artificial Sequence
<220> FEATURE:
<223> OTHER INFORMATION: PCR primer

<400> SEQUENCE: 107
aggtgcattt tttaagggtt taaaatttga atcctcagtg aaccagggca gagaagaatg    60
atgaaatcct tgagagtttt actagtgatc ctgtggcttc agttgagct                109

<210> SEQ ID NO 108
<211> LENGTH: 112
<212> TYPE: DNA
<213> ORGANISM: Artificial Sequence
<220> FEATURE:
<223> OTHER INFORMATION: PCR primer

<400> SEQUENCE: 108
tgttattatt ttttttcgt gtttaaggtt tgaatcctca gtgaaccagg gcagaaaaga    60
atgatgaaat ccttgagagt tttactggtg atcctgtggc ttcagttaag ct           112

<210> SEQ ID NO 109
<211> LENGTH: 109
<212> TYPE: DNA
<213> ORGANISM: Artificial Sequence
<220> FEATURE:
<223> OTHER INFORMATION: PCR primer

<400> SEQUENCE: 109
agtaactctt ataactggag gttgcaggtc aatgactgat cttaattggg aagaacaagg    60
atgacatcca ttcgagctgt atttatattc ctgtggctgc agctggact              109

<210> SEQ ID NO 110
<211> LENGTH: 109
<212> TYPE: DNA
<213> ORGANISM: Artificial Sequence
<220> FEATURE:
<223> OTHER INFORMATION: PCR primer

<400> SEQUENCE: 110
agtagctctt atggctggag attgcaggtt tatgactgat cctatttggg aagaacaatg    60
atggcaggca ttcgagcttt atttatgtac ttgtggctgc agctggact              109

<210> SEQ ID NO 111
<211> LENGTH: 109

-continued

```
<212> TYPE: DNA
<213> ORGANISM: Artificial Sequence
<220> FEATURE:
<223> OTHER INFORMATION: PCR primer

<400> SEQUENCE: 111
cagtacagag tcctgaaaat aaagaagaag attttttttt atctagaaaa ggaaccaaac    60
atgtcacttt ctagcctgct gaaggtggtc acagcttcac tgtggctag              109

<210> SEQ ID NO 112
<211> LENGTH: 110
<212> TYPE: DNA
<213> ORGANISM: Artificial Sequence
<220> FEATURE:
<223> OTHER INFORMATION: PCR primer

<400> SEQUENCE: 112
cattaggaga tatacctaat gtaaatgact agttaatggg tgcagacacc aacatggcgc    60
atgtatacgt atgtaacaaa cctgcgcgtt gtgcacatgt accctagaac              110

<210> SEQ ID NO 113
<211> LENGTH: 106
<212> TYPE: DNA
<213> ORGANISM: Artificial Sequence
<220> FEATURE:
<223> OTHER INFORMATION: PCR primer

<400> SEQUENCE: 113
ctgaatcgtt tccagaaaag acctccagaa aatagcttcc tgtttctcca caggtcagac    60
atgaagccca ccctcatctc agtgcttgtg ataatattta tactca                 106

<210> SEQ ID NO 114
<211> LENGTH: 112
<212> TYPE: DNA
<213> ORGANISM: Artificial Sequence
<220> FEATURE:
<223> OTHER INFORMATION: PCR primer

<400> SEQUENCE: 114
tctgtgactg aggagccttg ctccatttca ggtcttctgt gatttcaata aggaagaaga    60
atggaaactc tcctgggagt gtctttggtg attctatggc ttcaactggc ta           112

<210> SEQ ID NO 115
<211> LENGTH: 106
<212> TYPE: DNA
<213> ORGANISM: Artificial Sequence
<220> FEATURE:
<223> OTHER INFORMATION: PCR primer

<400> SEQUENCE: 115
atatatacct ttcggtttgg atatctctca acaaaacctt ctactgcttc tcagccagcc    60
atgctgtctg cttcctgctc aggacttgtg atcttgttga tattca                 106

<210> SEQ ID NO 116
<211> LENGTH: 109
<212> TYPE: DNA
<213> ORGANISM: Artificial Sequence
<220> FEATURE:
<223> OTHER INFORMATION: PCR primer

<400> SEQUENCE: 116
attaagatct ggatttgaga cggagcacgg aacatttcac tcaggggaag agctatgaac    60
```

```
atgctgactg ccagcctgtt gagggcagtc atagcctcca tctgtgttg            109
```

<210> SEQ ID NO 117
<211> LENGTH: 112
<212> TYPE: DNA
<213> ORGANISM: Artificial Sequence
<220> FEATURE:
<223> OTHER INFORMATION: PCR primer

<400> SEQUENCE: 117

```
gcgcctctga gaaagaagg ttggaattat cgtaatttgt ttctaggctg agataccagc   60
atggagaaaa tgttggagtg tgcattcata gtcttgtggc ttcagcttgg ct          112
```

<210> SEQ ID NO 118
<211> LENGTH: 106
<212> TYPE: DNA
<213> ORGANISM: Artificial Sequence
<220> FEATURE:
<223> OTHER INFORMATION: PCR primer

<400> SEQUENCE: 118

```
ccattctcca tatttcagat ataagatttc agttctcagt gagtctaagt gacagaagga   60
atggagaccc tcttgggcct gcttatcctt tggctgcagc tgcaat                 106
```

<210> SEQ ID NO 119
<211> LENGTH: 112
<212> TYPE: DNA
<213> ORGANISM: Artificial Sequence
<220> FEATURE:
<223> OTHER INFORMATION: PCR primer

<400> SEQUENCE: 119

```
ccaaggttta gttaaatata tcttatggtg aaaatgcccg gagcaagaag gcaaagcatc   60
atgaagagga tattgggagc tctgctgggg ctcttgagtg cccaggtttg ct          112
```

<210> SEQ ID NO 120
<211> LENGTH: 112
<212> TYPE: DNA
<213> ORGANISM: Artificial Sequence
<220> FEATURE:
<223> OTHER INFORMATION: PCR primer

<400> SEQUENCE: 120

```
agctggttgg gaagactgga agaccacctg gctgtcatt gagctctggt gccaggagga    60
atggacaaga tcttaggagc atcatttta gttctgtggc ttcaactatg ct           112
```

<210> SEQ ID NO 121
<211> LENGTH: 115
<212> TYPE: DNA
<213> ORGANISM: Artificial Sequence
<220> FEATURE:
<223> OTHER INFORMATION: PCR primer

<400> SEQUENCE: 121

```
atatttccac agattttggc tgaaaaacgt ttttctgctg tgggtacgtg agcaggaaac   60
atggagaaga atcctttggc agccccatta ctaatcctct ggtttcatct tgact       115
```

<210> SEQ ID NO 122
<211> LENGTH: 106
<212> TYPE: DNA
<213> ORGANISM: Artificial Sequence
<220> FEATURE:
<223> OTHER INFORMATION: PCR primer

<400> SEQUENCE: 122
tggaagaagc ttgtaccagg caacccattt aggagaagtt ggatgaagag ggagagggag      60
atgctactca tcacatcaat gttggtctta tggatgcaat tgtcac      106

<210> SEQ ID NO 123
<211> LENGTH: 100
<212> TYPE: DNA
<213> ORGANISM: Artificial Sequence
<220> FEATURE:
<223> OTHER INFORMATION: PCR primer

<400> SEQUENCE: 123
acctagaatc agacacaaaa actgaactct gggtccacaa tcctcatttg tccttgaagt      60
atgaggctgg tggcaagagt aactgtgttt ctgacctttg      100

<210> SEQ ID NO 124
<211> LENGTH: 100
<212> TYPE: DNA
<213> ORGANISM: Artificial Sequence
<220> FEATURE:
<223> OTHER INFORMATION: PCR primer

<400> SEQUENCE: 124
cctaggatca gacacagagt ctgagttctg gggcctggaa cctcaatgtg cacttgaaca      60
atgaagttgg tgacaagcat tactgtactc ctatctttgg      100

<210> SEQ ID NO 125
<211> LENGTH: 106
<212> TYPE: DNA
<213> ORGANISM: Artificial Sequence
<220> FEATURE:
<223> OTHER INFORMATION: PCR primer

<400> SEQUENCE: 125
gggctctttc aggagcagct aaagtcaggg gccatgtcca ccatgtgata gaaagacaag      60
atggtcctga aattctccgt gtccattctt tggattcagt tggcat      106

<210> SEQ ID NO 126
<211> LENGTH: 112
<212> TYPE: DNA
<213> ORGANISM: Artificial Sequence
<220> FEATURE:
<223> OTHER INFORMATION: PCR primer

<400> SEQUENCE: 126
ccaatattta aagagaatag atatcaaggt gtgcccctgt agcaaaaaaa gtaaagaatc      60
atgaaggcat taataggaat cttgctgggc ttcctgtgga tacagatttg ct      112

<210> SEQ ID NO 127
<211> LENGTH: 112
<212> TYPE: DNA
<213> ORGANISM: Artificial Sequence
<220> FEATURE:
<223> OTHER INFORMATION: PCR primer

<400> SEQUENCE: 127
gaagtcagat ttgcagcttt ctaggcagga gacaagacaa tctgcatctt cacaggaggg      60
atggccatgc tcctgggggc atcagtgctg attctgtggc ttcagccaga ct      112

<210> SEQ ID NO 128

```
<211> LENGTH: 112
<212> TYPE: DNA
<213> ORGANISM: Artificial Sequence
<220> FEATURE:
<223> OTHER INFORMATION: PCR primer

<400> SEQUENCE: 128
aagcaactcc tgttaaggaa gcccattcag aagctgactg gatattctgg caggccaagg      60
atggagactc tcctgaaagt gctttcaggc accttgttgt ggcagttgac ct             112

<210> SEQ ID NO 129
<211> LENGTH: 109
<212> TYPE: DNA
<213> ORGANISM: Artificial Sequence
<220> FEATURE:
<223> OTHER INFORMATION: PCR primer

<400> SEQUENCE: 129
ataaagtagg tctcaggctc tgagcaggca gttttttttc ctagaaatag aggtgccaac      60
atgactgttg gcagcatatt acgggcactc atggcctctg ccttccttg                 109

<210> SEQ ID NO 130
<211> LENGTH: 114
<212> TYPE: DNA
<213> ORGANISM: Artificial Sequence
<220> FEATURE:
<223> OTHER INFORMATION: PCR primer

<400> SEQUENCE: 130
aatacactga gaatagaata tgttctcctt cccagatagt atagatcatt gatgattcta      60
atggcaagaa gaatggaaaa gtccctggga gctttattca aattcagctg aagc            114

<210> SEQ ID NO 131
<211> LENGTH: 109
<212> TYPE: DNA
<213> ORGANISM: Artificial Sequence
<220> FEATURE:
<223> OTHER INFORMATION: PCR primer

<400> SEQUENCE: 131
gcattttgtt tccaggcttg agtgaggaag caaatttcaa ccgtaagaag aaattctacc      60
atgctctgcc ctggcctgct gtgggcattc gtggtcccct ttggcttca                 109

<210> SEQ ID NO 132
<211> LENGTH: 112
<212> TYPE: DNA
<213> ORGANISM: Artificial Sequence
<220> FEATURE:
<223> OTHER INFORMATION: PCR primer

<400> SEQUENCE: 132
ctgctgggga agctcattca gtaaaatctg atttaactgt gttttctaaa tagctaaggg      60
atggagactg ttctgcaagt actcctaggg atattggggt tccaagcagc ct             112

<210> SEQ ID NO 133
<211> LENGTH: 106
<212> TYPE: DNA
<213> ORGANISM: Artificial Sequence
<220> FEATURE:
<223> OTHER INFORMATION: PCR primer

<400> SEQUENCE: 133
tcttgaagca aaaaaaaaaa aaaaaaaacc cattcaggaa ataattcttt gctgataagg      60
```

```
atgctccttg aacatttatt aataatcttg tggatgcagc tgacat               106
```

<210> SEQ ID NO 134
<211> LENGTH: 112
<212> TYPE: DNA
<213> ORGANISM: Artificial Sequence
<220> FEATURE:
<223> OTHER INFORMATION: PCR primer

<400> SEQUENCE: 134

```
gaaacgctta aaggtagtga atcacgtttt gcccaggaaa acacacttga taactgaagg    60
atgatgaagt gtccacaggc tttactagct atcttttggc ttctactgag ct           112
```

<210> SEQ ID NO 135
<211> LENGTH: 112
<212> TYPE: DNA
<213> ORGANISM: Artificial Sequence
<220> FEATURE:
<223> OTHER INFORMATION: PCR primer

<400> SEQUENCE: 135

```
gaacacggcc aaatctaggt ctccaaactg aatccacaga ggctccagga aaaggaaaga    60
atggaaactc cactgagcac tctgctgctg ctcctctgtg tgcagctgac ct           112
```

<210> SEQ ID NO 136
<211> LENGTH: 109
<212> TYPE: DNA
<213> ORGANISM: Artificial Sequence
<220> FEATURE:
<223> OTHER INFORMATION: PCR primer

<400> SEQUENCE: 136

```
gcacagagga gaacccatca gagcaggaga cttttcactc tgcaggggag cgctgtcagc    60
atgacacgag ttagcttgct gtgggcagtc gtggtctcca cctgtcttg              109
```

<210> SEQ ID NO 137
<211> LENGTH: 109
<212> TYPE: DNA
<213> ORGANISM: Artificial Sequence
<220> FEATURE:
<223> OTHER INFORMATION: PCR primer

<400> SEQUENCE: 137

```
gatactcaag gttcagatca gaagaggagg cttctcaccc tgcagcaggg acctgtgagc    60
atggcatgcc ctggcttcct gtgggcactt gtgatctcca cctgtcttg              109
```

<210> SEQ ID NO 138
<211> LENGTH: 103
<212> TYPE: DNA
<213> ORGANISM: Artificial Sequence
<220> FEATURE:
<223> OTHER INFORMATION: PCR primer

<400> SEQUENCE: 138

```
cctggccaac tttcaaggct cctaaatctg agttttcagt gaactggaca gaaaaaaaaa    60
atgaagaagc tactagcaat gattctgtgg cttcaactag acc                    103
```

<210> SEQ ID NO 139
<211> LENGTH: 103
<212> TYPE: DNA
<213> ORGANISM: Artificial Sequence
<220> FEATURE:

<223> OTHER INFORMATION: PCR primer

<400> SEQUENCE: 139

```
gtacaactgt gaatcctcac ttcaacagtg atgccctctg ctaggccaga gacactaaca      60
atgaactcct ctctggactt tctaattctg atcttaatgt ttg                       103
```

<210> SEQ ID NO 140
<211> LENGTH: 112
<212> TYPE: DNA
<213> ORGANISM: Artificial Sequence
<220> FEATURE:
<223> OTHER INFORMATION: PCR primer

<400> SEQUENCE: 140

```
tccaagatat attccgaaat cctccaacag agacctgtgt gagcttctgc tgcagtaata      60
atggtgaaga tccggcaatt tttgttggct attttgtggc ttcagctaag ct             112
```

<210> SEQ ID NO 141
<211> LENGTH: 109
<212> TYPE: DNA
<213> ORGANISM: Artificial Sequence
<220> FEATURE:
<223> OTHER INFORMATION: PCR primer

<400> SEQUENCE: 141

```
ttcctccaca ggaccagatg cctgagctag gaaaggcctc attcctgctg tgatcctgcc      60
atggatacct ggctcgtatg ctgggcaatt tttagtctct tgaaagcag                 109
```

<210> SEQ ID NO 142
<211> LENGTH: 109
<212> TYPE: DNA
<213> ORGANISM: Artificial Sequence
<220> FEATURE:
<223> OTHER INFORMATION: PCR primer

<400> SEQUENCE: 142

```
ctctcaccac tgcagaccag aatcctgccc tgggccttgc ctggtctgcc tcactctgcc      60
atgggctgca ggctcctctg ctgtgtggtc ttctgcctcc tccaagcag                 109
```

<210> SEQ ID NO 143
<211> LENGTH: 109
<212> TYPE: DNA
<213> ORGANISM: Artificial Sequence
<220> FEATURE:
<223> OTHER INFORMATION: PCR primer

<400> SEQUENCE: 143

```
agcccagcac ctcgcccaaa ggaccccagt cagaggcccc atctcagacc cgaggctagc      60
atgggctgca ggctgctctg ctgtgcggtt ctctgtctcc tgggagcag                 109
```

<210> SEQ ID NO 144
<211> LENGTH: 109
<212> TYPE: DNA
<213> ORGANISM: Artificial Sequence
<220> FEATURE:
<223> OTHER INFORMATION: PCR primer

<400> SEQUENCE: 144

```
agcccagcac ctcacccaga ggaccccagt cagaggcccc atctcagacc cgaggctagc      60
atgggctgca ggctgctctg ctgtgcggtt ctctgtctcc tgggagcgg                 109
```

-continued

```
<210> SEQ ID NO 145
<211> LENGTH: 118
<212> TYPE: DNA
<213> ORGANISM: Artificial Sequence
<220> FEATURE:
<223> OTHER INFORMATION: PCR primer

<400> SEQUENCE: 145
agcccagcac ctcacccaga ggaccccagt cagaggcccc atctcagacc cgaggctagc      60
atgggctgca ggctgctctg ctgtgcggtt ctctgtctcc tgggagcggg tgagttgg       118

<210> SEQ ID NO 146
<211> LENGTH: 109
<212> TYPE: DNA
<213> ORGANISM: Artificial Sequence
<220> FEATURE:
<223> OTHER INFORMATION: PCR primer

<400> SEQUENCE: 146
ctctttccca ggaggaccaa gccctgagca cagacacagt gctgcctgcc cctttgtgcc      60
atgggctcca ggctgctctg ttgggtgctg ctttgtctcc tgggagcag               109

<210> SEQ ID NO 147
<211> LENGTH: 109
<212> TYPE: DNA
<213> ORGANISM: Artificial Sequence
<220> FEATURE:
<223> OTHER INFORMATION: PCR primer

<400> SEQUENCE: 147
gctcttcccc aggaggacca agccctgaat caggtgcagt gctgcctgcc ccactgtgcc      60
atgggccctg ggctcctctg ctgggtgctg ctttgtctcc tgggagcag               109

<210> SEQ ID NO 148
<211> LENGTH: 109
<212> TYPE: DNA
<213> ORGANISM: Artificial Sequence
<220> FEATURE:
<223> OTHER INFORMATION: PCR primer

<400> SEQUENCE: 148
gttcttcccc aggaggacca agccctgaat caggtgcagt gctgcctgcc ccactgtgcc      60
atgggccctg ggctcctctg ctgggtgctg ctttgtctcc tgggagcag               109

<210> SEQ ID NO 149
<211> LENGTH: 109
<212> TYPE: DNA
<213> ORGANISM: Artificial Sequence
<220> FEATURE:
<223> OTHER INFORMATION: PCR primer

<400> SEQUENCE: 149
gctcttcccc aggagaacca agccctgaat cagatgcagt gcttcctgtc cctctgtgcc      60
atgggccccg ggctcctctg ctgggcactg ctttgtctcc tgggagcag               109

<210> SEQ ID NO 150
<211> LENGTH: 109
<212> TYPE: DNA
<213> ORGANISM: Artificial Sequence
<220> FEATURE:
<223> OTHER INFORMATION: PCR primer

<400> SEQUENCE: 150
```

-continued gctcttcccc aggaagacca agccctgaat caggtgcagt gccgcctggc ccactgtgcc    60
atgggaccca ggctcctctt ctgggcactg ctttgtctcc tcggaacag               109

<210> SEQ ID NO 151
<211> LENGTH: 109
<212> TYPE: DNA
<213> ORGANISM: Artificial Sequence
<220> FEATURE:
<223> OTHER INFORMATION: PCR primer

<400> SEQUENCE: 151
cctgttcccc tatcaccgat gcacagaccc agaagacccc tccatcctgt agcacctgcc    60
atgagcatcg ggctcctgtg ctgtgtggcc ttttctctcc tgtgggcaa               109

<210> SEQ ID NO 152
<211> LENGTH: 109
<212> TYPE: DNA
<213> ORGANISM: Artificial Sequence
<220> FEATURE:
<223> OTHER INFORMATION: PCR primer

<400> SEQUENCE: 152
cgtgttccct tttcaccaat gcacagaccc agaggacccc tccatcctgc agttcctgcc    60
atgagcctcg ggctcctgtg ctgtggggcc ttttctctcc tgtgggcag               109

<210> SEQ ID NO 153
<211> LENGTH: 109
<212> TYPE: DNA
<213> ORGANISM: Artificial Sequence
<220> FEATURE:
<223> OTHER INFORMATION: PCR primer

<400> SEQUENCE: 153
cgtgttccct tttcaccaat gcacagaccc agaggacccc tccatcctgc agttcctgcc    60
atgagcctcg ggctcctgtg ctgtggggcc ttttctctcc tgtgggcag               109

<210> SEQ ID NO 154
<211> LENGTH: 109
<212> TYPE: DNA
<213> ORGANISM: Artificial Sequence
<220> FEATURE:
<223> OTHER INFORMATION: PCR primer

<400> SEQUENCE: 154
cctgttcgcc tttcatcaac acacagaccc agaagacctc tctgtcttgt agcatctgcc    60
atgagaatca ggctcctgtg ctgtgtggcc ttttctctcc tgtgggcag               109

<210> SEQ ID NO 155
<211> LENGTH: 109
<212> TYPE: DNA
<213> ORGANISM: Artificial Sequence
<220> FEATURE:
<223> OTHER INFORMATION: PCR primer

<400> SEQUENCE: 155
cctgctcccc tttcatcaat gcacagatac agaagacccc tccgtcatgc agcatctgcc    60
atgagcatcg gcctcctgtg ctgtgcagcc ttgtctctcc tgtgggcag               109

<210> SEQ ID NO 156
<211> LENGTH: 109
<212> TYPE: DNA
<213> ORGANISM: Artificial Sequence
<220> FEATURE:
<223> OTHER INFORMATION: PCR primer

<400> SEQUENCE: 156
cctgttcccc tttcatcaat gcacagatac agaagacccc tccgtcctgg agcacctgcc    60
atgagcatca gcctcctgtg ctgtgcagcc tttcctctcc tgtgggcag              109

<210> SEQ ID NO 157
<211> LENGTH: 109
<212> TYPE: DNA
<213> ORGANISM: Artificial Sequence
<220> FEATURE:
<223> OTHER INFORMATION: PCR primer

<400> SEQUENCE: 157
cctgttcccc ttttatcaat gcacagaccc agaagacccc tccgtcctgc agcccctgcc    60
atgagcctcg ggctcctgtg ctgtgcggcc ttttctctcc tgtgggcag              109

<210> SEQ ID NO 158
<211> LENGTH: 109
<212> TYPE: DNA
<213> ORGANISM: Artificial Sequence
<220> FEATURE:
<223> OTHER INFORMATION: PCR primer

<400> SEQUENCE: 158
cctgttcccc tttcatcaat gcacagaccc agaagacccc tacgtcctgc agcccctgcc    60
atgagcatcg ggctcctgtg ctgtgtggcc ttttctctcc tgtgggagg              109

<210> SEQ ID NO 159
<211> LENGTH: 109
<212> TYPE: DNA
<213> ORGANISM: Artificial Sequence
<220> FEATURE:
<223> OTHER INFORMATION: PCR primer

<400> SEQUENCE: 159
tctgctcctg ctcacagtga tcctgatctg gtaaagctcc catcctgccc tgaccctgcc    60
atgggcacca ggctcctctt ctgggtggcc ttctgtctcc tggggcag              109

<210> SEQ ID NO 160
<211> LENGTH: 109
<212> TYPE: DNA
<213> ORGANISM: Artificial Sequence
<220> FEATURE:
<223> OTHER INFORMATION: PCR primer

<400> SEQUENCE: 160
tctgctcctg ctcacagtga ccctgatctg gtaaagctcc catcctgccc tgactctgtc    60
atgggcacca ggctcctctg ctgggcagcc ctgtgcctcc tggggcag              109

<210> SEQ ID NO 161
<211> LENGTH: 109
<212> TYPE: DNA
<213> ORGANISM: Artificial Sequence
<220> FEATURE:
<223> OTHER INFORMATION: PCR primer

<400> SEQUENCE: 161
tctgctcctg ctcatagtga cactgacctg gtaaaacccc cgtcctggcc tgaccctgcc    60
atgggcacca ggctcctctg ctgggtggtc ctgggtttcc tagggacag              109

```
<210> SEQ ID NO 162
<211> LENGTH: 109
<212> TYPE: DNA
<213> ORGANISM: Artificial Sequence
<220> FEATURE:
<223> OTHER INFORMATION: PCR primer

<400> SEQUENCE: 162
tctgctgctg ctcacagtga cactgatctg gtaaagccct catcctgtcc tgaccctgcc      60
atgggcacca gtctcctatg ctgggtggtc ctgggtttcc tagggacag                 109

<210> SEQ ID NO 163
<211> LENGTH: 109
<212> TYPE: DNA
<213> ORGANISM: Artificial Sequence
<220> FEATURE:
<223> OTHER INFORMATION: PCR primer

<400> SEQUENCE: 163
tccgctcctg ctcacagtga cactgatctg gtaaagcccc catcctggtc tgacactgtc      60
atgggtacca gtctcctatg ctgggtggtc ctgggtttcc tagggacag                 109

<210> SEQ ID NO 164
<211> LENGTH: 109
<212> TYPE: DNA
<213> ORGANISM: Artificial Sequence
<220> FEATURE:
<223> OTHER INFORMATION: PCR primer

<400> SEQUENCE: 164
tctgctcctg ctcacagtga cactgatctg gtaaagcccc catcctggcc tgaccctgcc      60
atgggcacca ggctcctctg ctgggtggtc ctgggtttcc tagggacag                 109

<210> SEQ ID NO 165
<211> LENGTH: 109
<212> TYPE: DNA
<213> ORGANISM: Artificial Sequence
<220> FEATURE:
<223> OTHER INFORMATION: PCR primer

<400> SEQUENCE: 165
tctgctcctg ctcacagtga ccctgatctg gtaaagctcc catcctgccc tgaccctgcc      60
atgggcacca gcctcctctg ctggatggcc ctgtgtctcc tgggggcag                 109

<210> SEQ ID NO 166
<211> LENGTH: 109
<212> TYPE: DNA
<213> ORGANISM: Artificial Sequence
<220> FEATURE:
<223> OTHER INFORMATION: PCR primer

<400> SEQUENCE: 166
gcttaggaac ttcagaatgc ttactacaga gacaccagcc ccaagctagg agatcctgcc      60
atgggcttca ggctcctctg ctgtgtggcc ttttgtctcc tgggagcag                 109

<210> SEQ ID NO 167
<211> LENGTH: 109
<212> TYPE: DNA
<213> ORGANISM: Artificial Sequence
<220> FEATURE:
<223> OTHER INFORMATION: PCR primer

<400> SEQUENCE: 167
```

```
cccaacttca gtctgcccac agcagggctg ggagacacaa gatcctgccc tggagctgaa      60
atgggcacga ggctcttctt ctatgtggcc ctttgtctgc tgtgggcag                 109
```

<210> SEQ ID NO 168
<211> LENGTH: 109
<212> TYPE: DNA
<213> ORGANISM: Artificial Sequence
<220> FEATURE:
<223> OTHER INFORMATION: PCR primer

<400> SEQUENCE: 168

```
ctcaacttca atttgcccac agcagggctg ggagacacaa gatcctgccc tggagctgaa      60
atgggcacca ggctcttctt ctatgtggcc ctttgtctgc tgtgggcag                 109
```

<210> SEQ ID NO 169
<211> LENGTH: 109
<212> TYPE: DNA
<213> ORGANISM: Artificial Sequence
<220> FEATURE:
<223> OTHER INFORMATION: PCR primer

<400> SEQUENCE: 169

```
acctaagttc tatttcccca ggcagggctg ggagagatga gatcctggcc tggacctgaa      60
atgggcacaa ggttgttctt ctatgtggcc ctttgtctcc tgtggacag                 109
```

<210> SEQ ID NO 170
<211> LENGTH: 109
<212> TYPE: DNA
<213> ORGANISM: Artificial Sequence
<220> FEATURE:
<223> OTHER INFORMATION: PCR primer

<400> SEQUENCE: 170

```
tctgctcctg ttcacaagga ccctgaactg gcaaagctcc catcctgccc tgaccctgcc      60
atgagcacca ggcttctctg ctggatggcc ctctgtctcc tggggcag                  109
```

<210> SEQ ID NO 171
<211> LENGTH: 109
<212> TYPE: DNA
<213> ORGANISM: Artificial Sequence
<220> FEATURE:
<223> OTHER INFORMATION: PCR primer

<400> SEQUENCE: 171

```
tctgcttttg ctcacagtga ccctgattgg gcaaagctcc catccttccc tgaccctgcc      60
atgggcacca ggctcctctg ctgggcggcc ctctgtctcc tgggagcag                 109
```

<210> SEQ ID NO 172
<211> LENGTH: 109
<212> TYPE: DNA
<213> ORGANISM: Artificial Sequence
<220> FEATURE:
<223> OTHER INFORMATION: PCR primer

<400> SEQUENCE: 172

```
tctgctcctg ctcacagtga ccctgatctg gcaaagcttc catcctgccc tgaccctgcc      60
atgggtacca ggctcctctg ctgggtggcc ttctgtctcc tggtggaag                 109
```

<210> SEQ ID NO 173
<211> LENGTH: 109
<212> TYPE: DNA

<210> SEQ ID NO 174
<211> LENGTH: 109
<212> TYPE: DNA
<213> ORGANISM: Artificial Sequence
<220> FEATURE:
<223> OTHER INFORMATION: PCR primer

<400> SEQUENCE: 173
ctttgctcat gctcacagag ggcctggtct agaatattcc acatctgctc tcactctgcc    60
atggactcct ggaccttctg ctgtgtgtcc ctttgcatcc tggtagcga                109

<210> SEQ ID NO 174
<211> LENGTH: 109
<212> TYPE: DNA
<213> ORGANISM: Artificial Sequence
<220> FEATURE:
<223> OTHER INFORMATION: PCR primer

<400> SEQUENCE: 174
ctttgctcat gttcacagag ggcctggtct ggaatattcc acatctgctc tcactctgcc    60
atgggctcct ggaccctctg ctgtgtgtcc ctttgcatcc tggtagcaa                109

<210> SEQ ID NO 175
<211> LENGTH: 109
<212> TYPE: DNA
<213> ORGANISM: Artificial Sequence
<220> FEATURE:
<223> OTHER INFORMATION: PCR primer

<400> SEQUENCE: 175
cctgtattcg tgcccacaag ggcctcatct aggtgaaggc tccacctgcc ccaccctgcc    60
atggccacca ggctcctctg ctgtgtggtt ctttgtctcc tgggagaag                109

<210> SEQ ID NO 176
<211> LENGTH: 139
<212> TYPE: DNA
<213> ORGANISM: Artificial Sequence
<220> FEATURE:
<223> OTHER INFORMATION: PCR primer

<400> SEQUENCE: 176
gtgaggagga gcaaaagccc tgctttctca ccccaggaga ccagcaacct gagcagggag    60
atgcttagtc ctgacctgcc tgactctgcc tggaacacca ggctcctctg ccatgtcatg   120
ctttgtctcc tgggagcag                                                139

<210> SEQ ID NO 177
<211> LENGTH: 109
<212> TYPE: DNA
<213> ORGANISM: Artificial Sequence
<220> FEATURE:
<223> OTHER INFORMATION: PCR primer

<400> SEQUENCE: 177 tccttttct catacttgta agctccttca tctggaaatg tgatttacct gggtcctgcc     60
atggtttcca ggcttctcag tttagtgtcc ctttgtctcc tgggagcaa                109

<210> SEQ ID NO 178
<211> LENGTH: 109
<212> TYPE: DNA
<213> ORGANISM: Artificial Sequence
<220> FEATURE:
<223> OTHER INFORMATION: PCR primer

<400> SEQUENCE: 178
caggaatcag agcctgagac agacagatgc ttcattcctg tatggggtgg tattcctgcc    60
atgggtcctg ggcttctcca ctggatggcc ctttgtctcc ttggaacag        109

<210> SEQ ID NO 179
<211> LENGTH: 109
<212> TYPE: DNA
<213> ORGANISM: Artificial Sequence
<220> FEATURE:
<223> OTHER INFORMATION: PCR primer

<400> SEQUENCE: 179
tggagagagc cacacagata gccagctgcc tgtgctgcct gctcttcccc taattctgcc        60
atgagcccaa tattcacctg catcacaatc ctttgtctgc tggctgcag        109

<210> SEQ ID NO 180
<211> LENGTH: 109
<212> TYPE: DNA
<213> ORGANISM: Artificial Sequence
<220> FEATURE:
<223> OTHER INFORMATION: PCR primer

<400> SEQUENCE: 180
gacgtgctgc agcaagtgcc tttgccctgc ctgtgggctc cctccatggc caactctgct        60
atggacacca gagtactctg ctgtgcggtc atctgtcttc tgggggcag        109

<210> SEQ ID NO 181
<211> LENGTH: 109
<212> TYPE: DNA
<213> ORGANISM: Artificial Sequence
<220> FEATURE:
<223> OTHER INFORMATION: PCR primer

<400> SEQUENCE: 181
tctcttttct cattctcttc caacaagtgc ttggagctcc aagaaggccc cctttgcact        60
atgagcaacc aggtgctctg ctgtgtggtc ctttgtttcc tgggagcaa        109

<210> SEQ ID NO 182
<211> LENGTH: 121
<212> TYPE: DNA
<213> ORGANISM: Artificial Sequence
<220> FEATURE:
<223> OTHER INFORMATION: PCR primer

<400> SEQUENCE: 182
tgaatggagg cagtggtcac aactctcccc agagaaggtg gtgtgaggcc atcacggaag        60
atgctgctgc ttctgctgct tctggggcca ggtataagcc tccttctacc tgggagcttg        120
g        121

<210> SEQ ID NO 183
<211> LENGTH: 109
<212> TYPE: DNA
<213> ORGANISM: Artificial Sequence
<220> FEATURE:
<223> OTHER INFORMATION: PCR primer

<400> SEQUENCE: 183
catgccctgc ttccctcaac atccagagct ggaaacacct ccatcctgcc tcttcatgcc        60
atggcctccc tgctcttctt ctgtggggcc ttttatctcc tgggaacag        109

<210> SEQ ID NO 184
<211> LENGTH: 109
<212> TYPE: DNA

```
<213> ORGANISM: Artificial Sequence
<220> FEATURE:
<223> OTHER INFORMATION: PCR primer

<400> SEQUENCE: 184
tcaagagccc atcctgcttc cccactactg ggagacatcc tctctagccc caactgtgcc    60
atgactatca ggctcctctg ctacatgggc ttttattttc tggggcag                109

<210> SEQ ID NO 185
<211> LENGTH: 109
<212> TYPE: DNA
<213> ORGANISM: Artificial Sequence
<220> FEATURE:
<223> OTHER INFORMATION: PCR primer

<400> SEQUENCE: 185
gagacgttac agaaaccacc tggagccccc agaactggca gacacctgcc tgatgctgcc    60
atgggccccc agctccttgg ctatgtggtc ctttgccttc taggagcag                109

<210> SEQ ID NO 186
<211> LENGTH: 109
<212> TYPE: DNA
<213> ORGANISM: Artificial Sequence
<220> FEATURE:
<223> OTHER INFORMATION: PCR primer

<400> SEQUENCE: 186
acagaccatc aacccactgc ctggtcctgg gagaagacct attctttctt caaagcagcc    60
atgggaatca ggctcctgtg tcgtgtggcc ttttgtttcc tggctgtag                109

<210> SEQ ID NO 187
<211> LENGTH: 94
<212> TYPE: DNA
<213> ORGANISM: Artificial Sequence
<220> FEATURE:
<223> OTHER INFORMATION: PCR primer

<400> SEQUENCE: 187
agatgaactt gagtttcact tcttagtgcc ttttctcagg ggagaggcca tcacttgaag    60
atgctgagtc ttctgctcct tctcctggga ctag                                94

<210> SEQ ID NO 188
<211> LENGTH: 103
<212> TYPE: DNA
<213> ORGANISM: Artificial Sequence
<220> FEATURE:
<223> OTHER INFORMATION: PCR primer

<400> SEQUENCE: 188
tggcccagaa gaggaggcgt ctgtccccca gactagctga aggaaaggct ggcttggatg    60
atgctctgct ctctccttgc ccttctcctg ggcactttct ttg                      103

<210> SEQ ID NO 189
<211> LENGTH: 23
<212> TYPE: DNA
<213> ORGANISM: Artificial Sequence
<220> FEATURE:
<223> OTHER INFORMATION: PCR primer

<400> SEQUENCE: 189
tccatgaaga tgggaggcac tgc                                            23
```

```
<210> SEQ ID NO 190
<211> LENGTH: 24
<212> TYPE: DNA
<213> ORGANISM: Artificial Sequence
<220> FEATURE:
<223> OTHER INFORMATION: PCR primer

<400> SEQUENCE: 190
ttccatgaag atgggaggca ctac                                              24

<210> SEQ ID NO 191
<211> LENGTH: 24
<212> TYPE: DNA
<213> ORGANISM: Artificial Sequence
<220> FEATURE:
<223> OTHER INFORMATION: PCR primer

<400> SEQUENCE: 191
ctctggaagg ttgcagaaag caag                                              24

<210> SEQ ID NO 192
<211> LENGTH: 24
<212> TYPE: DNA
<213> ORGANISM: Artificial Sequence
<220> FEATURE:
<223> OTHER INFORMATION: PCR primer

<400> SEQUENCE: 192
gctcttcaca ttgagtgggc tgag                                              24

<210> SEQ ID NO 193
<211> LENGTH: 24
<212> TYPE: DNA
<213> ORGANISM: Artificial Sequence
<220> FEATURE:
<223> OTHER INFORMATION: PCR primer

<400> SEQUENCE: 193
ttcctgaccc tgagtacttt gagc                                              24

<210> SEQ ID NO 194
<211> LENGTH: 24
<212> TYPE: DNA
<213> ORGANISM: Artificial Sequence
<220> FEATURE:
<223> OTHER INFORMATION: PCR primer

<400> SEQUENCE: 194
gctgcagctg gactgtatga gtag                                              24

<210> SEQ ID NO 195
<211> LENGTH: 23
<212> TYPE: DNA
<213> ORGANISM: Artificial Sequence
<220> FEATURE:
<223> OTHER INFORMATION: PCR primer

<400> SEQUENCE: 195
ggcttcaagt ggactgggtg aag                                               23

<210> SEQ ID NO 196
<211> LENGTH: 24
<212> TYPE: DNA
<213> ORGANISM: Artificial Sequence
<220> FEATURE:
<223> OTHER INFORMATION: PCR primer
```

```
<400> SEQUENCE: 196
tctatgtctt ggctgggcaa atgg                                          24

<210> SEQ ID NO 197
<211> LENGTH: 24
<212> TYPE: DNA
<213> ORGANISM: Artificial Sequence
<220> FEATURE:
<223> OTHER INFORMATION: PCR primer

<400> SEQUENCE: 197
gatttttgcc ctgagagatg ccag                                          24

<210> SEQ ID NO 198
<211> LENGTH: 25
<212> TYPE: DNA
<213> ORGANISM: Artificial Sequence
<220> FEATURE:
<223> OTHER INFORMATION: PCR primer

<400> SEQUENCE: 198 tgattttac tctgggagga accag                                          25

<210> SEQ ID NO 199
<211> LENGTH: 25
<212> TYPE: DNA
<213> ORGANISM: Artificial Sequence
<220> FEATURE:
<223> OTHER INFORMATION: PCR primer

<400> SEQUENCE: 199
tacattttgt cctgagaact gccag                                         25

<210> SEQ ID NO 200
<211> LENGTH: 24
<212> TYPE: DNA
<213> ORGANISM: Artificial Sequence
<220> FEATURE:
<223> OTHER INFORMATION: PCR primer

<400> SEQUENCE: 200 gattttacc ctgggaggaa ccag                                           24

<210> SEQ ID NO 201
<211> LENGTH: 24
<212> TYPE: DNA
<213> ORGANISM: Artificial Sequence
<220> FEATURE:
<223> OTHER INFORMATION: PCR primer

<400> SEQUENCE: 201
gttcttcaca ctgagaggaa ccag                                          24

<210> SEQ ID NO 202
<211> LENGTH: 27
<212> TYPE: DNA
<213> ORGANISM: Artificial Sequence
<220> FEATURE:
<223> OTHER INFORMATION: PCR primer

<400> SEQUENCE: 202
tattcttaat gtttggggga atcaatg                                       27

<210> SEQ ID NO 203
<211> LENGTH: 24
```

<212> TYPE: DNA
<213> ORGANISM: Artificial Sequence
<220> FEATURE:
<223> OTHER INFORMATION: PCR primer

<400> SEQUENCE: 203
actcttactg cttggaagaa cccg                                      24

<210> SEQ ID NO 204
<211> LENGTH: 26
<212> TYPE: DNA
<213> ORGANISM: Artificial Sequence
<220> FEATURE:
<223> OTHER INFORMATION: PCR primer

<400> SEQUENCE: 204
ggctttattt ttatagggggg aatggc                                   26

<210> SEQ ID NO 205
<211> LENGTH: 24
<212> TYPE: DNA
<213> ORGANISM: Artificial Sequence
<220> FEATURE:
<223> OTHER INFORMATION: PCR primer

<400> SEQUENCE: 205
ttcagttaag ctgggtttgg agcc                                      24

<210> SEQ ID NO 206
<211> LENGTH: 23
<212> TYPE: DNA
<213> ORGANISM: Artificial Sequence
<220> FEATURE:
<223> OTHER INFORMATION: PCR primer

<400> SEQUENCE: 206
tcagttgagc tgggtttgga gcc                                       23

<210> SEQ ID NO 207
<211> LENGTH: 24
<212> TYPE: DNA
<213> ORGANISM: Artificial Sequence
<220> FEATURE:
<223> OTHER INFORMATION: PCR primer

<400> SEQUENCE: 207
ttcagttaag ctgggtttgg agcc                                      24

<210> SEQ ID NO 208
<211> LENGTH: 23
<212> TYPE: DNA
<213> ORGANISM: Artificial Sequence
<220> FEATURE:
<223> OTHER INFORMATION: PCR primer

<400> SEQUENCE: 208
gctgcagctg gacttggtga atg                                       23

<210> SEQ ID NO 209
<211> LENGTH: 22
<212> TYPE: DNA
<213> ORGANISM: Artificial Sequence
<220> FEATURE:
<223> OTHER INFORMATION: PCR primer

<400> SEQUENCE: 209
tgcagctgga ctgggtgagc ag                                          22

<210> SEQ ID NO 210
<211> LENGTH: 23
<212> TYPE: DNA
<213> ORGANISM: Artificial Sequence
<220> FEATURE:
<223> OTHER INFORMATION: PCR primer

<400> SEQUENCE: 210
actgtggcta ggacctggca ttg                                         23

<210> SEQ ID NO 211
<211> LENGTH: 28
<212> TYPE: DNA
<213> ORGANISM: Artificial Sequence
<220> FEATURE:
<223> OTHER INFORMATION: PCR primer

<400> SEQUENCE: 211
tgataatatt tatactcaga ggaacaag                                    28

<210> SEQ ID NO 212
<211> LENGTH: 23
<212> TYPE: DNA
<213> ORGANISM: Artificial Sequence
<220> FEATURE:
<223> OTHER INFORMATION: PCR primer

<400> SEQUENCE: 212
ggcttcaact ggctagggtg aac                                         23

<210> SEQ ID NO 213
<211> LENGTH: 26
<212> TYPE: DNA
<213> ORGANISM: Artificial Sequence
<220> FEATURE:
<223> OTHER INFORMATION: PCR primer

<400> SEQUENCE: 213
atcttgttga tattcagaag gaccag                                      26

<210> SEQ ID NO 214
<211> LENGTH: 25
<212> TYPE: DNA
<213> ORGANISM: Artificial Sequence
<220> FEATURE:
<223> OTHER INFORMATION: PCR primer

<400> SEQUENCE: 214
ctccatctgt gttgtatcca gcatg                                       25

<210> SEQ ID NO 215
<211> LENGTH: 23
<212> TYPE: DNA
<213> ORGANISM: Artificial Sequence
<220> FEATURE:
<223> OTHER INFORMATION: PCR primer

<400> SEQUENCE: 215
cttcagcttg gctggttgag tgg                                         23

<210> SEQ ID NO 216
<211> LENGTH: 22
<212> TYPE: DNA
<213> ORGANISM: Artificial Sequence

```
<220> FEATURE:
<223> OTHER INFORMATION: PCR primer

<400> SEQUENCE: 216
gcagctgcaa tgggtgagca gc                                    22

<210> SEQ ID NO 217
<211> LENGTH: 23
<212> TYPE: DNA
<213> ORGANISM: Artificial Sequence
<220> FEATURE:
<223> OTHER INFORMATION: PCR primer

<400> SEQUENCE: 217
agtgcccagg tttgctgtgt gag                                   23

<210> SEQ ID NO 218
<211> LENGTH: 24
<212> TYPE: DNA
<213> ORGANISM: Artificial Sequence
<220> FEATURE:
<223> OTHER INFORMATION: PCR primer

<400> SEQUENCE: 218
gtggcttcaa ctatgctggg tgag                                  24

<210> SEQ ID NO 219
<211> LENGTH: 24
<212> TYPE: DNA
<213> ORGANISM: Artificial Sequence
<220> FEATURE:
<223> OTHER INFORMATION: PCR primer

<400> SEQUENCE: 219
tttcatcttg actgcgtgag cagc                                  24

<210> SEQ ID NO 220
<211> LENGTH: 26
<212> TYPE: DNA
<213> ORGANISM: Artificial Sequence
<220> FEATURE:
<223> OTHER INFORMATION: PCR primer

<400> SEQUENCE: 220
tatggatgca attgtcacag gtgaat                                26

<210> SEQ ID NO 221
<211> LENGTH: 28
<212> TYPE: DNA
<213> ORGANISM: Artificial Sequence
<220> FEATURE:
<223> OTHER INFORMATION: PCR primer

<400> SEQUENCE: 221
gtgtttctga cctttggaac tataattg                              28

<210> SEQ ID NO 222
<211> LENGTH: 26
<212> TYPE: DNA
<213> ORGANISM: Artificial Sequence
<220> FEATURE:
<223> OTHER INFORMATION: PCR primer

<400> SEQUENCE: 222
gtactcctat ctttgggtat tatggg                                26
```

<210> SEQ ID NO 223
<211> LENGTH: 23
<212> TYPE: DNA
<213> ORGANISM: Artificial Sequence
<220> FEATURE:
<223> OTHER INFORMATION: PCR primer

<400> SEQUENCE: 223
ggattcagtt ggcatgggtg agc                                          23

<210> SEQ ID NO 224
<211> LENGTH: 26
<212> TYPE: DNA
<213> ORGANISM: Artificial Sequence
<220> FEATURE:
<223> OTHER INFORMATION: PCR primer

<400> SEQUENCE: 224
ctgggtaaac agtcaacaga agaatg                                       26

<210> SEQ ID NO 225
<211> LENGTH: 23
<212> TYPE: DNA
<213> ORGANISM: Artificial Sequence
<220> FEATURE:
<223> OTHER INFORMATION: PCR primer

<400> SEQUENCE: 225
ggcagttgac ctgggtgaga agc                                          23

<210> SEQ ID NO 226
<211> LENGTH: 22
<212> TYPE: DNA
<213> ORGANISM: Artificial Sequence
<220> FEATURE:
<223> OTHER INFORMATION: PCR primer

<400> SEQUENCE: 226
ggttccaagc agcctgggtc ag                                           22

<210> SEQ ID NO 227
<211> LENGTH: 23
<212> TYPE: DNA
<213> ORGANISM: Artificial Sequence
<220> FEATURE:
<223> OTHER INFORMATION: PCR primer

<400> SEQUENCE: 227
tggatgcagc tgacatgggt cag                                          23

<210> SEQ ID NO 228
<211> LENGTH: 23
<212> TYPE: DNA
<213> ORGANISM: Artificial Sequence
<220> FEATURE:
<223> OTHER INFORMATION: PCR primer

<400> SEQUENCE: 228
cttctactga gctgggtgag cag                                          23

<210> SEQ ID NO 229
<211> LENGTH: 23
<212> TYPE: DNA
<213> ORGANISM: Artificial Sequence
<220> FEATURE:
<223> OTHER INFORMATION: PCR primer

```
<400> SEQUENCE: 229
ccacctgtct tgaatccggc atg                                              23

<210> SEQ ID NO 230
<211> LENGTH: 25
<212> TYPE: DNA
<213> ORGANISM: Artificial Sequence
<220> FEATURE:
<223> OTHER INFORMATION: PCR primer

<400> SEQUENCE: 230
ctccacctgt cttgaattta gcatg                                            25

<210> SEQ ID NO 231
<211> LENGTH: 24
<212> TYPE: DNA
<213> ORGANISM: Artificial Sequence
<220> FEATURE:
<223> OTHER INFORMATION: PCR primer

<400> SEQUENCE: 231
gcttcaacta gaccggttaa gtgg                                             24

<210> SEQ ID NO 232
<211> LENGTH: 25
<212> TYPE: DNA
<213> ORGANISM: Artificial Sequence
<220> FEATURE:
<223> OTHER INFORMATION: PCR primer

<400> SEQUENCE: 232
gatcttaatg tttggaggaa ccagc                                            25

<210> SEQ ID NO 233
<211> LENGTH: 23
<212> TYPE: DNA
<213> ORGANISM: Artificial Sequence
<220> FEATURE:
<223> OTHER INFORMATION: PCR primer

<400> SEQUENCE: 233
agctaagctg tgtaagtgcc gcc                                              23

<210> SEQ ID NO 234
<211> LENGTH: 25
<212> TYPE: DNA
<213> ORGANISM: Artificial Sequence
<220> FEATURE:
<223> OTHER INFORMATION: PCR primer

<400> SEQUENCE: 234
ttagtctctt gaaagcagga ctcac                                            25

<210> SEQ ID NO 235
<211> LENGTH: 22
<212> TYPE: DNA
<213> ORGANISM: Artificial Sequence
<220> FEATURE:
<223> OTHER INFORMATION: PCR primer

<400> SEQUENCE: 235
cctcctccaa gcaggtccct tg                                               22

<210> SEQ ID NO 236
```

<211> LENGTH: 23
<212> TYPE: DNA
<213> ORGANISM: Artificial Sequence
<220> FEATURE:
<223> OTHER INFORMATION: PCR primer

<400> SEQUENCE: 236
tctcctggga gcagttccca tag                                          23

<210> SEQ ID NO 237
<211> LENGTH: 21
<212> TYPE: DNA
<213> ORGANISM: Artificial Sequence
<220> FEATURE:
<223> OTHER INFORMATION: PCR primer

<400> SEQUENCE: 237
ctcctgggag cggtccccat g                                            21

<210> SEQ ID NO 238
<211> LENGTH: 21
<212> TYPE: DNA
<213> ORGANISM: Artificial Sequence
<220> FEATURE:
<223> OTHER INFORMATION: PCR primer

<400> SEQUENCE: 238
gtctcctggg agcaggccca g                                            21

<210> SEQ ID NO 239
<211> LENGTH: 21
<212> TYPE: DNA
<213> ORGANISM: Artificial Sequence
<220> FEATURE:
<223> OTHER INFORMATION: PCR primer

<400> SEQUENCE: 239
ctcctgggag caggcccagt g                                            21

<210> SEQ ID NO 240
<211> LENGTH: 22
<212> TYPE: DNA
<213> ORGANISM: Artificial Sequence
<220> FEATURE:
<223> OTHER INFORMATION: PCR primer

<400> SEQUENCE: 240
tctcctggga gcaggctcag tg                                           22

<210> SEQ ID NO 241
<211> LENGTH: 21
<212> TYPE: DNA
<213> ORGANISM: Artificial Sequence
<220> FEATURE:
<223> OTHER INFORMATION: PCR primer

<400> SEQUENCE: 241
ctcctgggag caggcccagt g                                            21

<210> SEQ ID NO 242
<211> LENGTH: 23
<212> TYPE: DNA
<213> ORGANISM: Artificial Sequence
<220> FEATURE:
<223> OTHER INFORMATION: PCR primer

<400> SEQUENCE: 242
gtctcctggg agcaggctta gtg                                             23

<210> SEQ ID NO 243
<211> LENGTH: 22
<212> TYPE: DNA
<213> ORGANISM: Artificial Sequence
<220> FEATURE:
<223> OTHER INFORMATION: PCR primer

<400> SEQUENCE: 243
tcccctagga gaaggcccag tg                                              22

<210> SEQ ID NO 244
<211> LENGTH: 22
<212> TYPE: DNA
<213> ORGANISM: Artificial Sequence
<220> FEATURE:
<223> OTHER INFORMATION: PCR primer

<400> SEQUENCE: 244
tctcctcgga acaggcccag tg                                              22

<210> SEQ ID NO 245
<211> LENGTH: 23
<212> TYPE: DNA
<213> ORGANISM: Artificial Sequence
<220> FEATURE:
<223> OTHER INFORMATION: PCR primer

<400> SEQUENCE: 245
ctctcctgtg ggcaagtcca gtg                                             23

<210> SEQ ID NO 246
<211> LENGTH: 22
<212> TYPE: DNA
<213> ORGANISM: Artificial Sequence
<220> FEATURE:
<223> OTHER INFORMATION: PCR primer

<400> SEQUENCE: 246
tctcctgtgg gcaggtccag tg                                              22

<210> SEQ ID NO 247
<211> LENGTH: 23
<212> TYPE: DNA
<213> ORGANISM: Artificial Sequence
<220> FEATURE:
<223> OTHER INFORMATION: PCR primer

<400> SEQUENCE: 247
ctctcctgtg ggcaggtcca atg                                             23

<210> SEQ ID NO 248
<211> LENGTH: 21
<212> TYPE: DNA
<213> ORGANISM: Artificial Sequence
<220> FEATURE:
<223> OTHER INFORMATION: PCR primer

<400> SEQUENCE: 248
ctcctgtggg caggtcccgt g                                               21

<210> SEQ ID NO 249
<211> LENGTH: 22
<212> TYPE: DNA

```
<213> ORGANISM: Artificial Sequence
<220> FEATURE:
<223> OTHER INFORMATION: PCR primer

<400> SEQUENCE: 249
gtctcctggg ggcagatcac ac                                              22

<210> SEQ ID NO 250
<211> LENGTH: 22
<212> TYPE: DNA
<213> ORGANISM: Artificial Sequence
<220> FEATURE:
<223> OTHER INFORMATION: PCR primer

<400> SEQUENCE: 250
gcctcctggg ggcagatcac ac                                              22

<210> SEQ ID NO 251
<211> LENGTH: 24
<212> TYPE: DNA
<213> ORGANISM: Artificial Sequence
<220> FEATURE:
<223> OTHER INFORMATION: PCR primer

<400> SEQUENCE: 251
gggtttccta gggacagatc acac                                            24

<210> SEQ ID NO 252
<211> LENGTH: 22
<212> TYPE: DNA
<213> ORGANISM: Artificial Sequence
<220> FEATURE:
<223> OTHER INFORMATION: PCR primer

<400> SEQUENCE: 252
gtctcctggg ggcagatcac gc                                              22

<210> SEQ ID NO 253
<211> LENGTH: 21
<212> TYPE: DNA
<213> ORGANISM: Artificial Sequence
<220> FEATURE:
<223> OTHER INFORMATION: PCR primer

<400> SEQUENCE: 253
ctcctgggag caggcccagt g                                               21

<210> SEQ ID NO 254
<211> LENGTH: 22
<212> TYPE: DNA
<213> ORGANISM: Artificial Sequence
<220> FEATURE:
<223> OTHER INFORMATION: PCR primer

<400> SEQUENCE: 254
tctgctgtgg gcaggacaca gg                                              22

<210> SEQ ID NO 255
<211> LENGTH: 23
<212> TYPE: DNA
<213> ORGANISM: Artificial Sequence
<220> FEATURE:
<223> OTHER INFORMATION: PCR primer

<400> SEQUENCE: 255
gtctcctgtg gacaggacac atg                                             23
```

<210> SEQ ID NO 256
<211> LENGTH: 22
<212> TYPE: DNA
<213> ORGANISM: Artificial Sequence
<220> FEATURE:
<223> OTHER INFORMATION: PCR primer

<400> SEQUENCE: 256
gtctcctggg ggcagaactc tc                                              22

<210> SEQ ID NO 257
<211> LENGTH: 23
<212> TYPE: DNA
<213> ORGANISM: Artificial Sequence
<220> FEATURE:
<223> OTHER INFORMATION: PCR primer

<400> SEQUENCE: 257
tgtctcctgg gagcagaact cac                                             23

<210> SEQ ID NO 258
<211> LENGTH: 24
<212> TYPE: DNA
<213> ORGANISM: Artificial Sequence
<220> FEATURE:
<223> OTHER INFORMATION: PCR primer

<400> SEQUENCE: 258
gtctcctggt ggaagaactc atag                                            24

<210> SEQ ID NO 259
<211> LENGTH: 24
<212> TYPE: DNA
<213> ORGANISM: Artificial Sequence
<220> FEATURE:
<223> OTHER INFORMATION: PCR primer

<400> SEQUENCE: 259
ttgcatcctg gtagcgaagc atac                                            24

<210> SEQ ID NO 260
<211> LENGTH: 24
<212> TYPE: DNA
<213> ORGANISM: Artificial Sequence
<220> FEATURE:
<223> OTHER INFORMATION: PCR primer

<400> SEQUENCE: 260
ttgcatcctg gtagcaaagc acac                                            24

<210> SEQ ID NO 261
<211> LENGTH: 24
<212> TYPE: DNA
<213> ORGANISM: Artificial Sequence
<220> FEATURE:
<223> OTHER INFORMATION: PCR primer

<400> SEQUENCE: 261
gtctcctggg agaagagctt atag                                            24

<210> SEQ ID NO 262
<211> LENGTH: 23
<212> TYPE: DNA
<213> ORGANISM: Artificial Sequence
<220> FEATURE:

<223> OTHER INFORMATION: PCR primer

<400> SEQUENCE: 262
gtctcctggg agcagtttca gtg                                              23

<210> SEQ ID NO 263
<211> LENGTH: 24
<212> TYPE: DNA
<213> ORGANISM: Artificial Sequence
<220> FEATURE:
<223> OTHER INFORMATION: PCR primer

<400> SEQUENCE: 263
gtctcctggg agcaaagcac atag                                             24

<210> SEQ ID NO 264
<211> LENGTH: 23
<212> TYPE: DNA
<213> ORGANISM: Artificial Sequence
<220> FEATURE:
<223> OTHER INFORMATION: PCR primer

<400> SEQUENCE: 264
gtctccttgg aacaggtcat ggg                                              23

<210> SEQ ID NO 265
<211> LENGTH: 22
<212> TYPE: DNA
<213> ORGANISM: Artificial Sequence
<220> FEATURE:
<223> OTHER INFORMATION: PCR primer

<400> SEQUENCE: 265
gtctgctggc tgcaggttct cc                                               22

<210> SEQ ID NO 266
<211> LENGTH: 22
<212> TYPE: DNA
<213> ORGANISM: Artificial Sequence
<220> FEATURE:
<223> OTHER INFORMATION: PCR primer

<400> SEQUENCE: 266
tctcttggcg gcaggacact cg                                               22

<210> SEQ ID NO 267
<211> LENGTH: 22
<212> TYPE: DNA
<213> ORGANISM: Artificial Sequence
<220> FEATURE:
<223> OTHER INFORMATION: PCR primer

<400> SEQUENCE: 267
gtcttctggg ggcaggtctc tc                                               22

<210> SEQ ID NO 268
<211> LENGTH: 23
<212> TYPE: DNA
<213> ORGANISM: Artificial Sequence
<220> FEATURE:
<223> OTHER INFORMATION: PCR primer

<400> SEQUENCE: 268
gtttcctggg agcaaacacc gtg                                              23

```
<210> SEQ ID NO 269
<211> LENGTH: 20
<212> TYPE: DNA
<213> ORGANISM: Artificial Sequence
<220> FEATURE:
<223> OTHER INFORMATION: PCR primer

<400> SEQUENCE: 269
tctggggcca ggctccgggc                                             20

<210> SEQ ID NO 270
<211> LENGTH: 24
<212> TYPE: DNA
<213> ORGANISM: Artificial Sequence
<220> FEATURE:
<223> OTHER INFORMATION: PCR primer

<400> SEQUENCE: 270
gtctcctggc agcagactct tttc                                        24

<210> SEQ ID NO 271
<211> LENGTH: 23
<212> TYPE: DNA
<213> ORGANISM: Artificial Sequence
<220> FEATURE:
<223> OTHER INFORMATION: PCR primer

<400> SEQUENCE: 271
atctcctggg aacagggtcc atg                                         23

<210> SEQ ID NO 272
<211> LENGTH: 23
<212> TYPE: DNA
<213> ORGANISM: Artificial Sequence
<220> FEATURE:
<223> OTHER INFORMATION: PCR primer

<400> SEQUENCE: 272
attttctggg ggcaggcctc atg                                         23

<210> SEQ ID NO 273
<211> LENGTH: 22
<212> TYPE: DNA
<213> ORGANISM: Artificial Sequence
<220> FEATURE:
<223> OTHER INFORMATION: PCR primer

<400> SEQUENCE: 273
ccttctagga gcaggccccc tg                                          22

<210> SEQ ID NO 274
<211> LENGTH: 23
<212> TYPE: DNA
<213> ORGANISM: Artificial Sequence
<220> FEATURE:
<223> OTHER INFORMATION: PCR primer

<400> SEQUENCE: 274
ttgtttcctg gctgtaggcc tcg                                         23

<210> SEQ ID NO 275
<211> LENGTH: 23
<212> TYPE: DNA
<213> ORGANISM: Artificial Sequence
<220> FEATURE:
<223> OTHER INFORMATION: PCR primer
```

```
<400> SEQUENCE: 275
tcctgggact aggctctgtg ttc                                          23

<210> SEQ ID NO 276
<211> LENGTH: 23
<212> TYPE: DNA
<213> ORGANISM: Artificial Sequence
<220> FEATURE:
<223> OTHER INFORMATION: PCR primer

<400> SEQUENCE: 276
ctgggcactt tctttggggt cag                                          23

<210> SEQ ID NO 277
<211> LENGTH: 20
<212> TYPE: DNA
<213> ORGANISM: Artificial Sequence
<220> FEATURE:
<223> OTHER INFORMATION: PCR primer

<400> SEQUENCE: 277
agagggagaa gagggcaat                                               20

<210> SEQ ID NO 278
<211> LENGTH: 20
<212> TYPE: DNA
<213> ORGANISM: Artificial Sequence
<220> FEATURE:
<223> OTHER INFORMATION: PCR primer

<400> SEQUENCE: 278
agggagcaca ggctgtctta                                              20

<210> SEQ ID NO 279
<211> LENGTH: 20
<212> TYPE: DNA
<213> ORGANISM: Artificial Sequence
<220> FEATURE:
<223> OTHER INFORMATION: PCR primer

<400> SEQUENCE: 279
ctggcaaaag aagaatgtgt                                              20

<210> SEQ ID NO 280
<211> LENGTH: 20
<212> TYPE: DNA
<213> ORGANISM: Artificial Sequence
<220> FEATURE:
<223> OTHER INFORMATION: PCR primer

<400> SEQUENCE: 280
acacagattg ggagcaggta                                              20

<210> SEQ ID NO 281
<211> LENGTH: 20
<212> TYPE: DNA
<213> ORGANISM: Artificial Sequence
<220> FEATURE:
<223> OTHER INFORMATION: PCR primer

<400> SEQUENCE: 281
ccatgacggg ttagaagctc                                              20

<210> SEQ ID NO 282
<211> LENGTH: 21
```

<212> TYPE: DNA
<213> ORGANISM: Artificial Sequence
<220> FEATURE:
<223> OTHER INFORMATION: PCR primer

<400> SEQUENCE: 282
ggatgaagaa tgacctggga t                                         21

<210> SEQ ID NO 283
<211> LENGTH: 42
<212> TYPE: DNA
<213> ORGANISM: Artificial Sequence
<220> FEATURE:
<223> OTHER INFORMATION: PCR primer

<400> SEQUENCE: 283
tggaggagaa ccctggacct atgctgcaga tgtgggggtt tg                  42

<210> SEQ ID NO 284
<211> LENGTH: 41
<212> TYPE: DNA
<213> ORGANISM: Artificial Sequence
<220> FEATURE:
<223> OTHER INFORMATION: PCR primer

<400> SEQUENCE: 284
tggaggagaa ccctggacct atgaagcagg tggcaaaagt g                   41

<210> SEQ ID NO 285
<211> LENGTH: 40
<212> TYPE: DNA
<213> ORGANISM: Artificial Sequence
<220> FEATURE:
<223> OTHER INFORMATION: PCR primer

<400> SEQUENCE: 285
tggaggagaa ccctggacct atgaagacrg tgactggacc                     40

<210> SEQ ID NO 286
<211> LENGTH: 40
<212> TYPE: DNA
<213> ORGANISM: Artificial Sequence
<220> FEATURE:
<223> OTHER INFORMATION: PCR primer

<400> SEQUENCE: 286
tggaggagaa ccctggacct atgaaaacag tgrctggacc                     40

<210> SEQ ID NO 287
<211> LENGTH: 40
<212> TYPE: DNA
<213> ORGANISM: Artificial Sequence
<220> FEATURE:
<223> OTHER INFORMATION: PCR primer

<400> SEQUENCE: 287
tggaggagaa ccctggacct atggagagga gcccgggaac                     40

<210> SEQ ID NO 288
<211> LENGTH: 40
<212> TYPE: DNA
<213> ORGANISM: Artificial Sequence
<220> FEATURE:
<223> OTHER INFORMATION: PCR primer

<400> SEQUENCE: 288
tggaggagaa ccctggacct atgsagagga acctgggagc          40

<210> SEQ ID NO 289
<211> LENGTH: 40
<212> TYPE: DNA
<213> ORGANISM: Artificial Sequence
<220> FEATURE:
<223> OTHER INFORMATION: PCR primer

<400> SEQUENCE: 289
tggaggagaa ccctggacct atgaagacag ctattcatgc          40

<210> SEQ ID NO 290
<211> LENGTH: 40
<212> TYPE: DNA
<213> ORGANISM: Artificial Sequence
<220> FEATURE:
<223> OTHER INFORMATION: PCR primer

<400> SEQUENCE: 290
tggaggagaa ccctggacct atgaaaacat atgctcctac          40

<210> SEQ ID NO 291
<211> LENGTH: 44
<212> TYPE: DNA
<213> ORGANISM: Artificial Sequence
<220> FEATURE:
<223> OTHER INFORMATION: PCR primer

<400> SEQUENCE: 291
tggaggagaa ccctggacct atgaactatt ctccagcttt agtg          44

<210> SEQ ID NO 292
<211> LENGTH: 42
<212> TYPE: DNA
<213> ORGANISM: Artificial Sequence
<220> FEATURE:
<223> OTHER INFORMATION: PCR primer

<400> SEQUENCE: 292
tggaggagaa ccctggacct atgaacactt ctccagcttt ag          42

<210> SEQ ID NO 293
<211> LENGTH: 42
<212> TYPE: DNA
<213> ORGANISM: Artificial Sequence
<220> FEATURE:
<223> OTHER INFORMATION: PCR primer

<400> SEQUENCE: 293
tggaggagaa ccctggacct atgaacaatt ccccagcttt ag          42

<210> SEQ ID NO 294
<211> LENGTH: 42
<212> TYPE: DNA
<213> ORGANISM: Artificial Sequence
<220> FEATURE:
<223> OTHER INFORMATION: PCR primer

<400> SEQUENCE: 294
tggaggagaa ccctggacct atgaatactt ctccagtttt ag          42

<210> SEQ ID NO 295
<211> LENGTH: 41
<212> TYPE: DNA
<213> ORGANISM: Artificial Sequence

```
<220> FEATURE:
<223> OTHER INFORMATION: PCR primer

<400> SEQUENCE: 295
tggaggagaa ccctggacct atgaaccttt gtcctgaact g                    41

<210> SEQ ID NO 296
<211> LENGTH: 41
<212> TYPE: DNA
<213> ORGANISM: Artificial Sequence
<220> FEATURE:
<223> OTHER INFORMATION: PCR primer

<400> SEQUENCE: 296
tggaggagaa ccctggacct atggactytt ctccaggctt c                    41

<210> SEQ ID NO 297
<211> LENGTH: 42
<212> TYPE: DNA
<213> ORGANISM: Artificial Sequence
<220> FEATURE:
<223> OTHER INFORMATION: PCR primer

<400> SEQUENCE: 297
tggaggagaa ccctggacct atgaagtcct tgtgtgtttc ac                   42

<210> SEQ ID NO 298
<211> LENGTH: 45
<212> TYPE: DNA
<213> ORGANISM: Artificial Sequence
<220> FEATURE:
<223> OTHER INFORMATION: PCR prier

<400> SEQUENCE: 298
tggaggagaa ccctggacct atgaaatcct ttagtatttc cctag                45

<210> SEQ ID NO 299
<211> LENGTH: 40
<212> TYPE: DNA
<213> ORGANISM: Artificial Sequence
<220> FEATURE:
<223> OTHER INFORMATION: PCR primer

<400> SEQUENCE: 299
tggaggagaa ccctggacct atgaaatcct tgagtgtttc                      40

<210> SEQ ID NO 300
<211> LENGTH: 42
<212> TYPE: DNA
<213> ORGANISM: Artificial Sequence
<220> FEATURE:
<223> OTHER INFORMATION: PCR primer

<400> SEQUENCE: 300
tggaggagaa ccctggacct atgaaatcct tgagtgtttt ac                   42

<210> SEQ ID NO 301
<211> LENGTH: 42
<212> TYPE: DNA
<213> ORGANISM: Artificial Sequence
<220> FEATURE:
<223> OTHER INFORMATION: PCR primer

<400> SEQUENCE: 301
tggaggagaa ccctggacct atgcattcct tacatgtttc ac                   42
```

<210> SEQ ID NO 302
<211> LENGTH: 41
<212> TYPE: DNA
<213> ORGANISM: Artificial Sequence
<220> FEATURE:
<223> OTHER INFORMATION: PCR primer

<400> SEQUENCE: 302
tggaggagaa ccctggacct atgcacagcc tcctggggtt g           41

<210> SEQ ID NO 303
<211> LENGTH: 39
<212> TYPE: DNA
<213> ORGANISM: Artificial Sequence
<220> FEATURE:
<223> OTHER INFORMATION: PCR primer

<400> SEQUENCE: 303
tggaggagaa ccctggacct atgaacagat tcctgggaa             39

<210> SEQ ID NO 304
<211> LENGTH: 41
<212> TYPE: DNA
<213> ORGANISM: Artificial Sequence
<220> FEATURE:
<223> OTHER INFORMATION: PCR primer

<400> SEQUENCE: 304
tggaggagaa ccctggacct atgctcctgg tyctcatctc g          41

<210> SEQ ID NO 305
<211> LENGTH: 39
<212> TYPE: DNA
<213> ORGANISM: Artificial Sequence
<220> FEATURE:
<223> OTHER INFORMATION: PCR primer

<400> SEQUENCE: 305
tggaggagaa ccctggacct atgctcctgy tgctcctcc             39

<210> SEQ ID NO 306
<211> LENGTH: 39
<212> TYPE: DNA
<213> ORGANISM: Artificial Sequence
<220> FEATURE:
<223> OTHER INFORMATION: PCR primer

<400> SEQUENCE: 306
tggaggagaa ccctggacct atgctcctgg cactcctcc             39

<210> SEQ ID NO 307
<211> LENGTH: 42
<212> TYPE: DNA
<213> ORGANISM: Artificial Sequence
<220> FEATURE:
<223> OTHER INFORMATION: PCR primer

<400> SEQUENCE: 307
tggaggagaa ccctggacct atgaagacat cccttcacac tg         42

<210> SEQ ID NO 308
<211> LENGTH: 43
<212> TYPE: DNA
<213> ORGANISM: Artificial Sequence
<220> FEATURE:
<223> OTHER INFORMATION: PCR primer

<400> SEQUENCE: 308
tggaggagaa ccctggacct atgaaaaagt gccttagtgc ctg        43

<210> SEQ ID NO 309
<211> LENGTH: 41
<212> TYPE: DNA
<213> ORGANISM: Artificial Sequence
<220> FEATURE:
<223> OTHER INFORMATION: PCR primer

<400> SEQUENCE: 309
tggaggagaa ccctggacct atgaaaaagy gcctgagtgc c          41

<210> SEQ ID NO 310
<211> LENGTH: 40
<212> TYPE: DNA
<213> ORGANISM: Artificial Sequence
<220> FEATURE:
<223> OTHER INFORMATION: PCR primer

<400> SEQUENCE: 310
tggaggagaa ccctggacct atgcgtcctg tcacctgctc            40

<210> SEQ ID NO 311
<211> LENGTH: 40
<212> TYPE: DNA
<213> ORGANISM: Artificial Sequence
<220> FEATURE:
<223> OTHER INFORMATION: PCR primer

<400> SEQUENCE: 311
tggaggagaa ccctggacct atgaacatgc gtcctgwcac            40

<210> SEQ ID NO 312
<211> LENGTH: 40
<212> TYPE: DNA
<213> ORGANISM: Artificial Sequence
<220> FEATURE:
<223> OTHER INFORMATION: PCR primer

<400> SEQUENCE: 312
tggaggagaa ccctggacct atgcgtcctg wcacctcctc            40

<210> SEQ ID NO 313
<211> LENGTH: 43
<212> TYPE: DNA
<213> ORGANISM: Artificial Sequence
<220> FEATURE:
<223> OTHER INFORMATION: PCR primer

<400> SEQUENCE: 313
tggaggagaa ccctggacct atgaacatgc atcctgtcac ctg        43

<210> SEQ ID NO 314
<211> LENGTH: 41
<212> TYPE: DNA
<213> ORGANISM: Artificial Sequence
<220> FEATURE:
<223> OTHER INFORMATION: PCR primer

<400> SEQUENCE: 314
tggaggagaa ccctggacct atgcgtcctg rcacctgctc a          41

<210> SEQ ID NO 315

```
<211> LENGTH: 40
<212> TYPE: DNA
<213> ORGANISM: Artificial Sequence
<220> FEATURE:
<223> OTHER INFORMATION: PCR primer

<400> SEQUENCE: 315
tggaggagaa ccctggacct atgaacaggc tgctgtgctc                           40

<210> SEQ ID NO 316
<211> LENGTH: 40
<212> TYPE: DNA
<213> ORGANISM: Artificial Sequence
<220> FEATURE:
<223> OTHER INFORMATION: PCR primer

<400> SEQUENCE: 316
tggaggagaa ccctggacct atgaagaggc tgctgagctc                           40

<210> SEQ ID NO 317
<211> LENGTH: 37
<212> TYPE: DNA
<213> ORGANISM: Artificial Sequence
<220> FEATURE:
<223> OTHER INFORMATION: PCR primer

<400> SEQUENCE: 317
tggaggagaa ccctggacct atgaagaggc tgatgtg                              37

<210> SEQ ID NO 318
<211> LENGTH: 41
<212> TYPE: DNA
<213> ORGANISM: Artificial Sequence
<220> FEATURE:
<223> OTHER INFORMATION: PCR primer

<400> SEQUENCE: 318
tggaggagaa ccctggacct atggacamga tcctgacagc a                         41

<210> SEQ ID NO 319
<211> LENGTH: 43
<212> TYPE: DNA
<213> ORGANISM: Artificial Sequence
<220> FEATURE:
<223> OTHER INFORMATION: PCR primer

<400> SEQUENCE: 319
tggaggagaa ccctggacct atggacaaga ttctgacagc atc                       43

<210> SEQ ID NO 320
<211> LENGTH: 41
<212> TYPE: DNA
<213> ORGANISM: Artificial Sequence
<220> FEATURE:
<223> OTHER INFORMATION: PCR primer

<400> SEQUENCE: 320
tggaggagaa ccctggacct atggacaaga acctgacagc a                         41

<210> SEQ ID NO 321
<211> LENGTH: 38
<212> TYPE: DNA
<213> ORGANISM: Artificial Sequence
<220> FEATURE:
<223> OTHER INFORMATION: PCR primer

<400> SEQUENCE: 321
```

```
tggaggagaa ccctggacct atgcctcctc acagcctg                                    38
```

<210> SEQ ID NO 322
<211> LENGTH: 41
<212> TYPE: DNA
<213> ORGANISM: Artificial Sequence
<220> FEATURE:
<223> OTHER INFORMATION: PCR primer

<400> SEQUENCE: 322

```
tggaggagaa ccctggacct atgcctcctc agagcctgct c                                41
```

<210> SEQ ID NO 323
<211> LENGTH: 38
<212> TYPE: DNA
<213> ORGANISM: Artificial Sequence
<220> FEATURE:
<223> OTHER INFORMATION: PCR primer

<400> SEQUENCE: 323

```
tggaggagaa ccctggacct atgctgattc taagcctg                                    38
```

<210> SEQ ID NO 324
<211> LENGTH: 38
<212> TYPE: DNA
<213> ORGANISM: Artificial Sequence
<220> FEATURE:
<223> OTHER INFORMATION: PCR primer

<400> SEQUENCE: 324

```
tggaggagaa ccctggacct atgaagaggc tgctgtgc                                    38
```

<210> SEQ ID NO 325
<211> LENGTH: 38
<212> TYPE: DNA
<213> ORGANISM: Artificial Sequence
<220> FEATURE:
<223> OTHER INFORMATION: PCR primer

<400> SEQUENCE: 325

```
tggaggagaa ccctggacct atgctcctgg cactcctc                                    38
```

<210> SEQ ID NO 326
<211> LENGTH: 41
<212> TYPE: DNA
<213> ORGANISM: Artificial Sequence
<220> FEATURE:
<223> OTHER INFORMATION: PCR primer

<400> SEQUENCE: 326

```
tggaggagaa ccctggacct atgttccyag tgaccattct g                                41
```

<210> SEQ ID NO 327
<211> LENGTH: 41
<212> TYPE: DNA
<213> ORGANISM: Artificial Sequence
<220> FEATURE:
<223> OTHER INFORMATION: PCR primer

<400> SEQUENCE: 327

```
tggaggagaa ccctggacct atgactggct tcctgaaggc c                                41
```

<210> SEQ ID NO 328
<211> LENGTH: 43
<212> TYPE: DNA

```
<213> ORGANISM: Artificial Sequence
<220> FEATURE:
<223> OTHER INFORMATION: PCR primer

<400> SEQUENCE: 328
tggaggagaa ccctggacct atgggatgtg tgagtggaat tgc                    43

<210> SEQ ID NO 329
<211> LENGTH: 44
<212> TYPE: DNA
<213> ORGANISM: Artificial Sequence
<220> FEATURE:
<223> OTHER INFORMATION: PCR primer

<400> SEQUENCE: 329
aaggatccga attcctgcag gatgtggcag ttttgcattc tgtg                   44

<210> SEQ ID NO 330
<211> LENGTH: 45
<212> TYPE: DNA
<213> ORGANISM: Artificial Sequence
<220> FEATURE:
<223> OTHER INFORMATION: PCR primer

<400> SEQUENCE: 330
aaggatccga attcctgcag gatgggctcc attttcctca gttgc                  45

<210> SEQ ID NO 331
<211> LENGTH: 45
<212> TYPE: DNA
<213> ORGANISM: Artificial Sequence
<220> FEATURE:
<223> OTHER INFORMATION: PCR primer

<400> SEQUENCE: 331
aaggatccga attcctgcag gatggatatc tggcttctag gttgg                  45

<210> SEQ ID NO 332
<211> LENGTH: 41
<212> TYPE: DNA
<213> ORGANISM: Artificial Sequence
<220> FEATURE:
<223> OTHER INFORMATION: PCR primer

<400> SEQUENCE: 332
aaggatccga attcctgcag gatgggctgt aggctcctaa g                      41

<210> SEQ ID NO 333
<211> LENGTH: 39
<212> TYPE: DNA
<213> ORGANISM: Artificial Sequence
<220> FEATURE:
<223> OTHER INFORMATION: PCR primer

<400> SEQUENCE: 333
aaggatccga attcctgcag gatgagctgc aggcttctc                         39

<210> SEQ ID NO 334
<211> LENGTH: 43
<212> TYPE: DNA
<213> ORGANISM: Artificial Sequence
<220> FEATURE:
<223> OTHER INFORMATION: PCR primer

<400> SEQUENCE: 334
aaggatccga attcctgcag gatgtctaac actgtcctcg ctg                    43
```

<210> SEQ ID NO 335
<211> LENGTH: 43
<212> TYPE: DNA
<213> ORGANISM: Artificial Sequence
<220> FEATURE:
<223> OTHER INFORMATION: PCR primer

<400> SEQUENCE: 335
aaggatccga attcctgcag gatgtctaac actgccttcc ctg         43

<210> SEQ ID NO 336
<211> LENGTH: 40
<212> TYPE: DNA
<213> ORGANISM: Artificial Sequence
<220> FEATURE:
<223> OTHER INFORMATION: PCR primer

<400> SEQUENCE: 336
aaggatccga attcctgcag gatgggctcc aggctctttc         40

<210> SEQ ID NO 337
<211> LENGTH: 43
<212> TYPE: DNA
<213> ORGANISM: Artificial Sequence
<220> FEATURE:
<223> OTHER INFORMATION: PCR primer

<400> SEQUENCE: 337
aaggatccga attcctgcag gatgggctcc aggctcttct tcg         43

<210> SEQ ID NO 338
<211> LENGTH: 43
<212> TYPE: DNA
<213> ORGANISM: Artificial Sequence
<220> FEATURE:
<223> OTHER INFORMATION: PCR primer

<400> SEQUENCE: 338
aaggatccga attcctgcag gatgggctcc agactcttct ttg         43

<210> SEQ ID NO 339
<211> LENGTH: 40
<212> TYPE: DNA
<213> ORGANISM: Artificial Sequence
<220> FEATURE:
<223> OTHER INFORMATION: PCR primer

<400> SEQUENCE: 339
aaggatccga attcctgcag gatgggcacc aggcttcttg         40

<210> SEQ ID NO 340
<211> LENGTH: 41
<212> TYPE: DNA
<213> ORGANISM: Artificial Sequence
<220> FEATURE:
<223> OTHER INFORMATION: PCR primer

<400> SEQUENCE: 340
aaggatccga attcctgcag gatgggcatc cagaccctct g         41

<210> SEQ ID NO 341
<211> LENGTH: 44
<212> TYPE: DNA
<213> ORGANISM: Artificial Sequence
<220> FEATURE:

<223> OTHER INFORMATION: PCR primer

<400> SEQUENCE: 341
aaggatccga attcctgcag gatggccccc aggctccttt tctg        44

<210> SEQ ID NO 342
<211> LENGTH: 46
<212> TYPE: DNA
<213> ORGANISM: Artificial Sequence
<220> FEATURE:
<223> OTHER INFORMATION: PCR priemr

<400> SEQUENCE: 342
aaggatccga attcctgcag gatggatcct agacttcttt gctgtg      46

<210> SEQ ID NO 343
<211> LENGTH: 42
<212> TYPE: DNA
<213> ORGANISM: Artificial Sequence
<220> FEATURE:
<223> OTHER INFORMATION: PCR primer

<400> SEQUENCE: 343
aaggatccga attcctgcag gatgaacaag tgggttttct gc          42

<210> SEQ ID NO 344
<211> LENGTH: 46
<212> TYPE: DNA
<213> ORGANISM: Artificial Sequence
<220> FEATURE:
<223> OTHER INFORMATION: PCR primer

<400> SEQUENCE: 344
aaggatccga attcctgcag gatgttactg cttctattac ttctgg      46

<210> SEQ ID NO 345
<211> LENGTH: 41
<212> TYPE: DNA
<213> ORGANISM: Artificial Sequence
<220> FEATURE:
<223> OTHER INFORMATION: PCR primer

<400> SEQUENCE: 345
aaggatccga attcctgcag gatgggtgca cggctcattt g           41

<210> SEQ ID NO 346
<211> LENGTH: 41
<212> TYPE: DNA
<213> ORGANISM: Artificial Sequence
<220> FEATURE:
<223> OTHER INFORMATION: PCR primer

<400> SEQUENCE: 346
aaggatccga attcctgcag gatgggtgca agactgctct g           41

<210> SEQ ID NO 347
<211> LENGTH: 42
<212> TYPE: DNA
<213> ORGANISM: Artificial Sequence
<220> FEATURE:
<223> OTHER INFORMATION: PCR primer

<400> SEQUENCE: 347
aaggatccga attcctgcag gatggctaca aggctcctct gt          42

-continued

```
<210> SEQ ID NO 348
<211> LENGTH: 44
<212> TYPE: DNA
<213> ORGANISM: Artificial Sequence
<220> FEATURE:
<223> OTHER INFORMATION: PCR primer

<400> SEQUENCE: 348
aaggatccga attcctgcag gatgagagtt aggctcatct ctgc            44

<210> SEQ ID NO 349
<211> LENGTH: 43
<212> TYPE: DNA
<213> ORGANISM: Artificial Sequence
<220> FEATURE:
<223> OTHER INFORMATION: PCR primer

<400> SEQUENCE: 349
aaggatccga attcctgcag gatgtggaca ttcctgctac ttc             43

<210> SEQ ID NO 350
<211> LENGTH: 41
<212> TYPE: DNA
<213> ORGANISM: Artificial Sequence
<220> FEATURE:
<223> OTHER INFORMATION: PCR primer

<400> SEQUENCE: 350
aaggatccga attcctgcag gatgctgtac tctctccttg c               41

<210> SEQ ID NO 351
<211> LENGTH: 23
<212> TYPE: DNA
<213> ORGANISM: Artificial Sequence
<220> FEATURE:
<223> OTHER INFORMATION: PCR primer

<400> SEQUENCE: 351
catcacaggg aacgtctgaa ctg                                   23

<210> SEQ ID NO 352
<211> LENGTH: 23
<212> TYPE: DNA
<213> ORGANISM: Artificial Sequence
<220> FEATURE:
<223> OTHER INFORMATION: PCR primer

<400> SEQUENCE: 352
tcggcacatt gatttgggag tca                                   23

<210> SEQ ID NO 353
<211> LENGTH: 20
<212> TYPE: DNA
<213> ORGANISM: Artificial Sequence
<220> FEATURE:
<223> OTHER INFORMATION: PCR primer

<400> SEQUENCE: 353
gtaatcccac agtctgctcg                                       20

<210> SEQ ID NO 354
<211> LENGTH: 20
<212> TYPE: DNA
<213> ORGANISM: Artificial Sequence
<220> FEATURE:
<223> OTHER INFORMATION: PCR primer
```

```
<400> SEQUENCE: 354
gtgattccac agtctgctcg                                              20

<210> SEQ ID NO 355
<211> LENGTH: 22
<212> TYPE: DNA
<213> ORGANISM: Artificial Sequence
<220> FEATURE:
<223> OTHER INFORMATION: PCR primer

<400> SEQUENCE: 355
caagcacacg agggtagcct tt                                           22
```

METHOD FOR AMPLIFYING A T CELL RECEPTOR (TCR) CDNA

TECHNICAL FIELD

The present invention relates to a method for amplifying a T cell receptor (TCR) gene. The present invention is useful in the fields of life science, medical science and so forth concerning TCR gene therapies of cancers and infectious diseases.

BACKGROUND ART

In the T cell receptor (TCR) gene therapy, of which application mainly to specific cancers is being investigated, a cancer antigen-specific TCR gene is introduced into lymphocytes of a cancer patient. In order to obtain an antigen-specific TCR gene, it is necessary to specify a T cell that can recognize the cancer antigen from T cells among peripheral blood lymphocytes (PBL) collected from the patient, and to clone the TCR gene. Approaches generally made for this purpose include establishing an antigen-specific T cell clone, and this procedure usually requires several months. However, the inventors of the present invention developed a method for amplifying a gene from a single cell by using the 5'-RACE method, which does not require establishment of a cell clone (Patent document 1).

The inventors of the present invention also constructed a system that can detect a cancer-specific T cell from peripheral blood T lymphocytes of a cancer patient, amplify cDNA of TCR that recognizes cancer from a single cancer-specific T cell, and verify the cancer-specificity thereof within ten days in the shortest case (Patent document 2, Non-patent document 1). In this method, the aforementioned 5'-RACE method was used for amplifying a target cDNA.

Amplification of a TCR gene and one-step expression cloning have also been proposed by Moysey et. al. (Non-patent document 1).

PRIOR ART REFERENCES

Patent Documents

Patent document 1: Japanese Patent No. 4069133
Patent document 2: Japanese Patent Application No. 2012-164442 (PCT/JP2013/070028)

Non-Patent Documents

Non-patent document 1: Kobayashi E et al., A new cloning and expression system yields and validates TCRs from blood lymphocytes of patients with cancer within 10 days, Nature Medicine, Published online: 13 Oct. 2013 doi: 10.1038-/nm.3358
Non-patent document 2: Moysey R et al., Amplification and one-step expression cloning of human T cell receptor genes, Anal. Biochem., 326:284-286, 2004

SUMMARY OF THE INVENTION

Object to be Achieved by the Invention cDNA of TCR is constituted by a combination of a variable (V) region and a constant (C) region. There are about 50 kinds of V regions in the human body, and cDNAs of TCRs can be amplified by using primers corresponding to each of the V regions. However, in such amplification, cDNA containing neither a translation initiation codon nor a leader sequence is amplified, and therefore when the gene is expressed in an animal cell or introduced into a T cell for gene therapy, it is necessary to add a leader sequence. In order to avoid such a procedure, TCR cDNA is amplified by the 5'-RACE method in the techniques of Patent document 2 and Non-patent document 1. However, when the 5'-RACE method is performed, cDNAs produced from mRNAs by using a reverse transcriptase are usually used as a material, and they include cDNAs of various lengths from a short one to long one. If PCR is performed with such cDNAs, cDNAs of various lengths are amplified, and subsequent analysis tends to become complicated. The 5'-RACE method also additionally requires a step of using TdT unlike common RT-PCR, and therefore it suffers from a disadvantage that additional time for the experiment, material cost etc. are required.

The method of Moysey et al. comprises two times of PCR. Since a sequence of 5' end side of the V region is used for the second PCR, the produced TCR cDNA does not contain a leader sequence, and it is necessary to add a leader sequence for expression thereof in a cell. Further, since the method of Moysey et al. requires about 500 cells for amplification of TCR, a clone of a cancer-specific T cell must be first prepared, and then proliferated to obtain 500 clones, and thus it requires about three months for amplifying a target TCR.

Means for Achieving the Object

In the present invention, 80 kinds of primers corresponding to leader sequences containing a translation initiation codon were produced on the basis of data of leader sequences existing on the 5' side of V regions, and it was attempted to amplify TCR cDNA, from a single T cell by the usual RT-PCR using the primers. At first, since a mixture of many kinds of primers was used, reduction of amplification efficiency of PCR was concerned, but as a result, it was found that TCR cDNA could be extremely efficiently obtained from a single T cell, and thus the present invention was accomplished. The present invention provides the followings.

[1] A method for amplifying a T cell receptor (TCR) cDNA, which comprises the following step (1) and step (2):
(1) the step of performing PCR by using at least one kind of the L primer mentioned below, the C primer 1 mentioned below, and cDNA obtained from a single cell as the template to obtain an amplification product 1;
an L primer comprising an adapter part consisting of an adapter sequence of 15- to 25-nucleotide length, and a leader region-annealing part of 15- to 25-nucleotide length, which is ligated downstream from the adapter part, and can anneal to a part of a leader region containing a translation initiation codon, or an upstream part thereof,
a C primer 1 consisting of a nucleotide sequence of 15- to 25-nucleotide length, which can anneal to a part of a constant region,
(2) the step of performing PCR by using the adaptor primer mentioned below, the C primer 2 mentioned below, and the amplification product 1 as the template to obtain an amplification product 2;
an adapter primer consisting of a nucleotide sequence of 15- to 25-nucleotide length, which can anneal to the adapter part of the amplification product 1, a C primer 2, which can anneal to a part of the constant region existing upstream from the region to which the C primer 1 anneals.

[2] The amplification method according to [1], wherein, in the step (1), as the L primer, at least one kind of L primer corresponding to TCRα (AL) and at least one kind of L primer corresponding to TCRβ (BL) are used;

as the C primer 1, a C primer 1 corresponding to TCRα (Ca_RV1) and a C primer 1 corresponding to TCRβ (Cb_RV1) are used, and TCR and TCR are simultaneously amplified.

[3] The amplification method according to [2], wherein the leader region-annealing part of AL consists of a part of any one of the nucleotide sequences of SEQ ID NOS: 87 to 140, and the leader region-annealing part of BL consists of a part of any one of the nucleotide sequences of SEQ ID NOS: 141 to 188.

[4] The amplification method according to [3], wherein the leader region-annealing part of AL consists of any one of the nucleotide sequences of SEQ ID NOS: 1 to 41, and the leader region-annealing part of BL consists of any one of the nucleotide sequences of SEQ ID NOS: 42 to 80.

[5] The amplification method according to [4], wherein 41 kinds of ALs corresponding to the sequences of SEQ ID NOS: 1 to 41, respectively, and 39 kinds of BLs corresponding to the sequences of SEQ ID NOS: 42 to 80, respectively, are used.

[6] The amplification method according to any one of [2] to [5], wherein the adapter part of AL consists of the nucleotide sequence of SEQ ID NO: 81, and the adapter part of BL consists of the nucleotide sequence of SEQ ID NO: 82.

[7] The amplification method according to any one of [2] to [6], wherein Ca_RV1 consists of the nucleotide sequence of SEQ ID NO: 83, and Cb_RV1 consists of the nucleotide sequence of SEQ ID NO: 84.

[8] The amplification method according to any one of [2] to [7], wherein, as the C primer 2, a C primer 2 corresponding to TCRα (Ca_RV2) and a C primer 2 corresponding to TCRβ (Cb_RV2) are used, Ca_RV2 consists of the nucleotide sequence of SEQ ID NO: 85, and Cb_RV2 consists of the nucleotide sequence of SEQ ID NO: 86.

[9] A kit for amplifying a TCR cDNA, which comprises:

an L primer comprising an adapter part consisting of an adapter sequence of 15- to 25-nucleotide length, and a leader region-annealing part of 15- to 25-nucleotide length, which is ligated downstream from the adapter part, and can anneal to a part of a leader region containing a translation initiation codon, or an upstream part thereof, a C primer 1 consisting of a nucleotide sequence of 15- to 25-nucleotide length, which can anneal to a part of a constant region, an adapter primer consisting of a nucleotide sequence of 15- to 25-nucleotide length, which can anneal to the adapter part of an amplification product 1, and a C primer 2, which can anneal to a part of the constant region existing upstream from the region to which the C primer 1 anneals.

[10] The kit according to [9], wherein the leader region-annealing part of AL consists of a part of any one of the nucleotide sequences of SEQ ID NOS: 87 to 140, and the leader region-annealing part of BL consists of a part of any one of the nucleotide sequences of SEQ ID NOS: 141 to 188.

[11] The kit according to [10], wherein the leader region-annealing sequence of AL consists of any one of the nucleotide sequences of SEQ ID NOS: 1 to 41, and the leader region-annealing sequence of BL consists of any one of the nucleotide sequences of SEQ ID NOS: 42 to 80.

[12] The kit according to [11], which comprises 41 kinds of ALs corresponding to the sequences of SEQ ID NOS: 1 to 41, respectively, and 39 kinds of BLs corresponding to the sequences of SEQ ID NOS: 42 to 80, respectively.

[1] A method for amplifying a T cell receptor (TCR) cDNA, which comprises the following step (1) and step (2):

(1) the step of performing PCR by using at least one kind of the L primer mentioned below, the C primer 1 or UTR primer 1 mentioned below, and cDNA obtained from a single cell as the template to obtain an amplification product 1;

an L primer of 30- to 60-nucleotide length comprising an adapter part of 15- to 25-nucleotide length, and a leader region-annealing part of 15- to 25-nucleotide length, which is ligated downstream from the adapter part, and can anneal to a part of a leader region containing a translation initiation codon, or an upstream part thereof, a C primer 1 of 15- to 25-nucleotide length, which can anneal to a part of a constant region, or a UTR primer 1 of 15- to 25-nucleotide length, which can anneal to a part of a 3' untranslated region, (2) the step of performing PCR by using the adaptor primer mentioned below, the C primer 2 or UTR primer 2 mentioned below, and the amplification product 1 as the template to obtain an amplification product 2;

an adapter primer of 15- to 25-nucleotide length, which can anneal to the adapter part of the amplification product 1, a C primer 2 of 15- to 25-nucleotide length, which can anneal to a part of the constant region existing upstream from the region to which the C primer 1 anneals, or a UTR primer 2 of 15- to 25-nucleotide length, which can anneal to a part of the 3' untranslated region existing upstream from the region to which the UTR primer 1 anneals.

[2] The amplification method according to [1], wherein, in the step (1), as the L primer, at least one kind of L primer corresponding to TCRα (AL) and at least one kind of L primer corresponding to TCRβ (BL) are used;

as the C primer 1, a C primer 1 corresponding to TCRα (Ca_RV1) and a C primer 1 corresponding to TCRβ (Cb_RV1) are used, or as the UTR primer 1, a UTR primer 1 corresponding to TCRα (AC_UTR1) and a UTR primer 1 corresponding to TCR (BC_UTR1) are used, and TCRα and TCRβ are simultaneously amplified.

[3] The amplification method according to [2], wherein the leader region-annealing part of AL consists of a part of any one of the nucleotide sequences of SEQ ID NOS: 87 to 140, and the leader region-annealing part of BL consists of a part of any one of the nucleotide sequences of SEQ ID NOS: 141 to 188.

[4] The amplification method according to [2], wherein the leader region-annealing part of AL consists of any one of the nucleotide sequences of SEQ ID NOS: 1 to 41, and the leader region-annealing part of BL consists of any one of the nucleotide sequences of SEQ ID NOS: 42 to 80, or the leader region-annealing part of AL consists of any one of the nucleotide sequences of SEQ ID NOS: 283 to 328, and the leader region-annealing part of BL consists of any one of the nucleotide sequences of SEQ ID NOS: 329 to 350.

[5] The amplification method according to [4], wherein 41 kinds of ALs corresponding to the sequences of SEQ ID NOS: 1 to 41, respectively, and 39 kinds of BLs corresponding to the sequences of SEQ ID NOS: 42 to 80, respectively, are used as the L primer, or 46 kinds of ALs corresponding to the sequences of SEQ ID NOS: 283 to 328, respectively, and 22 kinds of BLs corresponding to the sequences of SEQ ID NOS: 329 to 350, respectively, are used as the L primer.

[6] The amplification method according to any one of [2] to [5], wherein the adapter part of AL consists of the nucleotide sequence of SEQ ID NO: 81, and the adapter part of BL consists of the nucleotide sequence of SEQ ID NO: 82.

[7] The amplification method according to any one of [2] to [6], wherein Ca_RV1 is a polynucleotide consisting of the nucleotide sequence of SEQ ID NO: 83 or SEQ ID NO: 351, and Cb_RV1 is a polynucleotide consisting of the nucleotide sequences of SEQ ID NO: 84 or SEQ ID NO: 353 and SEQ ID NO: 354, or
AC_UTR1 is a polynucleotide consisting of the nucleotide sequence of SEQ ID NO: 277, and BC_UTR1 is a polynucleotide consisting of the nucleotide sequences of SEQ ID NO: 279 and/or SEQ ID NO: 280.

[8] The amplification method according to any one of [2] to [7], wherein:
as the C primer 2, a C primer 2 corresponding to TCRα (Ca_RV2) and a C primer 2 corresponding to TCRβ (Cb_RV2) are used, Ca_RV2 consists of the nucleotide sequence of SEQ ID NO: 85 or SEQ ID NO: 352, and Cb_RV2 consists of the nucleotide sequence of SEQ ID NO: 86 or SEQ ID NO: 355, or
as the UTR primer 2, a UTR primer 2 corresponding to TCRα (AC_UTR2) and a C primer 2 corresponding to TCRβ (BC_UTR2) are used, AC_UTR2 consists of the nucleotide sequence of SEQ ID NO: 278, and BC_UTR2 consists of the nucleotide sequences of SEQ ID NO: 281 and/or SEQ ID NO: 282.

[9] A kit for amplifying a TCR cDNA, which comprises:
an L primer of 30- to 60-nucleotide length comprising an adapter part of 15- to 25-nucleotide length, and a leader region-annealing part of 15- to 25-nucleotide length, which is ligated downstream from the adapter part, and can anneal to a part of a leader region containing a translation initiation codon, or an upstream part thereof,
a C primer 1 of 15- to 25-nucleotide length, which can anneal to a part of a constant region, or a UTR primer 1 of 15- to 25-nucleotide length, which can anneal to a part of a 3' untranslated region,
an adapter primer of 15- to 25-nucleotide length, which can anneal to the adapter part of an amplification product 1,
a C primer 2 of 15- to 25-nucleotide length, which can anneal to a part of the constant region existing upstream from the region to which the C primer 1 anneals, or a UTR primer 2 of 15- to 25-nucleotide length, which can anneal to a part of the 3' untranslated region existing upstream from the region to which the UTR primer 1 anneals.

[10] The kit according to [9], wherein the leader region-annealing part of AL can anneal to a region consisting of any one of the nucleotide sequences of SEQ ID NOS: 85 to 140, and the leader region-annealing part of BL can anneal to a region consisting of any one of the nucleotide sequences of SEQ ID NOS: 141 to 188.

[11] The kit according to [10], wherein the leader region-annealing part of AL consists of any one of the nucleotide sequences of SEQ ID NOS: 1 to 41, and the leader region-annealing part of BL consists of any one of the nucleotide sequences of SEQ ID NOS: 42 to 80.

[12] The kit according to [11], which comprises 41 kinds of ALs corresponding to the sequences of SEQ ID NOS: 1 to 41, respectively, and 39 kinds of BLs corresponding to the sequences of SEQ ID NOS: 42 to 80, respectively.

Effect of the Invention

According to the amplification method of the present invention, a TCR cDNA including a leader sequence containing a translation initiation codon and a complete variable region can be efficiently amplified from a single T cell. According to the amplification method of the present invention, a TCRαβ pair can be amplified with high probability. Since the amplification method of the present invention does not require preparation of a T cell clone for obtaining a target TCR, it enables amplification of cDNA of TCR in a short period of time.

Since the amplification product eventually obtained by the amplification method of the present invention includes a leader sequence containing a translation initiation codon and a complete variable region, it can be inserted into an expression vector and used as it is, and it can be expressed by a T cell.

BRIEF DESCRIPTION OF THE DRAWINGS

Figure 1:
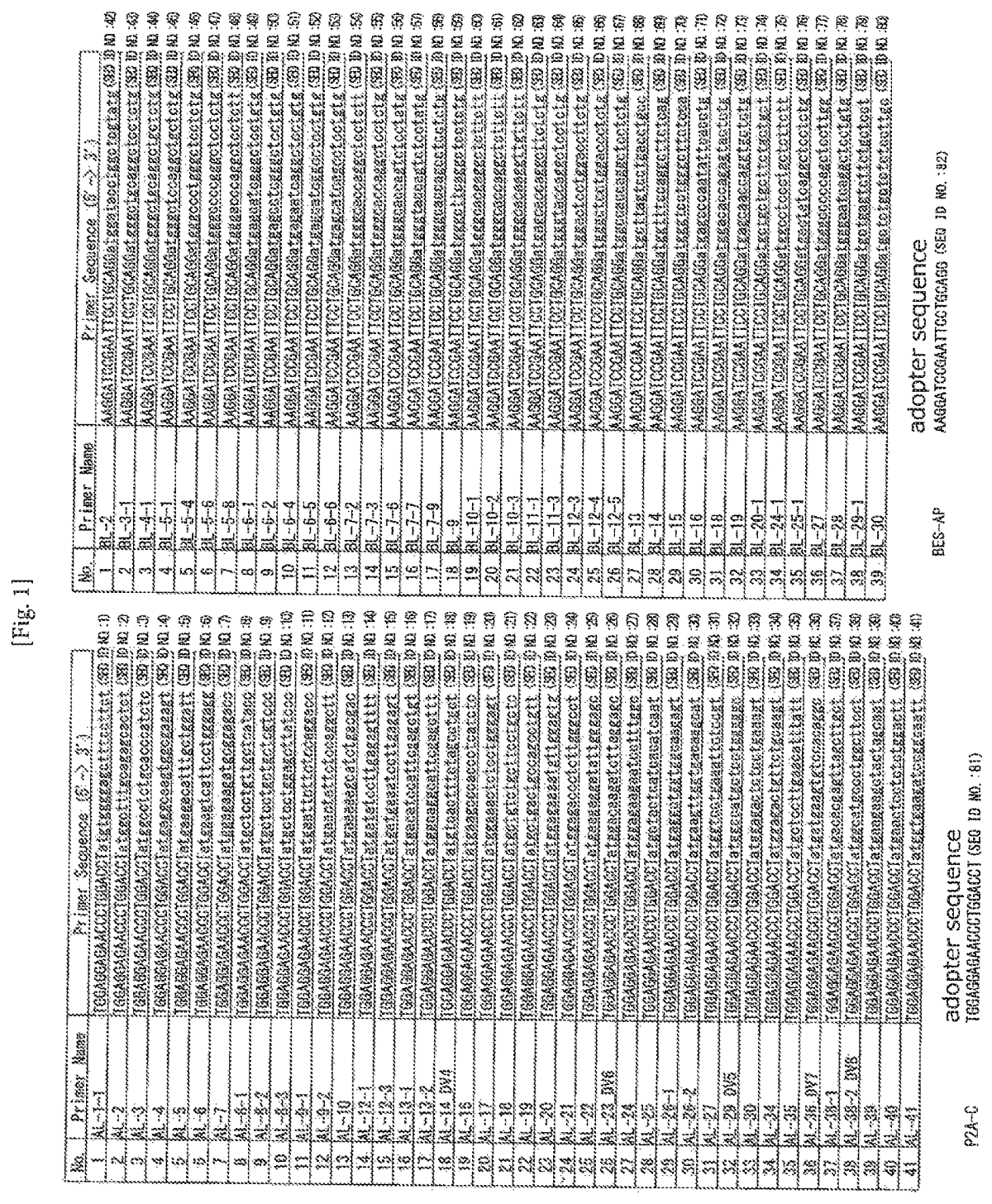

FIG. 1 Table of the sequences of the primers designed in the examples (AL, SEQ ID NOS: 1 to 41; BL, SEQ ID NOS: 42 to 80).

Figure 2:
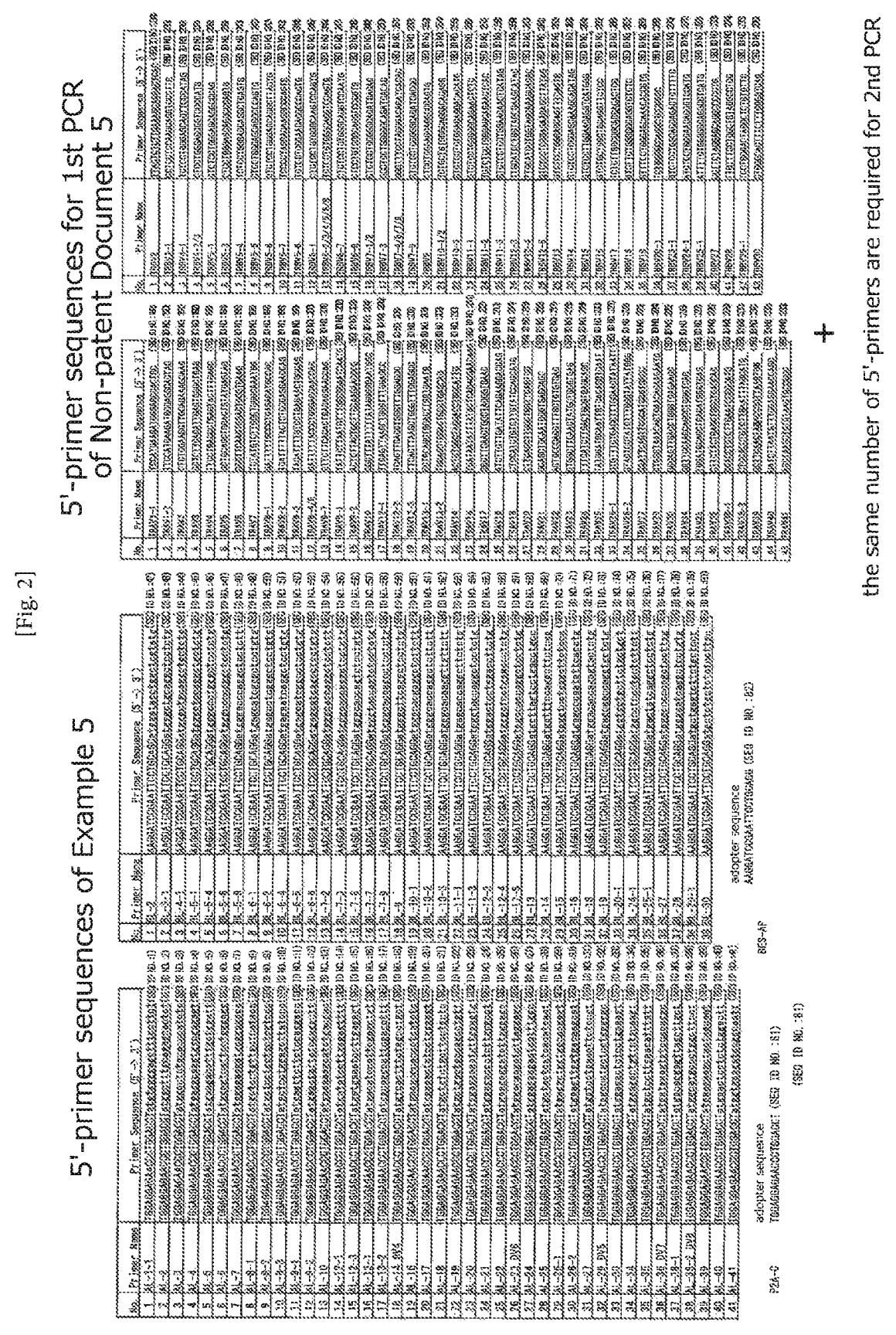

FIG. 2 Comparison of the primer sequences designed in the examples and the primer sequences of the conventional method (Moysey et al., Non-patent document 2, SEQ ID NOS: 189 to 276). In the conventional method, substantially the same number of 5'-primers are required for the second PCR in addition to those for the first PCR indicated here.

FIG. 3 Difference between cDNA obtained by the conventional method (Moysey et al., Non-patent document 2) and cDNA amplified by the method of the present invention. In the method of Moysey et al. (upper diagram), cDNA is amplified for the purpose of expression in *Escherichia coli*. The first PCR is performed by using 5'-primer of a leader sequence not containing translation initiation codon, and then the second PCR is performed by using 5'-primer of a V region to amplify cDNA not containing the region encoding the leader sequence. Although the leader sequence is an unnecessary sequence in the expression system of *Escherichia coli*, it is an indispensable sequence when TCR is expressed in an animal cell. Therefore, cDNA obtained by their method is not suitable for expression in such a cell. In the method of the present invention (lower diagram), by performing the first PCR with a 5'-primer for a leader sequence containing a translation initiation codon, and then performing PCR with a primer for an adaptor sequence added to the primer of the first PCR, cDNA containing a complete leader sequence is amplified.

FIG. 4 Amplification of cDNA using a leader primer. One embodiment of the present invention is schematically shown.

FIG. 5 An example of amplification of TCR cDNAs from single T cells using the 5'-RACE method (conventional method) (Comparative Example). cDNAs were amplified from CD4/CD25-positive T cells. The numerals represent numbers of the individual cells, and NC represents negative control (no cell). The second PCR product (4 µl) was subjected to electrophoresis on 1.5% agarose gel. The amplification ratio of the pair of αβ was 63%.

FIG. 6 An example of amplification of TCR cDNAs from CD4/CD25-positive T cells (Example 1). The numerals represent numbers of the individual cells, and NC represents negative control (no cell). The second PCR product (4 μl) was subjected to electrophoresis on 1.5% agarose gel. The amplification ratio of the pair of αβ was 86.6%.

FIG. 7 An example of amplification of TCR cDNAs from cancer antigen-specific CD8-positive T cell clones (Example 2). The numerals represent numbers of the individual cells, and NC represents negative control (no cell). The second PCR product (4 μl) was subjected to electrophoresis on 1.5% agarose gel. The upper and lower photographs indicate the results obtained with the TCR and TCRβ samples, respectively, wherein amplification of cDNAs of single length is observed.

FIG. 8 An example of amplification of TCR cDNAs from CD4-positive T cells (Example 3). The numerals represent numbers of the individual cells, a represents TCRα, b represents TCRβ, and NC represents negative control (no cell). The second PCR product (4 μl) was subjected to electrophoresis on 1.5% agarose gel. Amplification of cDNA was observed with 13 samples but of 15 samples for TCRα, and with all the samples for TCRβ. The amplification ratio of the pair of ail was 86.7%.

FIG. 9 An example of amplification of TCR cDNAs from CD8-positive T cells (Example 4). The numerals represent numbers of the individual cells, a represents TCRα, b represents TCRβ, and NC represents negative control (no cell). The second PCR product (4 μl) was subjected to electrophoresis on 1.5% agarose gel. The amplification ratio of the pair of αβ was 84%.

Figure 10A:
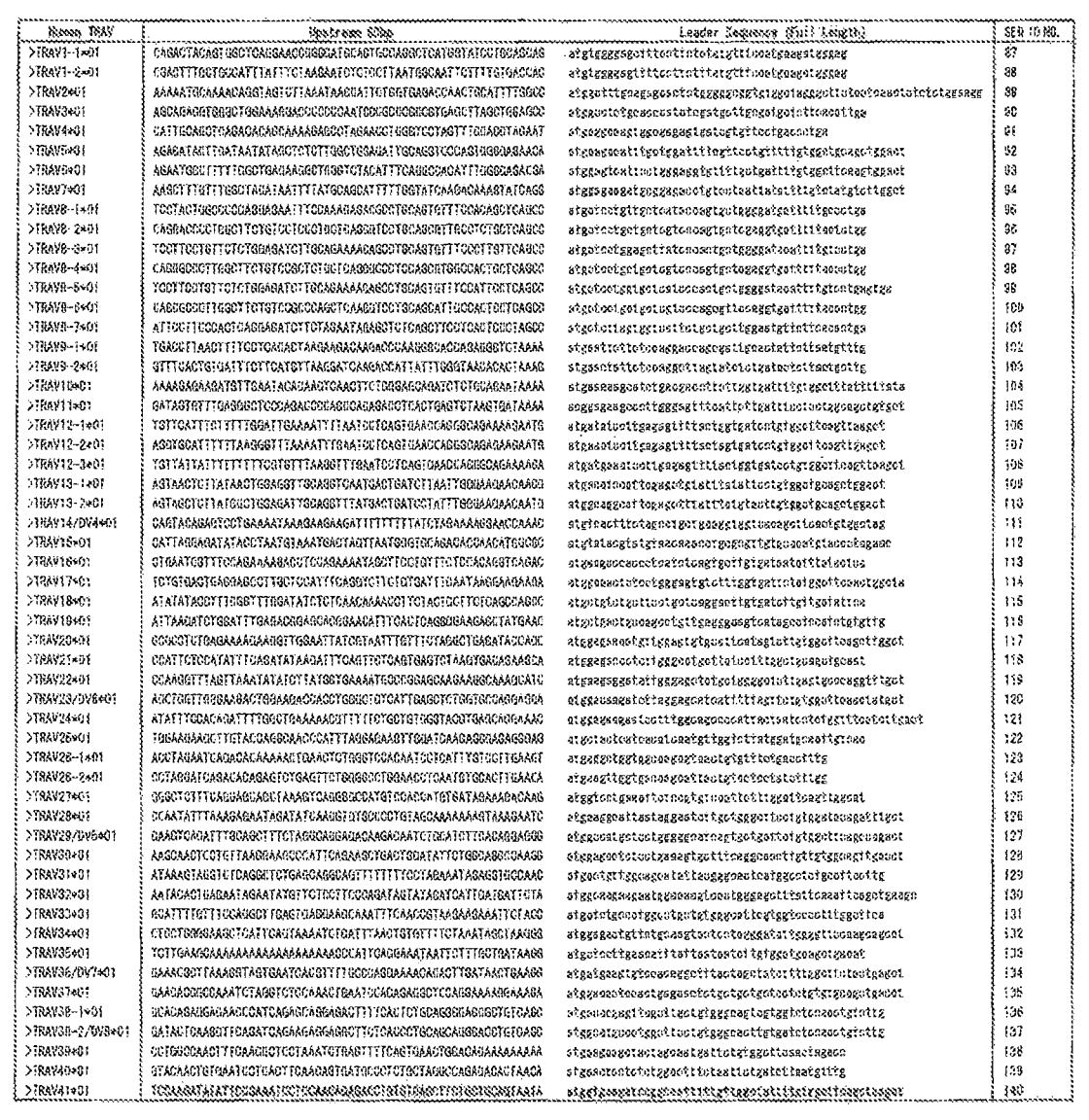
Figure 10B:
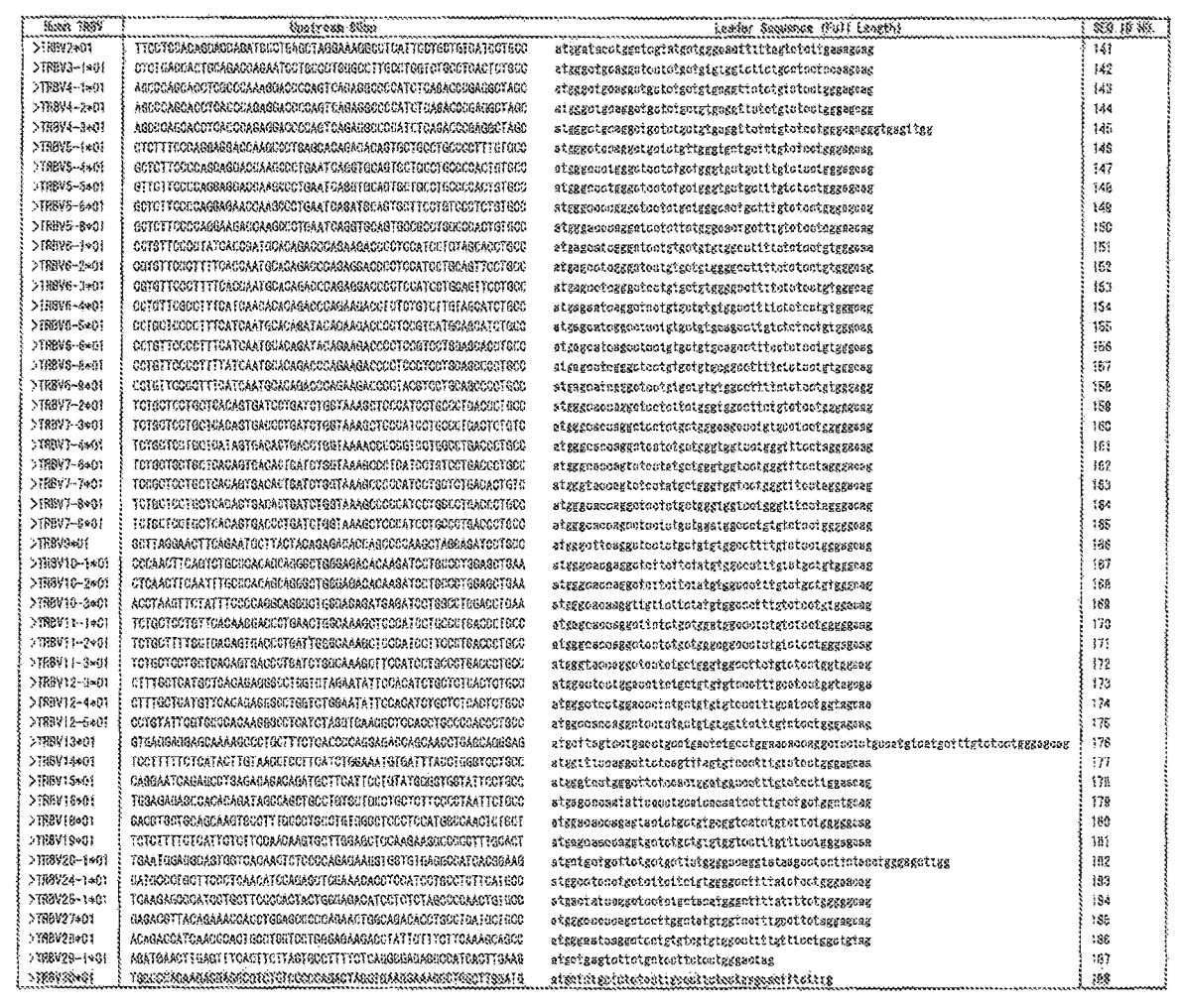

FIG. 10A Sequences around the human TCRα translation initiation codon (SEQ ID NOS: 87 to 140)

FIG. 10B Sequences around the human TCRβ translation initiation codon (SEQ ID NOS: 141 to 188)

FIG. 11 An example of amplification of TCR cDNAs from human CD8-positive T cells using the one-step RT-PCR method. The numerals represent numbers of the individual cells, and NC represents negative control (no cell). The second PCR products (4 μl) for TCRα and TCRβ were separately subjected to electrophoresis on 1.5% agarose gel. The amplification ratio of the pair of TCRαβ was 93%.

FIG. 12 An example of amplification of complete TCR cDNAs from human CD8-positive T cells using the one-step RT-PCR method. The numerals represent numbers of the individual cells, and NC represents negative control (no cell). The second PCR products (4 μl) for TCRα and TCR were separately subjected to electrophoresis on 1.0% agarose gel. The amplification ratio of the pair of TCRα was 92%.

FIG. 13 Table of the sequences of the primers designed in Example 7 (mAL SEQ ID NOS: 283 to 328; mBL, SEQ ID NOS: 329 to 350)

FIG. 14 An example of amplification of TCR cDNAs from mouse CD4-positive T cells using the one-step RT-PCR method. The numerals represent numbers of the individual cells, and NC represents negative control (no cell). The second PCR products (4 μl) for TCRα and map were separately subjected to electrophoresis on 1.5% agarose gel. The amplification ratio of the pair of TCRαβ was 88%.

MODES FOR CARRYING OUT THE INVENTION

When a numerical value range is indicated as "x to y", the range includes the numerical values of x and y as the minimum and maximum values, unless especially indicated.

The expression "a and/or b" mean at least one of a and b, including only a, only b, and both a and b. As for cDNA, amplification means production of cDNA, unless especially indicated. That is, method for amplifying cDNA means a method for producing cDNA, and can also be referred to as method for producing cDNA.

The present invention provides a method for amplifying a T cell receptor (TCR) cDNA, which comprises the following step (1) and step (2):

(1) the step of performing PCR by using at least one kind of the L primer mentioned below, the C primer 1 or UTR primer 1 mentioned below, and cDNA obtained from a single cell as the template to obtain an amplification product 1;

an L primer of 30- to 60-nucleotide length comprising an adapter part of 15- to 25-nucleotide length, and a leader region-annealing part of 15- to 25-nucleotide length, which is ligated downstream from the adapter part, and can anneal to a part of a leader region containing a translation initiation codon, or an upstream part thereof, a C primer 1 of 15- to 25-nucleotide length, which can anneal to a part of a constant region, or a UTR primer 1 of 15- to 25-nucleotide length, which can anneal to a part of a 3' untranslated region, (2) the step of performing PCR by using the adaptor primer mentioned below, the C primer 2 or UTR primer 2 mentioned below, and the amplification product 1 as the template to obtain an amplification product 2;

an adapter primer of 15- to 25-nucleotide length, which can anneal to the adapter part of the amplification product 1, a C primer 2, which can anneal to a part of the constant region existing upstream from the region to which the C primer 1 anneals, or a UTR primer 2 of 15- to 25-nucleotide length, which can anneal to a part of the 3' untranslated region existing upstream from the region to which the UTR primer 1 anneals.

As for such an expression that a certain primer can anneal to a part existing upstream from a region to which another certain primer (primer X) anneals, the upstream means the side on which a DNA chain extends with the primer X (it can also be referred to as 3' side), as seen from the positional relationship of the C primer 1 and C primer 2 shown in FIG. 4, which schematically shows one embodiment of the present invention. A primer "that can anneal to a part existing upstream from a region to which (primer X) anneals" can anneal to the amplification product amplified with the primer X. A primer "that can anneal to a part existing upstream from a region to which (primer X) anneals" can also be referred to as a primer "that can anneal to a part existing inside a region to which (primer X) anneals", a primer "that can anneal to a part existing on the side of extension attained with the primer X with respect to a region to which (primer X) anneals", or a primer "that can anneal to a part existing on the 3' side of a region to which (primer X) anneals". The meaning of the "inside" used above is the same as that used for explanation of the nested PCR, which is multi-stage PCR performed with one primer pair and another second primer pair, and in which the second primer pair is designed for sequences existing inside of sequences for the former primer pair on a target sequence to be amplified, and the meaning of the term is apparent to those skilled in the art.

[Step (1)]

In the step (1), the following primers are used:

an L primer of 30- to 60-nucleotide length comprising an adapter part of 15- to 25-nucleotide length, and a leader region-annealing part of 15- to 25-nucleotide length, which is ligated downstream from the adapter part, and can anneal to a part of a leader region containing a translation initiation codon, or an upstream part thereof, a C primer 1 consisting of a nucleotide sequence of 15- to 25-nucleotide length, which can anneal to a part of a constant region, or a UTR primer 1 of 15- to 25-nucleotide length, which can anneal to a part of a 3' untranslated region.

In the step (1), typically, at least one kind of L primer corresponding to TCRα (AL) and at least one kind of L primer corresponding to TCRβ (BL) are used as the L primer, and a C primer 1 corresponding to TCRα (Ca_RV1) and a C primer 1 corresponding to TCRβ (Cb_RV1) are used as the C primer 1, or a UTR primer 1 corresponding to TCRα (AC_UTR1) and a UTR primer 1 corresponding to TCRβ (BC_UTR1) are used as the UTR primer 1, so that TCRα and TCRβ are simultaneously amplified in one reaction system. In this step, a plurality of kinds of AL primers and a plurality of kinds of BL primers can be made to exist in one reaction system. There are two kinds of genes of the constant region of TCRβ for both human and mouse. Although the DNA sequences of the regions encoding the amino acids are well alike, they show low identity for the UTR part. Therefore, in order to enable amplification of both types of the genes, two kinds of BC_UTR1 (also referred to as BC1_UTR1 and BC2_UTR1) that anneal to each of them, respective ay be used.

These primers can be appropriately designed with reference to the designing methods of the primers of the conventional PCR methods. For the design of PCR primers, software is marketed, and can be used also for the present invention. They can be designed in consideration of primer length, no inclusion of secondary structure in the inside of primer, GC content that should be 40 to 60%, well-balanced distributions of GC-rich regions and AT-rich regions, non-complementariness of their 3' end sequences, no inclusion of self-complementary sequence in each primer itself, and melting temperature (Tm) for annealing.

In a preferred embodiment, an adapter primer can be designed in consideration of convenience for expression of the PCR product to be eventually obtained. For example, the adapter part of AL or BL having a length of 15 to 25 nucleotides may include all or a part of the self-cleaving 2A peptide (P2A) sequence. If it includes such a sequence, when the cloned TCRαβ genes are expressed in a cell, the genes can be expressed as one mRNA of the gene of TCRβ and the gene of TCRα ligated with the P2A sequence (TCRβ-P2A-TCRα or TCRα-P2A-TCRβ). Then, ribosome skip occurs at the position of the P2A sequence, and therefore TCRβ and TCRα are synthesized as separate proteins. In a particularly preferred embodiment, a 15- to 25-mer (preferably 18- to 22-mer) continuous partial sequence of the P2A sequence containing the 3' end can be used as the adapter part. If this sequence is attached to the 5' end of the PCR product, production of the genes as αβ pair will become easy. In another preferred embodiment, the adapter parts of AL or BL having a length of 15 to 25 nucleotides can be a sequence connected with a recognition sequence for a restriction enzyme (for example, BamHI, EcoRI, SbfI). In a particularly preferred embodiment, one of AL and BL contains a partial sequence of P2A, and the other contains a recognition sequence for a restriction enzyme. An example of the sequence of the adapter part containing a partial sequence of P2A is the sequence of SEQ ID NO: 81, and an example of the sequence of the adapter part containing a recognition sequence for a restriction enzyme is the sequence of SEQ ID NO: 82.

In a preferred embodiment, the leader region-annealing part of AL can be designed on the basis of any one of the nucleotide sequences of SEQ ID NOS: 87 to 140. Specifically, the leader region-annealing part of AL may be a part of any one of the nucleotide sequences of SEQ ID NOS: 87 to 140 containing the translation initiation codon (nucleotides of the positions 61 to 63, atg, in the sequences of SEQ ID NOS: 87 to 140), or a part containing a sequence existing upstream from the translation initiation codon of the same. When it contains a sequence existing upstream from the translation initiation codon, the translation initiation codon may be, or may not be contained. Length of the leader region-annealing part of AL can be appropriately designed by those skilled in the art in consideration that it is a primer for PCR, and it can be, for example, 12- to 30-nucleotide length, or may be 13- to 27-nucleotide length, or 15- to 25-nucleotide length.

Irrespective of the configuration of the leader region-annealing part of AL, the leader region-annealing part of BL can be designed on the basis of any one of the nucleotide sequences of SEQ ID NOS: 141 to 188. Specifically, the leader region-annealing part of BL may be a part of any one of the nucleotide sequences of SEQ ID NOS: 141 to 188 containing the translation initiation codon (nucleotides of the positions 61 to 63, atg, in the sequences of SEQ ID NOS: 141 to 188), or a part containing a sequence existing upstream from the translation initiation codon of the same. When it contains a sequence existing upstream from the translation initiation codon, the translation initiation codon may be, or may not be contained. Length of the leader region-annealing part of AL can be appropriately designed by those skilled in the art in consideration that it is a primer for PCR, and it can be, for example, 12- to 30-nucleotide length, or may be 13- to 27-nucleotide length, or 15- to 25-nucleotide length.

In a preferred embodiment, the leader region-annealing part of AL may be one consisting of any one of the nucleotide sequences of SEQ ID NOS: 1 to 41, or any one of the nucleotide sequences of SEQ ID NOS: 283 to 328. Irrespective of the configuration of the leader region-annealing part of AL, the leader region-annealing part of BL may be one consisting of any one of the nucleotide sequences of SEQ ID NOS: 42 to 80, or any one of the nucleotide sequences of SEQ ID NOS: 329 to 350.

In the step (1), 41 kinds of ALs corresponding to the sequences of SEQ ID NOS: 1 to 41, respectively, and 39 kinds of BLs corresponding to the sequences of SEQ ID NOS: 42 to 80, respectively, may exist in one reaction system. Alternatively, 46 kinds of ALs corresponding to the sequences of SEQ ID NOS: 283 to 328, respectively, and 22 kinds of BLs corresponding to the sequences of SEQ ID NOS: 329 to 350, respectively, may exist in one reaction system. According to the investigations of the inventors of the present invention, even if a plurality of primers simultaneously exist, amplification can be efficiently attained.

The adapter part of the L primer can be appropriately designed by those skilled in the art. The adapter part may contain a sequence that is recognized by a restriction enzyme required for incorporation of an amplified cDNA into a vector, as required. Since the adapter part serves as a region to which the adapter primer anneals in the step (2), it can be designed in consideration of length required for such annealing. The length may be, for example, 12- to 30-nucleotide length, or may be 13- to 27-nucleotide length, or 15- to 25-nucleotide length. An example of the adapter part of AL is one consisting of the nucleotide sequence of SEQ ID NO: 81. An example of the adapter part of BL is one consisting of the nucleotide sequence of SEQ ID NO: 82.

Length of the whole L primer is the total length of the adaptor part, leader region-annealing part, and another part constituting it, as the case may be. It may be 24- to 65-nucleotide length, or 30- to 60-nucleotide length.

In the step (1), a C primer 1 consisting of a nucleotide sequence of 15- to 25-nucleotide length, which can anneal to a part of a constant region, or a UTR primer 1 of 15- to 25-nucleotide length, which can anneal to a part of a 3' untranslated region, is used together with the L primer. Sequences of these primers are preferably chosen from the viewpoint of avoiding amplification of contaminating vector. cDNA of TCR as the end product obtained by the embodiment using the C primer 1 is usually incomplete for the constant region. Therefore, the constant region should be reconstructed by adding the lacked sequences to the PCR product by overlap PCR or homologous recombination, and then the resultant is incorporated into an expression vector. In this procedure, the DNA sequence of the part to be reconstructed is usually designed so as to have a DNA sequence in which codons are optimized on the basis of codon usage of human genes. By designing the C primer I so that the part where nucleotide sequences of the codon-optimized sequence and the wild-type sequence differ from each other is a 3' end sequence, amplification by PCR occurs only from DNA having the wild-type constant region. cDNA of TCR as the product obtained by the embodiment using the UTR primer 1 is usually a complete cDNA containing a stop codon.

Length of the whole C primer 1 or UTR primer 1 may be 12- to 30-nucleotide length, or may be 15- to 25-nucleotide length. An example of Ca_RV1 is a polynucleotide consisting of the nucleotide sequence of SEQ ID NO: 83 or SEQ ID NO: 351. An example of Cb_RV1 is a polynucleotide consisting of the nucleotide sequences of SEQ ID NO: 84, or SEQ ID NO: 353, and SEQ ID NO: 354. An example of AC_UTR1 is a polynucleotide consisting of the nucleotide sequence of SEQ ID NO: 277. An example of BC_UTR1 is a polynucleotide consisting of the nucleotide sequence of SEQ ID NO: 279 and/or SEQ ID NO: 280.

Any of the primers used in the step (1) can be synthesized by a known method.

The step (1) is a step of performing PCR by using the aforementioned primers and cDNA obtained from a single cell as the template to obtain the amplification product 1. In order to specify the target T cell and sort a single cell thereof into a container for PCR, there can be used various existing means, for example, flow cytometry, or immunospot assay (immunospot-array assay on a chip, ISAAC) method using a special tip.

Flow cytometry is typically used for sorting cells positive for both two kinds of focused surface markers. One of the two kinds of surface markers may be CD4 or CD8, and therefore anti-CD4 antibody or anti-CD8 antibody can be used for sorting a single target cell. Sorting of a single target cell can also be carried out by the ISAAC method. This method is performed by using a microwell array (tip) having a plurality of wells on one main surface of a substrate with such a size of each well that only one T cell can be contained in each well. For this method, previous patent applications of the inventors of the present invention (for example, Japanese Patent Unexamined Publication (Kokai) No. 2009-34047 (Japanese Patent No. 4148367) can be referred to. For the sorting, antigen, antigen peptide, multi-mer of complexes of MHC molecule and antigen peptide (for example, MHC/p tetramer), and so forth can also be used.

A single cell to be used may be stimulated beforehand under a condition effective for amplification of TCR gene, as required. The condition effective for amplification of TCR gene is such a condition that the T cell is treated so that PCR amplification can be effectively performed, and this condition is usually a condition for increasing mRNA that can serve as the template to such an amount sufficient for performing PCR. This condition may be attained by, for example, maintaining the T cell in the presence of at least IL-2, preferably in the presence of IL-2 and PHA, for a period effective for the treatment. If T cells are maintained as a cell cluster at the time of the stimulation, mRNA that can serve as the template may be effectively increased. As for the stimulation under the condition effective for the amplification of TCR gene, the previous patent applications of the inventors of the present invention (for example, WO2014/017533) can be referred to. According to the examinations of the inventors of the present invention, TCR genes could be amplified according to the present invention without the stimulating treatment for both CD4-positive T cell and CD8-positive T cell.

cDNA of a single cell that serves as the template can be obtained by obtaining mRNA from the cell, and performing reverse transcription reaction with the obtained mRNA. As for the RT-PCR (reverse transcription polymerase chain reaction) method, which amplifies cDNA from mRNA by reverse transcription, there has been developed a method of directly separating mRNA from a cell without performing extraction of total RNA or mRNA. For example, by the method of using magnetic beads coated with oligo(dT), separation of mRNA can completed in a short period of time, and such a method can be preferably used for the present invention.

The conditions for carrying out PCR of the step (1) can be appropriately designed by those skilled in the art. The step (1) can be performed in a system of one to several tens microlitters, and reagents and enzymes used for usual PCR such as buffer, dNTPs and polymerase can be similarly used for the step (1). Although concentrations of the primers are not particularly limited, concentration of each L primer can be 0.01 to 1 μM, and concentration of C primer 1 or UTR primer 1 may be the same as that of the L primer, or several times to several tens of times of that of the L primer, for example, 0.02 to 5 μM. Temperature and time for PCR can be determined to be similar to those used in usual PCR according to type of the polymerase to be used. In order to carry out the step (1), existing PCR apparatuses can be used.

In the step (1), the region existing between the L primer, and C primer 1 or UTR primer 1 is amplified. The obtained amplification product 1 contains the L primer, and C primer 1 or UTR primer 1, and therefore contains the adapter part, translation initiation codon, leader region, V region, and all or a part of constant region. In a preferred embodiment, TCRα and TCRβ are amplified as a pair in the step (1), and therefore the amplification product 1 contains the pair of TCRα and TCRβ, wherein each of TCRα and TCRβ contains the adapter part, translation initiation codon, leader region, V region, and all or a part of constant region.

The reverse transcription reaction for obtaining cDNA used as the template of the step (1) from a single cell, and PCR of the step (1) may be successively performed in separate tubes, or may be continuously performed in the same tube. When they are performed in the same tube, primers specific to the constant region of TCR can be used as the primers for the reverse transcription reaction instead of the dT primers, and the reaction volume for PCR of the step (1) is reduced compared with that of the case where they are performed in separate tubes. Change of these conditions may increase the amplification ratio of the pair of TCRαβ to be finally obtained.

[Step (2)]

In the step (2), the following two kinds of primers are used:

(2) the step of performing PCR by using the adaptor primer mentioned below, the C primer 2 or UTR primer 2 mentioned below, and the amplification product 1 as the template to obtain an amplification product 2;
   an adapter primer of 15- to 25-nucleotide length, which can anneal to the adapter part of the amplification product 1,
   a C primer 2 of 15- to 25-nucleotide length, which can anneal to a part of the constant region existing upstream from the region to which the C primer 1 anneals, or a UTR primer 2 of 15- to 25-nucleotide length, which can anneal to a part of the 3' untranslated region existing upstream from the region to which the UTR primer 1 anneals.

Since the L primer containing the adapter part is used in the step (1), amplification can be performed by using 1 or 2 sets of primer pairs in the step (2).

In the step (2), the adapter primer and C primer 2 (Ca_RV2) or UTR primer 2 (AC_UTR2) for the second stage of the amplification of TCRα can be used, and the adapter primer and the C primer 2 (Cb_RV2) or C primer 2 (BC_UTR2) for the second stage of the amplification of TCRβ can be used. In the step (2), the reaction for amplifying TCRα, and the reaction for amplifying TCRβ may be separately performed. In such a case, an adapter primer and Ca_RV2 or AC_UTR2 for TCRα are used in the reaction system for amplifying TCRα, and an adapter primer and Cb_RV2 or BC_UTR2 for TCRβ are used in the reaction system for amplifying TCRβ. As already described, there are two kinds of genes of the constant region of TCRβ, and the parts of untranslated regions of them show low identity. Therefore, two kinds of BC_UTR2 (also referred to as BC1_UTR2 and BC2_UTR2) that anneal to them, respectively, may be used so that both the genes can be amplified.

The adapter primer can be designed on the basis of the adapter part of the L primer used in the step (1). The length thereof can be, for example, 12- to 30-nucleotide length, or may be 13- to 27-nucleotide length, or 15- to 25-nucleotide length. Although the sequence of the adapter primer is not particularly limited so long as it can anneal to the adapter part, it can be, for example, all or a part of the complementary sequence of the adapter sequence.

The C primer 2 is designed so that it can anneal to a part of the constant region of cDNA of TCR existing upstream from the region to which the C primer 1 anneals. It is preferable to choose the sequence so as to avoid amplification of contaminating vector, as in the case of the design of the C primer 1. The UTR primer 2 is designed so that it can anneal to a part of the 3' untranslated region existing upstream from the region to which the UTR primer 1 anneals.

Length of the whole C primer 2 or UTR primer 2 may be 12- to 30-nucleotide length, or 15- to 25-nucleotide length. An example of Ca_RV2 is one consisting of the nucleotide sequence of SEQ ID NO: 835 or SEQ ID NO: 352. An example of Cb_RV2 is a polynucleotide consisting of the nucleotide sequence of SEQ ID NO: 86 or SEQ ID NO: 355. An example of AC_UTR is a polynucleotide consisting of the nucleotide sequence of SEQ ID NO: 278. An example of BC_UTR2 is a polynucleotide consisting of the nucleotide sequence of SEQ ID NO: 281 and/or SEQ ID NO: 282.

Any of the primers used for the step (2) can be synthesized by a known method.

The conditions for carrying out PCR of the step (2) can be appropriately designed by those skilled in the art. Like the step (1), the step (2) can be performed in a system of one microliter to several tens of microliters, and reagents and enzymes used for usual PCR such as buffer, dNTPs and polymerase can be similarly used for the step (2). Although concentrations of the primers are not particularly limited, concentrations of the adapter primer and C primer 2 can each be, for example, 0.02 to 5 µM. Temperature and time for PCR can be determined to be similar to those used in usual PCR according to type of the polymerase to be used. In order to carry out the step (2), existing apparatuses for PCR can be used.

In the step (2), the region existing between the adapter primer, and the C primer 2 or UTR primer 2 is amplified. The obtained amplification product 2 contains the adapter primer, and the C primer 2 or UTR primer 2, and therefore contains the adapter part, translation initiation codon, leader region, V region, and all or a part of constant region. In a preferred embodiment, TCRα and TCRβ are amplified in separate reaction systems in the step (2), but each of TCRα and TCRβ contains the adapter part, translation initiation codon, leader region, V region, and all or a part of constant region.

If a UTR primer 1 that can anneal to a part of 3' untranslated region is used instead of the C primer 1 in the step (1), and a UTR primer 2 that can anneal to a part of 3' untranslated region is used instead of the C primer 2 in the step (2), by synthesizing IVT RNA in vitro using the obtained PCR product (complete cDNA) as the template, and introducing the obtained IVT RNA into a cell by gene transfer, TCR can be expressed in the cell. If IVT RNA is synthesized by using the PCR product obtained with the C primer 1 as the template, the constant region becomes imperfect, and therefore TCR cannot be expressed in a cell with it. If it is desired to express TCR in a cell using RNA, the method of using the UTR primer 1 is more preferred.

[Kit etc.]

The present invention provides primers, primer sets, and kit for amplifying a TCR cDNA. The kit may comprise, besides the various primers mentioned above, reagents and enzymes required for PCR such as buffer, dNTPs, and polymerase. The kit may also comprise an instruction for using the kit.

The single cell used for amplifying TCR cDNA according to the present invention can be a T cell derived from a subject (patient) with a disease or condition that can be treated by TCR gene therapy. Typical examples of such a disease or condition include cancers and infectious diseases, and preferred examples are cancers. Diseases to which application of the present invention can be expected include cancers and infectious diseases, and the cancers include adult cancers and infant cancers, and include gastrointestinal carcinoma, lung cancer, intractable esophagus cancer, head and neck cancer, ovarian cancer, multiple myeloma, and so forth. The infectious diseases include virus infections (for example, acquired immune deficiency syndrome (AIDS), adult T cell leukemia, Ebola hemorrhagic fever, influenza, viral hepatitis, viral meningitis, yellow fever, cold syndrome, rabies, cytomegalovirus infection, severe acute respiratory syndrome (SARS), progressive multifocal leucoencephalopathy, varicella, herpes zoster, hand, foot and mouth disease, dengue fever, erythema infectiosum, infectious mononucleosis, smallpox, German measles, acute anterior poliomyelitis (polio), measles, pharyngoconiunctival fever (swimming-pool sickness), Marburg hemorrhagic fever, hantavirus hemorrhagic fever with renal syndrome, Lassa fever, mumps, West Nile fever, herpangina, and chikungunya hemorrhagic fever), bacterial infections, rickettsial infections, parasitic infections, and prion disease. The "treatment" includes reduction of onset risk, prophylactic treatment, therapeutic treatment, and suppression of advance, unless especially indicated.

[Comparison with Conventional Methods etc.]

As described above, the amplification method of the present invention that comprises the step (1) and (2), and carried out in two steps differs from conventional methods in various aspects. Such differences in contrast to conventional methods will be explained with reference to FIG. 3.

In the conventional method of Moysey et al. (Non-patent document 2, upper diagram of FIG. 3), cDNA is amplified for the purpose of expression in *Escherichia coli*. PCR of the first stage is performed by using a 5'-primer for the leader sequence not containing translation initiation codon, and then PCR of the second stage is performed by using a 5'-primer for the V region to amplify cDNA that does not contain any region encoding a leader sequence. Although leader sequence is an unnecessary sequence in the expression system of *Escherichia coli*, it is an indispensable sequence when TCR is expressed in an animal cell. Therefore, cDNA obtained by their method is not suitable for expression in such a cell. In order to express an obtained TCR cDNA in such a cell, a leader sequence must be separately added. In contrast, in the method of the present invention (lower diagram of FIG. 3), PCR of the first stage is performed by using a 5'-primer for a leader sequence containing a translation initiation codon, and then PCR of the second stage is performed by using an adapter primer that anneals to the adapter part added to the L primer used in the first stage. Therefore, TCR cDNA having complete leader region can be amplified.

In the conventional method, about 500 cells are required for amplifying TCR, and TCR cannot be amplified from single T cell. Therefore, in order to obtain cancer-specific TCR from a cancer-specific T cell, it is necessary to prepare a clone of the cancer-specific T cell, proliferate it, and amplify the gene of TCR from about 500 cells, and it takes much time (about three months). In contrast, according to the amplification method of the present invention, TCR cDNA can be efficiently amplified from a single T cell, it is unnecessary to obtain T cell clone for obtaining cancer-specific TCR, and a cancer-specific TCR cDNA can be obtained and verified within ten days in the shortest case.

A more detailed example of the amplification of TCR cDNA according to the present invention is schematically shown in FIG. 4. Hereafter, the present invention will be explained with reference to comparative examples and examples.

EXAMPLES

RT-PCR Comparative Example

Amplification of TCR cDNA from single CD4/CD25-positive T cells was attempted by using the 5'-RACE method (conventional method). It was performed according to the method of Non-patent document 1. The results are shown in FIG. 5. The amplification ratio of the pair of 41 was 63%. The length of the amplification product was not uniform.

[Design of PCR Primers]

The leader peptide sequences of human TCRs were obtained from IMGT (http://www.imgt.org), and oligonucleotides consisting of a sequence of 20 nucleotides containing a translation initiation codon to which the adapter sequence was added were synthesized as leader primers. Except for those having the same sequence, 41 kinds and 39 kinds of leader primers were finally synthesized for α and β, respectively (FIG. 1). In PCR, TCR cDNA was amplified with a combination of any of the following constant primers, which were designed from a constant region, and leader primers.

```
Ca_RV1:
                                    (SEQ ID NO: 83)
AGGTTCGTATCTGTTTCAAAGCTT

Ca_RV2:
                                    (SEQ ID NO: 84)
GGTAAAGCCACAGTCTGCTCTA

Cb_RV1:
                                    (SEQ ID NO: 85)
TGTGACACATTTGTTTGAGAA

Cb_RV2:
                                    (SEQ ID NO: 86)
CTGTGCACCTCCTTCCCA
```

RT-PCR Example 1

1. Acquisition of CD4/CD25-Positive Single T Cells

Peripheral blood lymphocytes were isolated from human peripheral blood by using Lymphosepar. I (IBL), and stained with anti-CD4 antibodies and anti-CD25 antibodies, and then CD4/CD25-positive single cells were each obtained in 7 µl of lysis buffer [10 to 35 µg of Dynabeads dT(25), 7 µl of Lysis/Binding Buffer (Dynabeads mRNA Direct Kit, Ambion)] contained in a PCR tube by using a cell sorter FACS Aria (BD). The obtained samples were cryopreserved in a freezer at −80° C.

2. Reverse Transcription Reaction

Each sample obtained by the process of the above section 1 was thawed, stirred, incubated at room temperature for 5 minutes, then set on DynaMag-96 Side Magnet (Life Technologies), and left standing for 20 seconds, and the lysis buffer was removed. Then, 10 µl of 10 mM Tris-Cl, pH 8.5 was added to the beads to suspend them, the suspension was set on DynaMag-96 Side Magnet again, and left standing for 20 seconds, and 10 mM Tris-Cl, pH 8.5 was removed. For the synthesis of cDNA, PrimeScriptII 1st strand cDNA Synthesis Kit (TaKaRa) was used. An RT reaction mixture [13.5 µL of RNase free dH$_2$O, 4.0 µl of 5×PrimeScript II Buffer, 1.0 µl of dNTP mixture (10 mM each), 1.0 µl of PrimeScript II RTase (200 U/µl), 0.5 µl of RNase Inhibitor (40 U/µl)] in a volume of 5 µl was added to each PCR tube, the mixture was stirred, and set on GeneAmp PCR System 2700 (Applied Biosystems), and the reverse transcription reaction was allowed at 42° C. for 60 minutes.

3. First PCR

The RT reaction mixture obtained by the process of the above section 2 was set on DynaMag-96 Side Magnet, and left standing for 20 seconds, the RT reaction mixture was removed, 10 µl of 1st PCR reaction mixture [10.0 µl of 2×PrimeStar GC Buffer (TaKaRa), 1.7 µl of H$_2$O, 1.6 µl of 2.5 mM dNTP, 0.4 µl of AL primer mix (2 µM each), 0.4 µl of BL primer mix (2 µM each), 0.4 µl of Ca_RV1 (10 µM), 0.4 µl of Cb_RV1(10 µM), 0.1 µl of PrimeStar HS DNA Polymerase (TaKaRa)] was added to the residue, and the mixture was stirred. The reactions were performed on GeneAmp PCR System 2700 (Applied Biosystems) at 98° C. for 1 minute, and then at 98° C. for 10 seconds, 50° C.

for 5 seconds, and 72° C. for 40 seconds for 35 cycles. AL means a leader primer for TCRα, and BL means a leader primer for TCRβ.

4. Second PCR

The first PCR reaction mixture obtained by the process of the above section 3 was diluted 10 times with H₂O, 2 µl of the diluted reaction mixture was added to 18 µl of a second PCR reaction mixture contained in a PCR tube, and the mixture was stirred. The reactions were performed at 98° C. for 1 minute, and then at 98° C. for 10 seconds, 52° C. for 5 seconds, and 72° C. for 30 seconds for 35 cycles. In the second PCR, TCRα and TCRβ were amplified in separate tubes by using primers for the adaptor sequence added to the leader primer, P2A-C and BES-AP (FIG. 1), and a constant primer. Compositions of the second PCR reaction mixtures were as follows.

TCRα second PCR solution: 10.0 µl of 2×PrimeStar GC Buffer, 5.5 µl of H₂O, 1.6 µl of 2.5 mM dNTP, 0.4 µl of P2.A-C (10 µM), 0.4 µl of Ca_RV2 (10 µM); 0.1 µl of PrimeStar HS DNA Polymerase TCRβ second PCR solution: 10.0 µl of 2×PrimeStar GC Buffer, 5.5 µl of H₂O, 1.6 µl of 2.5 mM dNTP, 0.4 µl of BES-AP (10 µM), 0.4 µl of Cb_RV2 (10 µM), 0.1 µl of PrimeStar HS DNA Polymerase 5. Confirmation of Amplification of TCR cDNA The reaction mixture obtained by the process of the above section 4 (4 µl) was subjected to electrophoresis using 1.5% agarose gel to confirm amplification of the PCR product. The results are shown in FIG. 6. The amplification ratio of the pair of αβ was 86.6%.

RT-PCR Example 2

1. Acquisition of Cancer Antigen-Specific CD8-Positive Single T Cells

Cancer antigen-specific T cell clones activated by antigen stimulation were stained with anti-CD8 antibodies, and then CD8-positive single cells were each obtained in 3 µl of a primer mix [0.25 µl of oligo dT primer (50 µM), 1.0 µl of dNTP mixture (2.5 mM each), 1.75 µl of RNase free dH₂O] contained in a PCR tube by using a cell sorter FACS Aria (BD). The obtained samples were cryopreserved in a freezer at −80° C.

2. Reverse Transcription Reaction

For the synthesis of cDNA, PrimeScriptII 1st strand cDNA Synthesis Kit (TaKaRa) was used. Each sample obtained by the process of the above section 1 was thawed, stirred, incubated at 65° C. for 5 minutes, and quickly cooled on ice. An RT reaction mixture [2 µl of RNase free dH₂O, 1 µl of 5×PrimeScript II Buffer, 1.0 µl of PrimeScript II RTase (200 U/µl), 2 µl of RNase inhibitor (40 U/µl)] in a volume of 2 µl was added to each PCR tube, the mixture was stirred, and set on GeneAmp PCR System 2700 (Applied Biosystems), the reverse transcription reaction was allowed at 42° C. for 60 minutes, and the enzyme was inactivated at 70° C. for 15 minutes.

3. First PCR

To 5 µl of the RT reaction mixture obtained by the process of the above section 2 contained in each PCR tube, 15 µl of 1st PCR reaction mixture [10.0 µl of 2×PrimeStar GC Buffer (TaKaRa), 1.7 µl of H₂O, 1.6 µl of 2.5 mM dNTP, 0.4 µl of AL primer mix (2 µM each), 0.4 µl of BL primer mix (2 µM each), 0.4 µl of Ca_RV1 (10 µM), 0.4 µl of Cb_RV1 (10 µM), 0.1 µl of PrimeStar HS DNA Polymerase (TaKaRa)] was added, and the mixture was stirred. The reactions were performed on GeneAmp PCR System 2700 (Applied Biosystems) at 98° C. for 1 minute, and then at 98° C. for 10 seconds, 50° C. for 5 seconds, and 72° C. for 40 seconds for 35 cycles.

4. Second PCR

The second PCR was performed in the same manner as that of the section 4 of Example 1.

5. Confirmation of Amplification of TCR cDNA

The confirmation was performed in the same manner as that of the section 5 of Example 1. The results are shown in FIG. 7. Amplification of cDNA of single length was observed.

RT-PCR Example 3

1. Acquisition of CD4-Positive Single T Cells

Peripheral blood lymphocytes were isolated from human peripheral blood by using Lymphosepar 1 (IBL), and stained with anti-CD4 antibodies, and then CD4-positive single cells were obtained in empty PCR tubes by using a cell sorter FACS Aria (BD). The obtained samples were cryopreserved in a freezer at 80° C.

2. Reverse Transcription Reaction

For the synthesis of cDNA, PrimeScriptII 1st strand cDNA Synthesis Kit (TaKaRa) was used. An RT reaction mixture [12.5 µl of RNase free dH₂O, 4.0 µl of 5×PrimeScript II Buffer, 1.0 µl of dNTP mixture (10 mM each), 1.0 µl of oligo dT primer (50 µM), 1.0 µl of PrimeScript II RTase (200 U/µl), 0.5 µl of RNase inhibitor (40 U/µl)] in a volume of 5 µl was added to each PCR tube obtained from the process of the above section 1, the mixture was stirred, and set on GeneAmp PCR System 2700 (Applied Biosystems), and the reverse transcription reaction was allowed at 42° C. for 60 minutes.

3. First PCR

The first PCR was performed in the same manner as that of the section 3 of Example 2.

4. Second PCR

The second PCR was performed in the same manner as that of the section 4 of Example 1.

5. Confirmation of Amplification of TCR cDNA

The confirmation was performed in the same manner as that of the section 5 of Example 1. The results are shown in FIG. 8. Amplification of cDNA was observed for 13 samples out of 15 samples for TCRα, and all the samples for TCRβ, and the amplification ratio of the pair of αβ was 86.7%.

RT-PCR Example 4

1. Acquisition of CD8-Positive Single T Cells

Peripheral blood lymphocytes were isolated from human peripheral blood by using Lymphosepar I (IBL), and stained with anti-CD8 antibodies, and then CD8-positive single cells were obtained in empty PCR tubes by using a cell sorter FACS Aria (BD). The obtained samples were cryopreserved in a freezer at 80° C.

2. Reverse Transcription Reaction

The reverse transcription reaction was performed in the same manner as that of the section 2 of Example 3.

3. First PCR

The first PCR was performed in the same manner as that of the section 3 of Example 2.

4. Second PCR

The second PCR was performed in the same manner as that of the section 4 of Example 1.

5. Confirmation of Amplification of TCR cDNA

The confirmation was performed in the same manner as that of the section 5 of Example 1. The results are shown in FIG. 9. The amplification ratio of the pair of TCRαβ was 84%.

RT-PCR Example 5

1. Acquisition of CD8-Positive Single T Cells

Peripheral blood lymphocytes were isolated from human peripheral blood by using Lymphosepar I (IBL), and stained with anti-CD8 antibodies, and then CD8-positive single cells were obtained in empty PCR tubes by using a cell sorter FACS Aria (BD). The obtained samples were cryopreserved in a freezer at −80° C.

2. One-Step RT-PCR

In order to continuously perform the reverse transcription reaction and first PCR, an RT-PCR reaction mixture [2.5 μl of 2×PrimeSTAR GC Buffer, 1.475 μl of RNase free dH$_2$O, 0.1 μl of AL primer mix (2 μM each), 0.1 μl of BL primer mix (2 μM each), 0.1 μl of Ca_RV1 (10 μM), 0.1 μl of Ca_RV1 (10 μM), 0.4 μl of 2.5 mM dNTP, 0.1 μl of RNase inhibitor (40 U/μl), 0.1 μl of PrimeScript II RTase (200 U/μl), 0.025 μl of PrimeStar HS DNA Polymerase (TaKaRa)] in a volume of 5 μl was added to each PCR tube obtained from the process of the above section 1, the mixture was stirred, and set on GeneAmp PCR System 2700 (Applied Biosystems), and the reactions were performed at 45° C. for 40 minutes, 98° C. for 1 minute, and then at 98° C. for 10 seconds, 52° C. for 5 seconds, and 72° C. for 1 minute for 30 cycles. Thus, the reverse transcription reaction and first PCR were continuously performed in the same tube.

3. Second PCR

The second PCR was performed in the same manner as that of the section 4 of Example 1.

4. Confirmation of Amplification of TCR cDNA

The confirmation was performed in the same manner as that of the section 5 of Example 1. The results are shown in FIG. 11. The amplification ratio of the pair of TCRβ was 93%.

RT-PCR Example 6

1. Acquisition of CD8-Positive Single T Cells

Peripheral blood lymphocytes were isolated from human peripheral blood by using Lymphosepar I (IBL), and stained with anti-CD8 antibodies, and then CD8-positive single cells were obtained in empty PCR tubes by using a cell sorter FACS Aria (BD). The obtained samples were cryopreserved in a freezer at 80° C.

2. One-Step RT-PCR

In order to amplify complete cDNA containing a sequence from the start codon to the stop codon, RT-PCR was performed by using the following primers designed on the basis of 3' untranslated regions.

```
AC_UTR1:
                                (SEQ ID NO: 277)
AGAGCTGAGAAGAGGGGCAAT

AC_UTR2:
                                (SEQ ID NO: 278)
AGGGAGCACAGGCTGTCTTA

BC1_UTR1:
                                (SEQ ID NO: 279)
CTGGCAAAAGAAGAATGTGT

BC2_UTR1:
                                (SEQ ID NO: 280)
ACACAGATTGGGAGCAGGTA

BC1_UTR2:
                                (SEQ ID NO: 281)
CCATGACGGGTTAGAAGCTC

BC2_UTR2:
                                (SEQ ID NO: 282)
GGATGAAGAATGACCTGGGAT
```

In order to continuously perform the reverse transcription reaction and first PCR, an RT-PCR reaction mixture [2.5 μl of 2×PrimeSTAR GC Buffer, 1.375 μl of RNase free dH$_2$O, 0.1 μl of AL primer mix (2 μM each), 0.1 μl of BL primer mix (2 μM each), 0.1 μl of AC_UTR1 (10 μM), 0.1 μl of BC1_UTR1 (10 μM), 0.1 μl of BC2_UTR1 (10 μM), 0.4 μl of 2.5 mM dNTP, 0.1 μl of RNase inhibitor (40 U/μl), 0.1 μl of PrimeScript II RTase (200 U/μl), 0.025 μl of PrimeStar HS DNA Polymerase (TaKaRa)] in a volume of 5 μl was added to each PCR tube obtained from the process of the above section 1, the mixture was stirred, and set on GeneAmp PCR System 2700 (Applied Biosystems), and the reactions were performed at 45° C. for 40 minutes, 98° C. for 1 minute, and then at 98° C. for 10 seconds, 52° C. for 5 seconds, and 72° C. for 1 minute for 30 cycles. Thus, the reverse transcription reaction and first PCR were continuously performed in the same tube.

3. Second PCR

The first PCR reaction mixture obtained from the process of the above section 2 was diluted 10 times with H$_2$O, 2 μl of the diluted reaction mixture was added to 18 μl of a second PCR reaction mixture contained in a PCR tube, and the mixture was stirred. The reactions were performed at 98° C. for 1 minute, and then at 98° C. for 10 seconds, 52° C. for 5 seconds, and 72° C. for 30 seconds for 35 cycles. In the second PCR, TCRα and TCRβ were amplified in separate tubes by using primers for the adaptor sequence added to the leader primer, P2A-C and BES-AP (FIG. 1), and a 3' UTR primer. Compositions of the second PCR reaction mixtures were as follows.

TCRα second PCR solution: 10.0 μl of 2×PrimeStar GC Buffer, 5.5 μl of H$_2$O, 1.6 μl of 2.5 mM. dNTP, 0.4 μl of P2A-C (10 μM), 0.4 μl of AC_UTR2 (10 μM), 0.1 μl of PrimeStar HS DNA Polymerase TCRβ second PCR solution: 10.0 μl of 2×PrimeStar GC Buffer, 5.1 μl of H$_2$O, 1.6 μl of 2.5 mM dNTP, 0.4 μl of BES-AP (10 μM), 0.4 μl of BC1_UTR2 (10 μM), 0.4 μl of BC2_UTR2 (10 μM), 0.1 μl of PrimeStar HS DNA Polymerase 4. Confirmation of Amplification of TCR cDNA The confirmation was performed in the same manner as that of the section 5 of Example 1. The results are shown in FIG. 12. The amplification ratio of the pair of TCRαβ was 92%.

RT-PCR Example 7

1. Design of Primers for Mouse TCR

Figure 13:
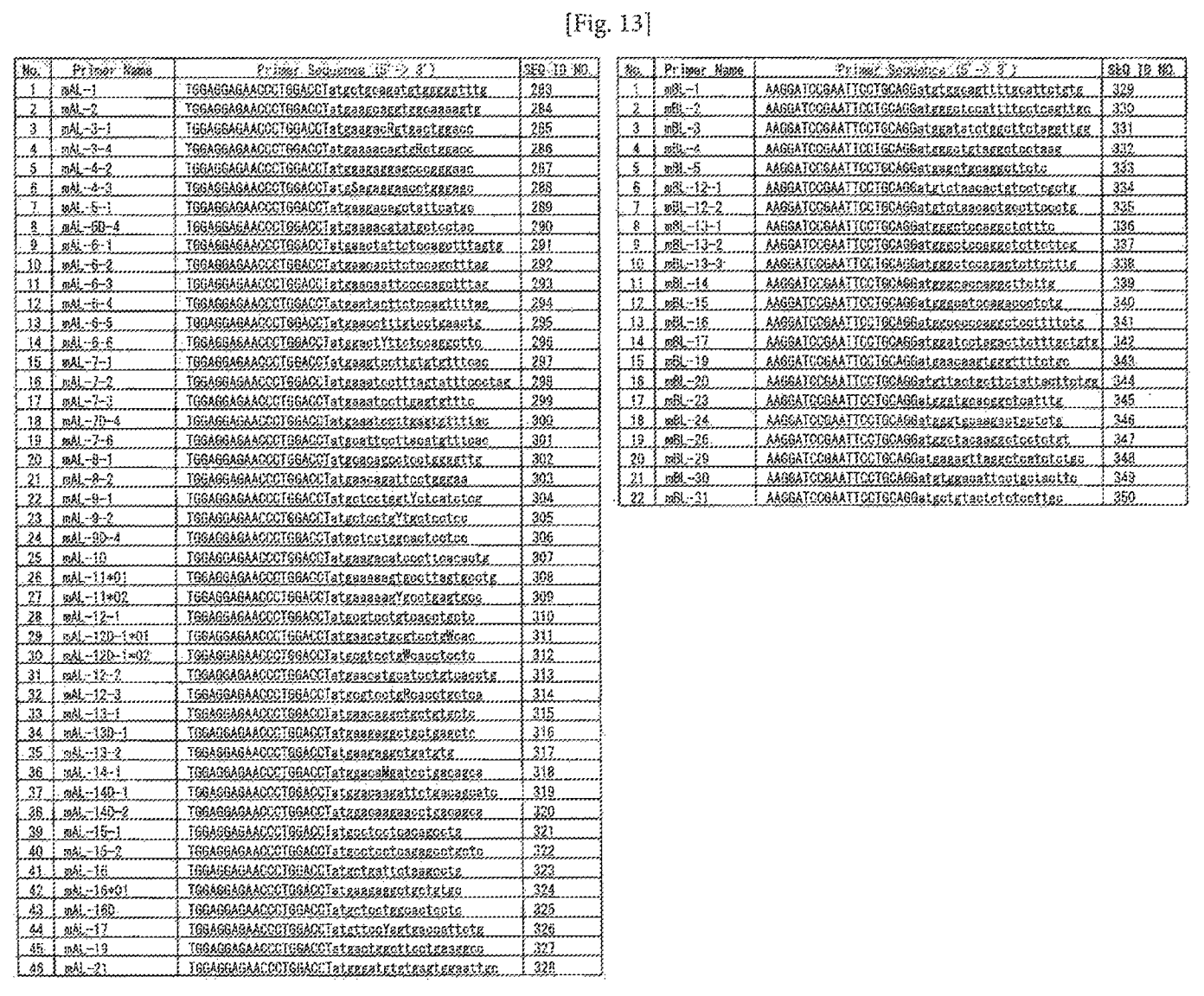

Leader primers were designed in the same manner as that used for human TCR. The sequences thereof are shown in FIG. 13. The sequences of the constant primers for the constant region are shown below.

```
mCa_RV1:
                                (SEQ ID NO: 351)
CATCACAGGGAACGTCTGAACTG
```

-continued mCa_RV2:
(SEQ ID NO: 352)
TCGGCACATTGATTTGGGAGTCA mCb1_RV1:
(SEQ ID NO: 353)
GTAATCCCACAGTCTGCTCG mCb2_RV1:
(SEQ ID NO: 354)
GTGATTCCACAGTCTGCTCG mCb_RV2:
(SEQ ID NO: 355)
CAAGCACACGAGGGTAGCCTTT 2. Acquisition of Mouse CD4-Positive T Cells Lymphocytes were isolated from a mouse spleen, and stained with anti-CD4 antibodies, and then CD4-positive single cells were obtained in empty PCR tubes by using a cell sorter FACS Aria (BD). The obtained samples were cryopreserved in a freezer at 80° C.

3. One-Step RT-PCR

In order to continuously perform the reverse transcription reaction and first PCR, an RT-PCR reaction mixture [2.5 µl of 2×PrimeSTAR GC Buffer, 1.425 µl of RNase free dH₂O, 0.1 µl of mAL primer mix (2 µM each), 0.1 µl of mBL primer mix (2 µM each), 0.1 µl of mCa_RV1 (10 µM), 0.075 µl of mCb1_RV1 (10 µM), 0.075 µl of in Cb2RV1 (10 µM), 0.4 µl of 2.5 mM dNTP, 0.1 µl of RNase inhibitor (40 U/µl), 0.1 µl PrimeScript II RTase (200 U/µl), 0.025 µl of PrimeStar HS DNA Polymerase (TaKaRa)] in a volume of 5 µl was added to each PCR tube obtained from the process of the above section 1, the mixture was stirred, and set on GeneAmp PCR System 2700 (Applied Biosystems), and the reactions were performed at 45° C. for 40 minutes, 98° C. for 1 minute, and then at 98° C. for 10 seconds, 52° C. for 5 seconds, and 72° C. for 1 minute for 30 cycles. Thus, the reverse transcription reaction and first PCR were continuously performed in the same tube.

4. Second PCR

The second PCR was performed in the same manner as that of the section 4 of Example 1 by using mCa_RV2 and mCb_RV2 instead of Ca_RV2 and Cb_RV2, respectively.

5. Confirmation of Amplification of TCR cDNA

The confirmation was performed in the same manner as that of the section 5 of Example 1. The results are shown in FIG. 14. The amplification ratio of the pair of TCRαβ was 88%.

Sequence Listing Free Text

SEQ ID NOS: 1 to 41-ALs
SEQ ID NOS: 42 to 80-BLs
SEQ ID NOS: 81-P2A-C
SEQ ID NOS: 82-BES-AP
SEQ ID NOS: 83-Ca_RV1
SEQ ID NOS: 84-Ca_RV2
SEQ ID NOS: 85-Cb_RV1
SEQ ID NOS: 86-Cb_RV2
SEQ ID NOS: 87 to 140-Sequences around TCRα translation initiation codon (upstream 60 bp+full length leader sequence)
SEQ ID NOS: 141 to 188-Sequences around TCRβ translation initiation codon (upstream 60 bp+full length leader sequence)
SEQ ID NOS: 189 to 276-5' primers for first PCR of the conventional method
SEQ ID NOS: 277-AC_UTR1
SEQ ID NOS: 278-AC_UTR2
SEQ ID NOS: 279-BC1_UTR1
SEQ ID NOS: 280-BC2_UTR1
SEQ ID NOS: 281-BC1_UTR2
SEQ ID NOS: 282-BC2_UTR2
SEQ ID NOS: 283 to 328-mALs
SEQ ID NOS: 329 to 350-mBLs
SEQ ID NOS: 351-mCa_RV1
SEQ ID NOS: 352-mCa_RV2
SEQ ID NOS: 353-mCa_RV1
SEQ ID NOS: 354-mCb_RV1
SEQ ID NOS: 355-mCb_RV2

The invention claimed is:

1. A method for amplifying a T cell receptor (TCR) cDNA, which comprises the following step (1) and step (2):
   (1) the step of performing PCR by using at least one kind of the L primer mentioned below, the C primer 1 or UTR primer 1 mentioned below, and a TCR cDNA obtained from a single cell as the template to obtain an amplification product 1;
   an L primer of 30- to 60-nucleotide length comprising an adapter part of 15- to 25-nucleotide length, and a leader region-annealing part of 15- to 25-nucleotide length, which is ligated downstream from the adapter part, and can anneal to a part of a leader region of the TCR cDNA which contains a translation initiation codon, or to a part of the TCR cDNA which is an upstream part of the leader region,
   a C primer 1 of 15- to 25-nucleotide length, which can anneal to a part of a constant region, or a UTR primer 1 of 15- to 25-nucleotide length, which can anneal to a part of a 3' untranslated region,
   (2) the step of performing PCR by using the adaptor primer mentioned below, the C primer 2 or UTR primer 2 mentioned below, and the amplification product 1 as the template to obtain an amplification product 2;
   an adapter primer of 15- to 25-nucleotide length, which can anneal to the adapter part of the amplification product 1,
   a C primer 2 of 15- to 25-nucleotide length, which can anneal to a part of the constant region existing inside the region to which the C primer 1 anneals, or a UTR primer 2 of 15- to 25-nucleotide length, which can anneal to a part of a 3' untranslated region existing inside the region to which the UTR primer 1 anneals, wherein:
   in the step (1),
   as the L primer, at least one kind of L primer corresponding to TCRα (AL) and at least one kind of L primer corresponding to TCRβ (BL) are used;
   as the C primer 1, a C primer 1 corresponding to TCRα (Ca_RV1) and a C primer 1 corresponding to TCRβ (Cb_RV1) are used, or as the UTR primer 1, a UTR primer 1 corresponding to TCRα (AC_UTR1) and a UTR primer 1 corresponding to TCRβ (BC_UTR1) are used, and
   TCRα and TCRβ are simultaneously amplified,
   and wherein the leader region-annealing part of AL consists of a part of any one of the nucleotide sequences of SEQ ID NOS: 87 to 140, and the leader region-annealing part of BL consists of a part of any one of the nucleotide sequences of SEQ ID NOS: 141 to 188.

2. The amplification method according to claim 1, wherein the leader region-annealing part of AL consists of any one of the nucleotide sequences of SEQ ID NOS: 1 to 41, and the leader region-annealing part of BL consists of any one of the nucleotide sequences of SEQ ID NOS: 42 to 80, or the leader region-annealing sequence of AL consists of any one of the nucleotide sequences of SEQ ID NOS: 283 to 328, and the leader region-annealing sequence of BL consists of any one of the nucleotide sequences of SEQ ID NOS: 329 to 350.

3. The amplification method according to claim 2, wherein 41 kinds of ALs corresponding to the sequences of SEQ ID NOS: 1 to 41, respectively, and 39 kinds of BLs corresponding to the sequences of SEQ ID NOS: 42 to 80, respectively, are used as the L primer, or 46 kinds of ALs corresponding to the sequences of SEQ ID NOS: 283 to 328, respectively, and 22 kinds of BLs corresponding to the sequences of SEQ ID NOS: 329 to 350, respectively, are used as the L primer.

4. The amplification method according to claim 1, wherein the adapter part of AL consists of the nucleotide sequence of SEQ ID NO: 81, and the adapter part of BL consists of the nucleotide sequence of SEQ ID NO: 82.

5. The amplification method according to claim 1, wherein:
   Ca_RV1 is a polynucleotide consisting of the nucleotide sequence of SEQ ID NO: 83 or SEQ ID NO: 351, and Cb_RV1 is a polynucleotide consisting of the nucleotide sequences of SEQ ID NO: 84 or SEQ ID NO: 353 and SEQ ID NO: 354, or
   AC_UTR1 is a polynucleotide consisting of the nucleotide sequence of SEQ ID NO: 277, and BC_UTR1 is a polynucleotide consisting of the nucleotide sequences of SEQ ID NO: 279 and/or SEQ ID NO: 280.

6. The amplification method according to claim 1, wherein:
   as the C primer 2, a C primer 2 corresponding to TCRα (Ca_RV2) and a C primer 2 corresponding to TCRβ (Cb_RV2) are used, Ca_RV2 consists of the nucleotide sequence of SEQ ID NO: 85 or SEQ ID NO: 352, and Cb_RV2 consists of the nucleotide sequence of SEQ ID NO: 86 or SEQ ID NO: 355, or
   as the UTR primer 2, a UTR primer 2 corresponding to TCRα (AC_UTR2) and a C primer 2 corresponding to TCRβ (BC_UTR2) are used, AC_UTR2 consists of the nucleotide sequence of SEQ ID NO: 278, and BC_UTR2 consists of the nucleotide sequences of SEQ ID NO: 281 and/or SEQ ID NO: 282.

7. A kit for amplifying a TCR cDNA, which comprises:
an L primer of 30- to 60-nucleotide length comprising an adapter part of 15- to 25-nucleotide length, and a leader region-annealing part of 15- to 25-nucleotide length, which is ligated downstream from the adapter part, and can anneal to a part of a leader region of a TCR cDNA which contains a translation initiation codon, or to a part of the TCR cDNA which is an upstream part of the leader region, wherein the L primer comprises at least one kind of L primer corresponding to TCRα (AL) and at least one kind of L primer corresponding to TCRβ (BL),
a C primer 1 of 15- to 25-nucleotide length, which can anneal to a part of a constant region, or a UTR primer 1 of 15- to 25-nucleotide length, which can anneal to a part of a 3' untranslated region,
an adapter primer of 15- to 25-nucleotide length, which can anneal to the adapter part of an amplification product 1,
a C primer 2 of 15- to 25-nucleotide length, which can anneal to a part of the constant region existing inside the region to which the C primer 1 anneals, or a UTR primer 2 of 15- to 25-nucleotide length, which can anneal to a part of the 3' untranslated region existing inside the region to which the UTR primer 1 anneals, wherein the leader region-annealing part of AL can anneal to a region consisting of any one of the nucleotide sequences of SEQ ID NOS: 85 to 140, and the leader region-annealing part of BL can anneal to a region consisting of any one of the nucleotide sequences of SEQ ID NOS: 141 to 188.

8. The kit according to claim 7, wherein the leader region-annealing sequence of AL consists of any one of the nucleotide sequences of SEQ ID NOS: 1 to 41, and the leader region-annealing sequence of BL consists of any one of the nucleotide sequences of SEQ ID NOS: 42 to 80.

9. The kit according to claim 8, which comprises 41 kinds of ALs corresponding to the sequences of SEQ ID NOS: 1 to 41, respectively, and 39 kinds of BLs corresponding to the sequences of SEQ ID NOS: 42 to 80, respectively.

* * * * *